US012569335B2

(12) United States Patent
Hacohen

(10) Patent No.: US 12,569,335 B2
(45) Date of Patent: Mar. 10, 2026

(54) PROSTHETIC HEART VALVE WITH FRAMES

(71) Applicant: CARDIOVALVE LTD., Or Yehuda (IL)

(72) Inventor: Gil Hacohen, Ramat Gan (IL)

(73) Assignee: CARDIOVALVE LTD., Or Yehuda (IL)

( * ) Notice: Subject to any disclaimer, the term of this patent is extended or adjusted under 35 U.S.C. 154(b) by 323 days.

(21) Appl. No.: 18/384,139

(22) Filed: Oct. 26, 2023

(65) Prior Publication Data

US 2024/0050227 A1     Feb. 15, 2024

Related U.S. Application Data

(60) Continuation of application No. 17/734,472, filed on May 2, 2022, now Pat. No. 11,839,541, which is a continuation of application No. 17/479,418, filed on Sep. 20, 2021, now Pat. No. 11,351,026, which is a continuation of application No. 16/811,732, filed on Mar. 6, 2020, now Pat. No. 11,141,268, which is a
(Continued)

(51) Int. Cl.
*A61F 2/24*          (2006.01)

(52) U.S. Cl.
CPC .......... *A61F 2/2418* (2013.01); *A61F 2/2409* (2013.01); *A61F 2/2454* (2013.01); *A61F 2/2457* (2013.01); *A61F 2220/0016* (2013.01)

(58) Field of Classification Search
CPC .... A61F 2/2418; A61F 2/2409; A61F 2/2454; A61F 2/2457
See application file for complete search history.

(56) References Cited

U.S. PATENT DOCUMENTS

| | | | |
|---|---|---|---|
| 3,604,488 A | 9/1971 | Wishart et al. | |
| 3,656,185 A | 4/1972 | Carpentier | |

(Continued)

FOREIGN PATENT DOCUMENTS

| | | |
|---|---|---|
| CA | 2822801 | 8/2006 |
| CA | 2671966 | 6/2008 |

(Continued)

OTHER PUBLICATIONS

An Office Action dated Jun. 18, 2024, which issued during the prosecution of U.S. Appl. No. 17/399,594.

(Continued)

*Primary Examiner* — Suba Ganesan
(74) *Attorney, Agent, or Firm* — Sughrue Mion, PLLC

(57) ABSTRACT

A prosthetic heart valve includes a first frame shaped having metal segments and defines a lumen therethrough. A leaflet frame is coupled to and disposed within the lumen of the first frame. A second frame is configured to be placed against an upstream surface of the native valve. A plurality of prosthetic leaflets are coupled to the leaflet frame and facilitate upstream-to-downstream bloodflow through the prosthetic valve. Fabric couples the first and second frames together in the collapsed and expanded states of the prosthetic valve. In the expanded state of the prosthetic valve, the fabric separates a downstream end of the second frame and an upstream end of the metal segments of the first frame in a manner in which a gap is defined between the first and second frames, with no metallic structure being disposed within the gap. Other embodiments are also described.

18 Claims, 6 Drawing Sheets

Related U.S. Application Data continuation of application No. 16/532,945, filed on Aug. 6, 2019, now Pat. No. 10,660,751, which is a continuation of application No. 16/388,038, filed on Apr. 18, 2019, now Pat. No. 10,548,726, which is a continuation of application No. 16/183,140, filed on Nov. 7, 2018, now Pat. No. 10,610,359, which is a division of application No. 15/188,507, filed on Jun. 21, 2016, now Pat. No. 10,231,831, which is a continuation of application No. 14/522,987, filed on Oct. 24, 2014, now abandoned, which is a continuation of application No. 12/961,721, filed on Dec. 7, 2010, now Pat. No. 8,870,950.

(60) Provisional application No. 61/283,819, filed on Dec. 8, 2009.

(56) References Cited

U.S. PATENT DOCUMENTS

| | | | |
|---|---|---|---|
| 3,840,018 A | 10/1974 | Heifetz | |
| 3,874,388 A | 4/1975 | King et al. | |
| 3,898,701 A | 8/1975 | La Russa | |
| 4,042,979 A | 8/1977 | Angell | |
| 4,118,805 A | 10/1978 | Reimels | |
| 4,214,349 A | 7/1980 | Munch | |
| 4,222,126 A | 9/1980 | Boretos et al. | |
| 4,261,342 A | 4/1981 | Aranguren | |
| 4,275,469 A | 6/1981 | Gabbay | |
| 4,340,091 A | 7/1982 | Skelton et al. | |
| 4,423,525 A | 1/1984 | Vallana et al. | |
| 4,434,828 A | 3/1984 | Trincia | |
| 4,473,928 A | 10/1984 | Johnson | |
| 4,602,911 A | 7/1986 | Ahmadi et al. | |
| 4,625,727 A | 12/1986 | Leiboff | |
| 4,712,549 A | 12/1987 | Peters et al. | |
| 4,778,468 A | 10/1988 | Hunt et al. | |
| 4,853,986 A | 8/1989 | Allen | |
| 4,892,541 A | 1/1990 | Alonso | |
| 4,917,698 A | 4/1990 | Carpenter et al. | |
| 4,961,738 A | 10/1990 | Mackin | |
| 4,972,494 A | 11/1990 | White et al. | |
| 4,994,077 A | 2/1991 | Dobben | |
| 5,061,277 A | 10/1991 | Carpentier et al. | |
| 5,078,739 A | 1/1992 | Martin | |
| 5,089,006 A | 2/1992 | Stiles | |
| 5,104,407 A | 4/1992 | Lam et al. | |
| 5,108,420 A | 4/1992 | Marks | |
| 5,201,757 A | 4/1993 | Heyn et al. | |
| 5,201,880 A | 4/1993 | Wright | |
| 5,258,008 A | 11/1993 | Wilk | |
| 5,275,622 A | 1/1994 | Lazarus et al. | |
| 5,300,034 A | 4/1994 | Behnke | |
| 5,306,296 A | 4/1994 | Wright et al. | |
| 5,314,473 A | 5/1994 | Godin | |
| 5,325,845 A | 7/1994 | Adair | |
| 5,332,402 A | 7/1994 | Teitelbaum | |
| 5,397,351 A | 3/1995 | Pavcnik et al. | |
| 5,405,378 A | 4/1995 | Strecker | |
| 5,443,500 A | 8/1995 | Sigwart | |
| 5,450,860 A | 9/1995 | O'Connor | |
| 5,473,812 A | 12/1995 | Morris et al. | |
| 5,477,856 A | 12/1995 | Lundquist | |
| 5,593,424 A | 1/1997 | Northrup, III | |
| 5,601,572 A | 2/1997 | Middleman et al. | |
| 5,607,444 A | 3/1997 | Lam | |
| 5,607,470 A | 3/1997 | Milo | |
| 5,626,609 A | 5/1997 | Zvenyatsky et al. | |
| 5,647,857 A | 7/1997 | Anderson et al. | |
| 5,669,919 A | 9/1997 | Sanders et al. | |
| 5,674,279 A | 10/1997 | Wright et al. | |
| 5,683,402 A | 11/1997 | Cosgrove et al. | |
| 5,702,397 A | 12/1997 | Goble et al. | |
| 5,702,398 A | 12/1997 | Tarabishy | |
| 5,709,695 A | 1/1998 | Northrup, III | |
| 5,713,948 A | 2/1998 | Uflacker | |
| 5,716,370 A | 2/1998 | Williamson et al. | |
| 5,716,397 A | 2/1998 | Myers | |
| 5,716,417 A | 2/1998 | Girard et al. | |
| 5,728,116 A | 3/1998 | Rosenman | |
| 5,730,150 A | 3/1998 | Peppel et al. | |
| 5,741,297 A | 4/1998 | Simon | |
| 5,749,371 A | 5/1998 | Zadini et al. | |
| 5,749,920 A | 5/1998 | Quiachon et al. | |
| 5,765,682 A | 6/1998 | Bley et al. | |
| 5,766,151 A | 6/1998 | Valley et al. | |
| 5,776,140 A | 7/1998 | Cottone | |
| 5,810,882 A | 9/1998 | Bolduc | |
| 5,824,066 A | 10/1998 | Gross | |
| 5,830,221 A | 11/1998 | Stein et al. | |
| 5,843,120 A | 12/1998 | Israel et al. | |
| 5,855,614 A | 1/1999 | Stevens et al. | |
| 5,868,777 A | 2/1999 | Lam | |
| 5,873,906 A | 2/1999 | Lau et al. | |
| 5,876,373 A | 3/1999 | Giba et al. | |
| 5,906,619 A | 5/1999 | Olson et al. | |
| 5,935,098 A | 8/1999 | Blaisdell et al. | |
| 5,954,766 A | 9/1999 | Zadno-Azizi et al. | |
| 5,957,949 A | 9/1999 | Leonhardt et al. | |
| 5,957,953 A | 9/1999 | DiPoto et al. | |
| 5,961,440 A | 10/1999 | Schweich et al. | |
| 5,961,539 A | 10/1999 | Northrup, III et al. | |
| 5,961,549 A | 10/1999 | Nguyen et al. | |
| 5,980,565 A | 11/1999 | Jayaraman | |
| 5,984,959 A | 11/1999 | Robertson | |
| 6,010,530 A | 1/2000 | Goicoechea | |
| 6,019,787 A | 2/2000 | Richard et al. | |
| 6,042,554 A | 3/2000 | Rosenman | |
| 6,042,607 A | 3/2000 | Williamson, IV | |
| 6,045,497 A | 4/2000 | Schweich et al. | |
| 6,050,936 A | 4/2000 | Schweich et al. | |
| 6,059,715 A | 5/2000 | Schweich et al. | |
| 6,059,827 A | 5/2000 | Fenton | |
| 6,074,401 A | 6/2000 | Gardiner et al. | |
| 6,074,417 A | 6/2000 | Peredo | |
| 6,102,945 A | 8/2000 | Campbell | |
| 6,106,550 A | 8/2000 | Magovern | |
| 6,110,200 A | 8/2000 | Hinnenkamp | |
| 6,113,612 A | 9/2000 | Swanson et al. | |
| 6,120,534 A | 9/2000 | Ruiz | |
| 6,126,686 A | 10/2000 | Badylak et al. | |
| 6,143,024 A | 11/2000 | Campbell et al. | |
| 6,152,937 A | 11/2000 | Peterson et al. | |
| 6,159,240 A | 12/2000 | Sparer | |
| 6,165,119 A | 12/2000 | Schweich et al. | |
| 6,165,183 A | 12/2000 | Kuehn et al. | |
| 6,165,210 A | 12/2000 | Lau et al. | |
| 6,174,332 B1 | 1/2001 | Loch | |
| 6,183,411 B1 | 2/2001 | Mortier et al. | |
| 6,187,020 B1 | 2/2001 | Zegdi et al. | |
| 6,187,040 B1 | 2/2001 | Wright | |
| 6,193,686 B1 | 2/2001 | Estrada et al. | |
| 6,193,745 B1 | 2/2001 | Fogarty et al. | |
| 6,217,610 B1 | 4/2001 | Carpentier et al. | |
| 6,221,102 B1 | 4/2001 | Baker et al. | |
| 6,231,602 B1 | 5/2001 | Carpentier et al. | |
| 6,251,092 B1 | 6/2001 | Qin et al. | |
| 6,254,609 B1 | 7/2001 | Vrba et al. | |
| 6,264,700 B1 | 7/2001 | Kilcoyne et al. | |
| 6,271,278 B1 | 8/2001 | Park et al. | |
| 6,287,339 B1 | 9/2001 | Vasquez et al. | |
| 6,296,656 B1 | 10/2001 | Bolduc et al. | |
| 6,312,465 B1 | 11/2001 | Griffin et al. | |
| 6,315,784 B1 | 11/2001 | Djurovic | |
| 6,319,281 B1 | 11/2001 | Patel | |
| 6,332,893 B1 | 12/2001 | Mortier et al. | |
| 6,334,873 B1 | 1/2002 | Lane et al. | |
| 6,346,074 B1 | 2/2002 | Roth | |
| 6,350,278 B1 | 2/2002 | Lenker et al. | |
| 6,352,561 B1 | 3/2002 | Leopold et al. | |
| 6,391,036 B1 | 5/2002 | Berg et al. | |
| 6,398,758 B1 | 6/2002 | Jacobsen et al. | |
| 6,402,780 B2 | 6/2002 | Williamson, IV | |

(56)                References Cited

U.S. PATENT DOCUMENTS

| | | | |
|---|---|---|---|
| 6,406,420 B1 | 6/2002 | McCarthy et al. |
| 6,406,493 B1 | 6/2002 | Tu et al. |
| 6,409,755 B1 | 6/2002 | Vrba |
| 6,419,696 B1 | 7/2002 | Ortiz et al. |
| 6,428,550 B1 | 8/2002 | Vargas et al. |
| 6,440,164 B1 | 8/2002 | Dimatteo et al. |
| 6,451,054 B1 | 9/2002 | Stevens |
| 6,454,799 B1 | 9/2002 | Schreck |
| 6,458,153 B1 | 10/2002 | Bailey et al. |
| 6,461,366 B1 | 10/2002 | Seguin |
| 6,470,892 B1 | 10/2002 | Forsell |
| 6,478,807 B1 | 11/2002 | Foreman et al. |
| 6,482,228 B1 | 11/2002 | Norred |
| 6,491,711 B1 | 12/2002 | Durcan |
| 6,503,274 B1 | 1/2003 | Howanec et al. |
| 6,511,491 B2 | 1/2003 | Grudem et al. |
| 6,524,338 B1 | 2/2003 | Gundry |
| 6,530,952 B2 | 3/2003 | Vesely |
| 6,533,772 B1 | 3/2003 | Sherts et al. |
| 6,537,314 B2 | 3/2003 | Langberg et al. |
| 6,540,782 B1 | 4/2003 | Snyders |
| 6,547,801 B1 | 4/2003 | Dargent et al. |
| 6,551,350 B1 | 4/2003 | Thornton et al. |
| 6,554,845 B1 | 4/2003 | Fleenor et al. |
| 6,558,396 B1 | 5/2003 | Inoue |
| 6,558,418 B2 | 5/2003 | Carpentier et al. |
| 6,564,805 B2 | 5/2003 | Garrison et al. |
| 6,565,603 B2 | 5/2003 | Cox |
| 6,569,196 B1 | 5/2003 | Vesely |
| 6,569,198 B1 | 5/2003 | Wilson et al. |
| 6,579,297 B2 | 6/2003 | Bicek et al. |
| 6,582,464 B2 | 6/2003 | Gabbay |
| 6,589,160 B2 | 7/2003 | Schweich et al. |
| 6,602,263 B1 | 8/2003 | Swanson et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,616,675 B1 | 9/2003 | Evard et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich et al. |
| 6,651,671 B1 | 11/2003 | Donlon et al. |
| 6,652,556 B1 | 11/2003 | VanTassel et al. |
| 6,669,724 B2 | 12/2003 | Park et al. |
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |
| 6,699,256 B1 | 3/2004 | Logan et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,709,456 B2 | 3/2004 | Langberg et al. |
| 6,711,444 B2 | 3/2004 | Koblish |
| 6,712,836 B1 | 3/2004 | Berg et al. |
| 6,716,244 B2 | 4/2004 | Klaco |
| 6,718,985 B2 | 4/2004 | Hlavka et al. |
| 6,719,781 B1 | 4/2004 | Kim |
| 6,719,786 B2 | 4/2004 | Ryan et al. |
| 6,719,788 B2 | 4/2004 | Cox |
| 6,723,038 B1 | 4/2004 | Schroeder et al. |
| 6,726,716 B2 | 4/2004 | Marquez |
| 6,726,717 B2 | 4/2004 | Alfieri et al. |
| 6,730,118 B2 | 5/2004 | Spenser et al. |
| 6,730,121 B2 | 5/2004 | Ortiz et al. |
| 6,733,525 B2 | 5/2004 | Yang et al. |
| 6,749,630 B2 | 6/2004 | McCarthy et al. |
| 6,752,813 B2 | 6/2004 | Goldfarb et al. |
| 6,755,857 B2 | 6/2004 | Peterson et al. |
| 6,764,310 B1 | 7/2004 | Ichihashi et al. |
| 6,764,510 B2 | 7/2004 | Vidlund et al. |
| 6,764,514 B1 | 7/2004 | Li et al. |
| 6,764,518 B2 | 7/2004 | Godin |
| 6,767,362 B2 | 7/2004 | Schreck |
| 6,770,083 B2 | 8/2004 | Seguin |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,821,297 B2 | 11/2004 | Snyders |
| 6,830,585 B1 | 12/2004 | Artof et al. |
| 6,830,638 B2 | 12/2004 | Boylan et al. |
| 6,849,084 B2 | 2/2005 | Rabkin et al. |
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,884,257 B1 | 4/2005 | Cox |
| 6,893,459 B1 | 5/2005 | Macoviak |
| 6,893,460 B2 | 5/2005 | Spenser et al. |
| 6,908,482 B2 | 6/2005 | McCarthy et al. |
| 6,918,917 B1 | 7/2005 | Nguyen et al. |
| 6,926,715 B1 | 8/2005 | Hauck et al. |
| 6,926,730 B1 | 8/2005 | Nguyen et al. |
| 6,939,370 B2 | 9/2005 | Hartley et al. |
| 6,951,571 B1 | 10/2005 | Srivastava |
| 6,960,217 B2 | 11/2005 | Bolduc |
| 6,964,684 B2 | 11/2005 | Ortiz et al. |
| 6,964,686 B2 | 11/2005 | Gordon |
| 6,974,476 B2 | 12/2005 | McGuckin et al. |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,011,669 B2 | 3/2006 | Kimblad |
| 7,011,681 B2 | 3/2006 | Vesely |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,041,132 B2 | 5/2006 | Quijano et al. |
| 7,074,236 B2 | 7/2006 | Rabkin et al. |
| 7,077,850 B2 | 7/2006 | Kortenbach |
| 7,077,861 B2 | 7/2006 | Spence |
| 7,077,862 B2 | 7/2006 | Vidlund et al. |
| 7,087,064 B1 | 8/2006 | Hyde |
| 7,101,336 B2 | 9/2006 | Miller |
| 7,101,395 B2 | 9/2006 | Tremulis et al. |
| 7,101,396 B2 | 9/2006 | Artof et al. |
| 7,112,207 B2 | 9/2006 | Allen et al. |
| 7,118,595 B2 | 10/2006 | Ryan et al. |
| 7,125,421 B2 | 10/2006 | Tremulis et al. |
| 7,137,184 B2 | 11/2006 | Schreck |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,656 B2 | 2/2007 | Khairkhahan |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,198,646 B2 | 4/2007 | Figulla et al. |
| 7,201,772 B2 | 4/2007 | Schwammenthal |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,252,682 B2 | 8/2007 | Seguin |
| 7,261,686 B2 | 8/2007 | Couvillon, Jr. |
| 7,288,097 B2 | 10/2007 | Seguin |
| 7,288,111 B1 | 10/2007 | Holloway et al. |
| 7,294,148 B2 | 11/2007 | McCarthy |

(56) References Cited

U.S. PATENT DOCUMENTS

| | | | |
|---|---|---|---|
| 7,297,150 B2 | 11/2007 | Cartledge et al. |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,316,716 B2 | 1/2008 | Egan |
| 7,329,279 B2 | 2/2008 | Haug et al. |
| 7,329,280 B2 | 2/2008 | Bolling et al. |
| 7,335,213 B1 | 2/2008 | Hyde et al. |
| 7,351,256 B2 | 4/2008 | Hojeibane et al. |
| 7,361,190 B2 | 4/2008 | Shoulian et al. |
| 7,364,588 B2 | 4/2008 | Mathis et al. |
| 7,374,571 B2 | 5/2008 | Pease et al. |
| 7,374,573 B2 | 5/2008 | Gabbay |
| 7,377,938 B2 | 5/2008 | Sarac et al. |
| 7,377,941 B2 | 5/2008 | Rhee et al. |
| 7,381,218 B2 | 6/2008 | Schreck |
| 7,381,219 B2 | 6/2008 | Salahieh et al. |
| 7,390,329 B2 | 6/2008 | Westra et al. |
| 7,404,824 B1 | 7/2008 | Webler et al. |
| 7,422,603 B2 | 9/2008 | Lane |
| 7,429,269 B2 | 9/2008 | Schwammenthal |
| 7,431,692 B2 | 10/2008 | Zollinger et al. |
| 7,442,204 B2 | 10/2008 | Schwammenthal |
| 7,442,207 B2 | 10/2008 | Rafiee |
| 7,445,630 B2 | 11/2008 | Lashinski et al. |
| 7,452,376 B2 | 11/2008 | Lim et al. |
| 7,455,677 B2 | 11/2008 | Vargas et al. |
| 7,455,688 B2 | 11/2008 | Furst et al. |
| 7,455,690 B2 | 11/2008 | Cartledge et al. |
| 7,462,162 B2 | 12/2008 | Phan et al. |
| 7,481,838 B2 | 1/2009 | Carpentier et al. |
| 7,485,142 B2 | 2/2009 | Milo |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb et al. |
| 7,513,909 B2 | 4/2009 | Lane et al. |
| 7,524,331 B2 | 4/2009 | Birdsall |
| 7,527,646 B2 | 5/2009 | Rahdert et al. |
| 7,527,647 B2 | 5/2009 | Spence |
| 7,530,995 B2 | 5/2009 | Quijano et al. |
| 7,549,983 B2 | 6/2009 | Roue et al. |
| 7,556,632 B2 | 7/2009 | Zadno |
| 7,556,646 B2 | 7/2009 | Yang et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,582,111 B2 | 9/2009 | Krolik et al. |
| 7,585,321 B2 | 9/2009 | Cribier |
| 7,588,582 B2 | 9/2009 | Starksen et al. |
| 7,591,826 B2 | 9/2009 | Alferness et al. |
| 7,597,711 B2 | 10/2009 | Drews et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,611,534 B2 | 11/2009 | Kapadia et al. |
| 7,618,449 B2 | 11/2009 | Tremulis et al. |
| 7,621,948 B2 | 11/2009 | Hermann et al. |
| 7,625,403 B2 | 12/2009 | Krivoruchko |
| 7,632,302 B2 | 12/2009 | Vreeman et al. |
| 7,632,303 B1 | 12/2009 | Stalker et al. |
| 7,635,329 B2 | 12/2009 | Goldfarb et al. |
| 7,635,386 B1 | 12/2009 | Gammie |
| 7,648,528 B2 | 1/2010 | Styrc |
| 7,655,015 B2 | 2/2010 | Goldfarb et al. |
| 7,666,204 B2 | 2/2010 | Thornton et al. |
| 7,682,319 B2 | 3/2010 | Martin |
| 7,682,369 B2 | 3/2010 | Seguin |
| 7,682,380 B2 | 3/2010 | Thornton et al. |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,708,775 B2 | 5/2010 | Rowe et al. |
| 7,717,951 B2 | 5/2010 | Flagle et al. |
| 7,717,952 B2 | 5/2010 | Case et al. |
| 7,717,955 B2 | 5/2010 | Lane et al. |
| 7,722,666 B2 | 5/2010 | Lafontaine |
| 7,731,741 B2 | 6/2010 | Eidenschink |
| 7,731,742 B2 | 6/2010 | Schlick et al. |
| 7,736,388 B2 | 6/2010 | Goldfarb et al. |
| 7,748,389 B2 | 7/2010 | Salahieh et al. |
| 7,753,922 B2 | 7/2010 | Starksen |
| 7,753,924 B2 | 7/2010 | Starksen et al. |
| 7,753,949 B2 | 7/2010 | Lamphere et al. |
| 7,758,595 B2 | 7/2010 | Allen et al. |
| 7,758,632 B2 | 7/2010 | Hojeibane et al. |
| 7,758,640 B2 | 7/2010 | Vesely |
| 7,771,467 B2 | 8/2010 | Svensson |
| 7,771,469 B2 | 8/2010 | Liddicoat |
| 7,776,080 B2 | 8/2010 | Bei et al. |
| 7,776,083 B2 | 8/2010 | Vesely |
| 7,780,726 B2 | 8/2010 | Seguin |
| 7,785,341 B2 | 8/2010 | Forster et al. |
| 7,799,069 B2 | 9/2010 | Bailey et al. |
| 7,803,181 B2 | 9/2010 | Furst et al. |
| 7,811,296 B2 | 10/2010 | Goldfarb et al. |
| 7,811,316 B2 | 10/2010 | Kalmann et al. |
| 7,824,442 B2 | 11/2010 | Salahieh et al. |
| 7,837,645 B2 | 11/2010 | Bessler et al. |
| 7,837,727 B2 | 11/2010 | Goetz et al. |
| 7,842,081 B2 | 11/2010 | Yadin |
| 7,850,725 B2 | 12/2010 | Vardi et al. |
| 7,871,368 B2 | 1/2011 | Zollinger et al. |
| 7,871,432 B2 | 1/2011 | Bergin |
| 7,871,433 B2 | 1/2011 | Lattouf |
| 7,871,436 B2 | 1/2011 | Ryan et al. |
| 7,887,583 B2 | 2/2011 | Macoviak |
| 7,892,281 B2 | 2/2011 | Seguin et al. |
| 7,896,915 B2 | 3/2011 | Guyenot et al. |
| 7,914,544 B2 | 3/2011 | Nguyen et al. |
| 7,914,569 B2 | 3/2011 | Nguyen et al. |
| 7,927,370 B2 | 4/2011 | Webler et al. |
| 7,927,371 B2 | 4/2011 | Navia et al. |
| 7,942,927 B2 | 5/2011 | Kaye et al. |
| 7,947,072 B2 | 5/2011 | Yang et al. |
| 7,947,075 B2 | 5/2011 | Goetz et al. |
| 7,951,195 B2 | 5/2011 | Antonsson et al. |
| 7,955,375 B2 | 6/2011 | Agnew |
| 7,955,377 B2 | 6/2011 | Melsheimer |
| 7,955,384 B2 | 6/2011 | Rafiee et al. |
| 7,959,666 B2 | 6/2011 | Salahieh et al. |
| 7,959,672 B2 | 6/2011 | Salahieh et al. |
| 7,967,833 B2 | 6/2011 | Sterman et al. |
| 7,967,857 B2 | 6/2011 | Lane |
| 7,981,151 B2 | 7/2011 | Rowe |
| 7,981,153 B2 | 7/2011 | Fogarty et al. |
| 7,988,725 B2 | 8/2011 | Gross et al. |
| 7,992,567 B2 | 8/2011 | Hirotsuka et al. |
| 7,993,368 B2 | 8/2011 | Gambale et al. |
| 7,993,392 B2 | 8/2011 | Righini et al. |
| 7,993,393 B2 | 8/2011 | Carpentier et al. |
| 7,993,397 B2 | 8/2011 | Lashinski |
| 8,002,825 B2 | 8/2011 | Letac et al. |
| 8,002,826 B2 | 8/2011 | Seguin |
| 8,012,201 B2 | 9/2011 | Lashinski et al. |
| 8,016,877 B2 | 9/2011 | Seguin et al. |
| 8,016,882 B2 | 9/2011 | Macoviak |
| 8,021,420 B2 | 9/2011 | Dolan |
| 8,021,421 B2 | 9/2011 | Fogarty et al. |
| 8,025,695 B2 | 9/2011 | Fogarty et al. |
| 8,029,518 B2 | 10/2011 | Goldfarb et al. |
| 8,029,557 B2 | 10/2011 | Sobrino-Serrano et al. |
| 8,029,564 B2 | 10/2011 | Johnson et al. |
| 8,034,103 B2 | 10/2011 | Burriesci |
| 8,034,104 B2 | 10/2011 | Carpentier et al. |
| 8,038,720 B2 | 10/2011 | Wallace et al. |
| 8,043,360 B2 | 10/2011 | McNamara et al. |
| 8,048,138 B2 | 11/2011 | Sulivan et al. |
| 8,048,140 B2 | 11/2011 | Purdy |
| 8,048,153 B2 | 11/2011 | Salahieh et al. |

(56)　　References Cited

U.S. PATENT DOCUMENTS

| | | | |
|---|---|---|---|
| 8,052,592 | B2 | 11/2011 | Goldfarb et al. |
| 8,052,741 | B2 | 11/2011 | Bruszewski et al. |
| 8,052,749 | B2 | 11/2011 | Salahieh et al. |
| 8,057,493 | B2 | 11/2011 | Goldfarb et al. |
| 8,057,532 | B2 | 11/2011 | Hoffman |
| 8,057,540 | B2 | 11/2011 | Letac et al. |
| 8,062,355 | B2 | 11/2011 | Figulla et al. |
| 8,062,359 | B2 | 11/2011 | Marquez et al. |
| 8,070,708 | B2 | 12/2011 | Rottenberg et al. |
| 8,070,800 | B2 | 12/2011 | Lock et al. |
| 8,070,802 | B2 | 12/2011 | Lamphere et al. |
| 8,070,804 | B2 | 12/2011 | Hyde |
| 8,070,805 | B2 | 12/2011 | Vidlund |
| 8,075,611 | B2 | 12/2011 | Milwee et al. |
| 8,075,616 | B2 | 12/2011 | Solem |
| 8,080,054 | B2 | 12/2011 | Rowe |
| 8,083,793 | B2 | 12/2011 | Lane et al. |
| D652,927 | S | 1/2012 | Braido et al. |
| D653,341 | S | 1/2012 | Braido et al. |
| 8,092,518 | B2 | 1/2012 | Schreck |
| 8,092,520 | B2 | 1/2012 | Quadri |
| 8,092,521 | B2 | 1/2012 | Figulla et al. |
| 8,100,964 | B2 | 1/2012 | Spence |
| 8,105,377 | B2 | 1/2012 | Liddicoat |
| 8,109,996 | B2 | 2/2012 | Stacchino et al. |
| 8,118,866 | B2 | 2/2012 | Herrmann et al. |
| 8,123,800 | B2 | 2/2012 | McCarthy |
| 8,123,801 | B2 | 2/2012 | Milo |
| 8,133,270 | B2 | 3/2012 | Kheradvar et al. |
| 8,136,218 | B2 | 3/2012 | Millwee et al. |
| 8,137,398 | B2 | 3/2012 | Tuval et al. |
| 8,142,492 | B2 | 3/2012 | Forster et al. |
| 8,142,493 | B2 | 3/2012 | Spence et al. |
| 8,142,494 | B2 | 3/2012 | Rahdert et al. |
| 8,142,495 | B2 | 3/2012 | Hasenkam et al. |
| 8,142,496 | B2 | 3/2012 | Berreklouw |
| 8,142,497 | B2 | 3/2012 | Friedman |
| 8,147,504 | B2 | 4/2012 | Ino et al. |
| 8,147,542 | B2 | 4/2012 | Maisano et al. |
| 8,152,844 | B2 | 4/2012 | Rao |
| 8,157,852 | B2 | 4/2012 | Bloom et al. |
| 8,157,853 | B2 | 4/2012 | Laske et al. |
| 8,157,860 | B2 | 4/2012 | McNamara et al. |
| 8,163,008 | B2 | 4/2012 | Wilson et al. |
| 8,163,013 | B2 | 4/2012 | Machold et al. |
| 8,163,014 | B2 | 4/2012 | Lane et al. |
| D660,433 | S | 5/2012 | Braido et al. |
| D660,967 | S | 5/2012 | Braido et al. |
| 8,167,894 | B2 | 5/2012 | Miles et al. |
| 8,167,932 | B2 | 5/2012 | Bourang et al. |
| 8,167,935 | B2 | 5/2012 | McGuckin, Jr. et al. |
| 8,172,896 | B2 | 5/2012 | McNamara et al. |
| 8,172,898 | B2 | 5/2012 | Alferness et al. |
| 8,177,836 | B2 | 5/2012 | Lee et al. |
| 8,182,528 | B2 | 5/2012 | Salahieh et al. |
| 8,187,299 | B2 | 5/2012 | Goldfarb et al. |
| 8,187,324 | B2 | 5/2012 | Webler et al. |
| 8,202,315 | B2 | 6/2012 | Hlavka et al. |
| 8,206,439 | B2 | 6/2012 | Gomez-Duran |
| 8,211,169 | B2 | 7/2012 | Lane et al. |
| 8,216,256 | B2 | 7/2012 | Raschdorf, Jr. et al. |
| 8,216,301 | B2 | 7/2012 | Bonhoeffer et al. |
| 8,221,492 | B2 | 7/2012 | Case et al. |
| 8,221,493 | B2 | 7/2012 | Boyle et al. |
| 8,226,710 | B2 | 7/2012 | Nguyen et al. |
| 8,226,711 | B2 | 7/2012 | Mortier et al. |
| 8,231,670 | B2 | 7/2012 | Salahieh et al. |
| 8,231,671 | B2 | 7/2012 | Kim |
| 8,236,045 | B2 | 8/2012 | Benichou et al. |
| 8,236,049 | B2 | 8/2012 | Rowe et al. |
| 8,241,351 | B2 | 8/2012 | Cabiri |
| 8,252,042 | B2 | 8/2012 | McNamara et al. |
| 8,252,050 | B2 | 8/2012 | Maisano et al. |
| 8,252,051 | B2 | 8/2012 | Chau et al. |
| 8,252,052 | B2 | 8/2012 | Salahieh et al. |
| 8,257,390 | B2 | 9/2012 | Carley et al. |
| 8,262,725 | B2 | 9/2012 | Subramanian |
| 8,267,988 | B2 | 9/2012 | Hamer et al. |
| 8,277,501 | B2 | 10/2012 | Chalekian et al. |
| 8,277,502 | B2 | 10/2012 | Miller et al. |
| 8,287,584 | B2 | 10/2012 | Salahieh et al. |
| 8,287,591 | B2 | 10/2012 | Keidar et al. |
| 8,298,280 | B2 | 10/2012 | Yadin et al. |
| 8,303,608 | B2 | 11/2012 | Goldfarb et al. |
| 8,303,653 | B2 | 11/2012 | Bonhoeffer et al. |
| 8,308,798 | B2 | 11/2012 | Pintor et al. |
| 8,313,525 | B2 | 11/2012 | Tuval et al. |
| 8,317,853 | B2 | 11/2012 | Agnew |
| 8,317,855 | B2 | 11/2012 | Gregorich et al. |
| 8,323,334 | B2 | 12/2012 | Deem et al. |
| 8,323,335 | B2 | 12/2012 | Rowe et al. |
| 8,328,868 | B2 | 12/2012 | Paul et al. |
| 8,333,777 | B2 | 12/2012 | Schaller et al. |
| 8,337,541 | B2 | 12/2012 | Quadri et al. |
| 8,343,173 | B2 | 1/2013 | Starksen et al. |
| 8,343,174 | B2 | 1/2013 | Goldfarb et al. |
| 8,343,213 | B2 | 1/2013 | Salahieh et al. |
| 8,348,999 | B2 | 1/2013 | Kheradvar et al. |
| 8,349,002 | B2 | 1/2013 | Milo |
| 8,353,956 | B2 | 1/2013 | Miller et al. |
| 8,357,195 | B2 | 1/2013 | Kuehn |
| 8,361,144 | B2 | 1/2013 | Fish et al. |
| 8,366,767 | B2 | 2/2013 | Zhang |
| 8,372,140 | B2 | 2/2013 | Hoffman et al. |
| 8,377,119 | B2 | 2/2013 | Drews et al. |
| 8,382,829 | B1 | 2/2013 | Call et al. |
| 8,388,680 | B2 | 3/2013 | Starksen et al. |
| 8,393,517 | B2 | 3/2013 | Milo |
| 8,398,708 | B2 | 3/2013 | Meiri et al. |
| 8,403,981 | B2 | 3/2013 | Forster et al. |
| 8,403,983 | B2 | 3/2013 | Quadri et al. |
| 8,408,214 | B2 | 4/2013 | Spenser |
| 8,414,644 | B2 | 4/2013 | Quadri et al. |
| 8,425,593 | B2 | 4/2013 | Braido et al. |
| 8,430,926 | B2 | 4/2013 | Kirson |
| 8,430,934 | B2 | 4/2013 | Das |
| 8,444,689 | B2 | 5/2013 | Zhang |
| 8,449,599 | B2 | 5/2013 | Chau et al. |
| 8,449,625 | B2 | 5/2013 | Campbell et al. |
| 8,454,686 | B2 | 6/2013 | Alkhatib |
| 8,460,365 | B2 | 6/2013 | Haverkost et al. |
| 8,460,370 | B2 | 6/2013 | Zakay et al. |
| 8,460,371 | B2 | 6/2013 | Hlavka et al. |
| 8,474,460 | B2 | 7/2013 | Barrett et al. |
| 8,475,491 | B2 | 7/2013 | Milo |
| 8,480,732 | B2 | 7/2013 | Subramanian |
| 8,500,800 | B2 | 8/2013 | Maisano et al. |
| 8,500,821 | B2 | 8/2013 | Sobrino-Serrano et al. |
| 8,512,400 | B2 | 8/2013 | Tran et al. |
| 8,518,107 | B2 | 8/2013 | Tsukashima et al. |
| 8,523,881 | B2 | 9/2013 | Cabiri et al. |
| 8,523,940 | B2 | 9/2013 | Richardson et al. |
| 8,529,431 | B2 | 9/2013 | Baker et al. |
| 8,539,662 | B2 | 9/2013 | Stacchino et al. |
| 8,540,767 | B2 | 9/2013 | Zhang |
| 8,545,544 | B2 | 10/2013 | Spenser et al. |
| 8,545,553 | B2 | 10/2013 | Zipory et al. |
| 8,551,160 | B2 | 10/2013 | Figulla et al. |
| 8,551,161 | B2 | 10/2013 | Dolan |
| 8,562,672 | B2 | 10/2013 | Bonhoeffer et al. |
| 8,568,475 | B2 | 10/2013 | Nguyen et al. |
| 8,579,964 | B2 | 11/2013 | Lane et al. |
| 8,579,965 | B2 | 11/2013 | Bonhoeffer et al. |
| 8,585,755 | B2 | 11/2013 | Chau et al. |
| 8,585,756 | B2 | 11/2013 | Bonhoeffer et al. |
| 8,591,460 | B2 | 11/2013 | Wilson et al. |
| 8,591,570 | B2 | 11/2013 | Revuelta et al. |
| 8,591,576 | B2 | 11/2013 | Hasenkam et al. |
| 8,608,797 | B2 | 12/2013 | Gross et al. |
| 8,623,075 | B2 | 1/2014 | Murray et al. |
| 8,623,080 | B2 | 1/2014 | Fogarty et al. |
| 8,628,569 | B2 | 1/2014 | Benichou et al. |
| 8,628,570 | B2 | 1/2014 | Seguin |
| 8,628,571 | B1 | 1/2014 | Hacohen et al. |

(56) References Cited

U.S. PATENT DOCUMENTS

| | | | |
|---|---|---|---|
| 8,641,727 B2 | 2/2014 | Starksen et al. |
| 8,652,202 B2 | 2/2014 | Alon et al. |
| 8,652,203 B2 | 2/2014 | Quadri et al. |
| 8,652,204 B2 | 2/2014 | Quill et al. |
| 8,657,872 B2 | 2/2014 | Seguin |
| 8,663,322 B2 | 3/2014 | Keranen |
| 8,673,020 B2 | 3/2014 | Sobrino-Serrano et al. |
| 8,679,174 B2 | 3/2014 | Ottma et al. |
| 8,685,086 B2 | 4/2014 | Navia et al. |
| 8,690,939 B2 | 4/2014 | Miller et al. |
| 8,696,742 B2 | 4/2014 | Pintor et al. |
| 8,715,342 B2 | 5/2014 | Zipory et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,734,507 B2 | 5/2014 | Keranen |
| 8,740,920 B2 | 6/2014 | Goldfarb et al. |
| 8,747,460 B2 | 6/2014 | Tuval et al. |
| 8,771,345 B2 | 7/2014 | Tuval et al. |
| 8,778,021 B2 | 7/2014 | Cartledge |
| 8,784,472 B2 | 7/2014 | Eidenschink |
| 8,784,479 B2 | 7/2014 | Antonsson et al. |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,801,776 B2 | 8/2014 | House et al. |
| 8,808,366 B2 | 8/2014 | Braido et al. |
| 8,808,368 B2 | 8/2014 | Maisano et al. |
| 8,808,371 B2 | 8/2014 | Cartledge |
| 8,834,551 B2 | 9/2014 | Mcguckin, Jr. |
| 8,840,663 B2 | 9/2014 | Salahieh et al. |
| 8,840,664 B2 | 9/2014 | Karapetian et al. |
| 8,845,717 B2 | 9/2014 | Khairkhahan et al. |
| 8,845,722 B2 | 9/2014 | Gabbay |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,870,950 B2 | 10/2014 | Hacohen |
| 8,876,800 B2 | 11/2014 | Behan |
| 8,888,843 B2 | 11/2014 | Khairkhahan et al. |
| 8,894,702 B2 | 11/2014 | Quadri et al. |
| 8,900,294 B2 | 12/2014 | Paniagua et al. |
| 8,900,295 B2 | 12/2014 | Migliazza et al. |
| 8,906,083 B2 | 12/2014 | Obermiller et al. |
| 8,911,455 B2 | 12/2014 | Quadri et al. |
| 8,911,461 B2 | 12/2014 | Traynor et al. |
| 8,911,489 B2 | 12/2014 | Ben-Muvhar |
| 8,911,493 B2 | 12/2014 | Rowe et al. |
| 8,911,494 B2 | 12/2014 | Hammer et al. |
| 8,926,695 B2 | 1/2015 | Gross et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,042 B2 | 1/2015 | Miller et al. |
| 8,940,044 B2 | 1/2015 | Hammer et al. |
| 8,945,177 B2 | 2/2015 | Dell et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,595 B2 | 2/2015 | Alkhatib |
| 8,979,922 B2 | 3/2015 | Jayasinghe et al. |
| 8,986,370 B2 | 3/2015 | Annest |
| 8,986,373 B2 | 3/2015 | Chau et al. |
| 8,986,375 B2 | 3/2015 | Garde et al. |
| 8,992,599 B2 | 3/2015 | Thubrikar et al. |
| 8,992,604 B2 | 3/2015 | Gross et al. |
| 8,992,608 B2 | 3/2015 | Haug et al. |
| 8,998,982 B2 | 4/2015 | Richter et al. |
| 9,005,273 B2 | 4/2015 | Salahieh et al. |
| 9,011,468 B2 | 4/2015 | Ketai et al. |
| 9,011,520 B2 | 4/2015 | Miller et al. |
| 9,011,527 B2 | 4/2015 | Li et al. |
| 9,011,530 B2 | 4/2015 | Reich et al. |
| 9,017,399 B2 | 4/2015 | Gross et al. |
| D730,520 S | 5/2015 | Braido et al. |
| D730,521 S | 5/2015 | Braido et al. |
| 9,023,100 B2 | 5/2015 | Quadri et al. |
| 9,034,032 B2 | 5/2015 | McLean et al. |
| 9,034,033 B2 | 5/2015 | McLean et al. |
| 9,039,757 B2 | 5/2015 | McLean et al. |
| D732,666 S | 6/2015 | Nguyen et al. |
| 9,050,188 B2 | 6/2015 | Schweich et al. |
| 9,060,858 B2 | 6/2015 | Thornton et al. |
| 9,072,603 B2 | 7/2015 | Tuval et al. |
| 9,084,676 B2 | 7/2015 | Chau et al. |
| 9,095,434 B2 | 8/2015 | Rowe |
| 9,119,719 B2 | 9/2015 | Zipory et al. |
| 9,125,632 B2 | 9/2015 | Loulmet et al. |
| 9,125,738 B2 | 9/2015 | Figulla et al. |
| 9,125,740 B2 | 9/2015 | Morriss et al. |
| 9,132,006 B2 | 9/2015 | Spenser et al. |
| 9,132,009 B2 | 9/2015 | Hacohen et al. |
| 9,138,312 B2 | 9/2015 | Tuval et al. |
| 9,155,619 B2 | 10/2015 | Liu et al. |
| 9,173,646 B2 | 11/2015 | Fabro |
| 9,173,659 B2 | 11/2015 | Bodewadt et al. |
| 9,173,738 B2 | 11/2015 | Murray et al. |
| 9,180,005 B1 | 11/2015 | Lashinski et al. |
| 9,180,009 B2 | 11/2015 | Majkrzak et al. |
| 9,192,472 B2 | 11/2015 | Gross et al. |
| 9,216,076 B2 | 12/2015 | Mitra et al. |
| 9,220,594 B2 | 12/2015 | Braido et al. |
| 9,226,820 B2 | 1/2016 | Braido et al. |
| 9,226,825 B2 | 1/2016 | Starksen et al. |
| 9,226,839 B1 | 1/2016 | Kariniemi et al. |
| 9,232,995 B2 | 1/2016 | Kovalsky et al. |
| 9,241,790 B2 | 1/2016 | Lane et al. |
| 9,241,791 B2 | 1/2016 | Braido et al. |
| 9,241,792 B2 | 1/2016 | Benichou et al. |
| 9,241,794 B2 | 1/2016 | Braido et al. |
| 9,248,014 B2 | 2/2016 | Lane et al. |
| 9,265,608 B2 | 2/2016 | Miller et al. |
| 9,277,994 B2 | 3/2016 | Miller et al. |
| 9,289,290 B2 | 3/2016 | Alkhatib et al. |
| 9,289,291 B2 | 3/2016 | Gorman et al. |
| 9,295,550 B2 | 3/2016 | Nguyen et al. |
| 9,295,551 B2 | 3/2016 | Straubinger et al. |
| 9,295,552 B2 | 3/2016 | McLean et al. |
| 9,301,836 B2 | 4/2016 | Buchbinder et al. |
| 9,308,087 B2 | 4/2016 | Lane et al. |
| 9,320,591 B2 | 4/2016 | Bolduc |
| D755,384 S | 5/2016 | Pesce et al. |
| 9,326,852 B2 | 5/2016 | Spenser |
| 9,326,876 B2 | 5/2016 | Acosta et al. |
| 9,345,573 B2 | 5/2016 | Nyuli et al. |
| 9,351,830 B2 | 5/2016 | Gross et al. |
| 9,358,107 B2 | 6/2016 | Nguyen et al. |
| 9,387,078 B2 | 7/2016 | Gross et al. |
| 9,393,110 B2 | 7/2016 | Levi et al. |
| 9,393,111 B2 | 7/2016 | Ma et al. |
| 9,421,098 B2 | 8/2016 | Gifford et al. |
| 9,427,303 B2 | 8/2016 | Liddy et al. |
| 9,427,316 B2 | 8/2016 | Schweich, Jr. et al. |
| 9,439,757 B2 | 9/2016 | Wallace et al. |
| 9,445,893 B2 | 9/2016 | Vaturi |
| 9,463,102 B2 | 10/2016 | Kelly |
| 9,474,599 B2 | 10/2016 | Keränen |
| 9,474,638 B2 | 10/2016 | Robinson et al. |
| 9,480,559 B2 | 11/2016 | Vidlund et al. |
| 9,492,273 B2 | 11/2016 | Wallace et al. |
| 9,498,314 B2 | 11/2016 | Behan |
| 9,498,332 B2 | 11/2016 | Hacohen et al. |
| 9,510,947 B2 | 12/2016 | Straubinger et al. |
| 9,532,870 B2 | 1/2017 | Cooper et al. |
| 9,554,897 B2 | 1/2017 | Lane et al. |

(56) References Cited

U.S. PATENT DOCUMENTS

| | | | |
|---|---|---|---|
| 9,554,899 B2 | 1/2017 | Granada et al. |
| 9,561,103 B2 | 2/2017 | Granada et al. |
| 9,566,152 B2 | 2/2017 | Schweich et al. |
| 9,572,665 B2 | 2/2017 | Lane et al. |
| 9,597,182 B2 | 3/2017 | Straubinger et al. |
| 9,629,716 B2 | 4/2017 | Seguin |
| 9,662,203 B2 | 5/2017 | Sheahan et al. |
| 9,681,952 B2 | 6/2017 | Hacohen et al. |
| 9,717,591 B2 | 8/2017 | Chau et al. |
| 9,743,932 B2 | 8/2017 | Amplatz et al. |
| 9,763,657 B2 | 9/2017 | Hacohen et al. |
| 9,763,817 B2 | 9/2017 | Roeder |
| 9,770,256 B2 | 9/2017 | Cohen et al. |
| D800,908 S | 10/2017 | Hariton et al. |
| 9,788,941 B2 | 10/2017 | Hacohen |
| 9,895,226 B1 | 2/2018 | Harari et al. |
| 9,901,443 B2 | 2/2018 | Morriss et al. |
| 9,974,651 B2 | 5/2018 | Hariton et al. |
| 9,987,132 B1 | 6/2018 | Hariton et al. |
| 9,993,360 B2 | 6/2018 | Shalev et al. |
| 10,010,414 B2 | 7/2018 | Cooper et al. |
| 10,039,638 B2 | 8/2018 | Bruchman et al. |
| 10,045,845 B2 | 8/2018 | Hacohen et al. |
| 10,076,415 B1 | 9/2018 | Metchik et al. |
| 10,098,732 B1 | 10/2018 | Hariton et al. |
| 10,105,222 B1 | 10/2018 | Metchik et al. |
| 10,111,751 B1 | 10/2018 | Metchik et al. |
| 10,117,744 B2 | 11/2018 | Ratz et al. |
| 10,123,873 B1 | 11/2018 | Metchik et al. |
| 10,130,475 B1 | 11/2018 | Metchik et al. |
| 10,136,993 B1 | 11/2018 | Metchik et al. |
| 10,143,552 B2 | 12/2018 | Wallace et al. |
| 10,149,761 B2 | 12/2018 | Granada et al. |
| 10,154,903 B2 | 12/2018 | Albitov et al. |
| 10,154,906 B2 | 12/2018 | Granada et al. |
| 10,159,570 B1 | 12/2018 | Metchik et al. |
| 10,182,908 B2 | 1/2019 | Tubishevitz et al. |
| 10,206,668 B2 | 2/2019 | Mcgoldrick et al. |
| 10,226,341 B2 | 3/2019 | Gross et al. |
| 10,231,831 B2 | 3/2019 | Hacohen |
| 10,231,837 B1 | 3/2019 | Metchik et al. |
| 10,238,493 B1 | 3/2019 | Metchik et al. |
| 10,245,143 B2 | 4/2019 | Gross et al. |
| 10,245,144 B1 | 4/2019 | Metchik et al. |
| 10,258,471 B2 | 4/2019 | Lutter et al. |
| 10,292,816 B2 | 5/2019 | Raanani et al. |
| 10,299,927 B2 | 5/2019 | McLean et al. |
| 10,321,995 B1 | 6/2019 | Christianson et al. |
| 10,322,020 B2 | 6/2019 | Lam et al. |
| 10,327,895 B2 | 6/2019 | Lozonschi et al. |
| 10,335,278 B2 | 7/2019 | McLean et al. |
| 10,350,062 B2 | 7/2019 | Peterson et al. |
| 10,357,360 B2 | 7/2019 | Hariton et al. |
| 10,368,988 B2 | 8/2019 | Jones |
| 10,376,361 B2 | 8/2019 | Gross et al. |
| 10,390,952 B2 | 8/2019 | Hariton et al. |
| 10,426,610 B2 | 10/2019 | Hariton et al. |
| 10,426,614 B2 | 10/2019 | Hariton et al. |
| 10,449,047 B2 | 10/2019 | Hariton et al. |
| 10,456,256 B2 | 10/2019 | Braido et al. |
| 10,463,487 B2 | 11/2019 | Hariton et al. |
| 10,463,488 B2 | 11/2019 | Hariton et al. |
| 10,492,907 B2 | 12/2019 | Duffy |
| 10,492,908 B2 | 12/2019 | Hammer et al. |
| 10,507,105 B2 | 12/2019 | Hariton et al. |
| 10,507,108 B2 | 12/2019 | Delgado et al. |
| 10,507,109 B2 | 12/2019 | Metchik et al. |
| 10,512,456 B2 | 12/2019 | Hacohen et al. |
| 10,517,719 B2 | 12/2019 | Miller et al. |
| 10,524,792 B2 | 1/2020 | Hernandez et al. |
| 10,524,903 B2 | 1/2020 | Hariton et al. |
| 10,524,910 B2 | 1/2020 | Hammer et al. |
| 10,531,866 B2 | 1/2020 | Hariton et al. |
| 10,531,872 B2 | 1/2020 | Hacohen et al. |
| 10,537,426 B2 | 1/2020 | Iamberger et al. |
| 10,548,726 B2 | 2/2020 | Hacohen et al. |
| 10,548,731 B2 | 2/2020 | Lashinski et al. |
| 10,575,948 B2 | 3/2020 | Iamberger et al. |
| 10,595,992 B2 | 3/2020 | Chambers |
| 10,595,997 B2 | 3/2020 | Metchik et al. |
| 10,610,358 B2 | 4/2020 | Vidlund et al. |
| 10,610,359 B2 | 4/2020 | Hacohen |
| 10,631,871 B2 | 4/2020 | Goldfarb et al. |
| 10,631,982 B2 | 4/2020 | Hammer et al. |
| 10,631,984 B2 | 4/2020 | Nyuli et al. |
| 10,646,342 B1 | 5/2020 | Marr et al. |
| 10,660,751 B2 | 5/2020 | Hacohen |
| 10,667,908 B2 | 6/2020 | Hariton et al. |
| 10,667,912 B2 | 6/2020 | Dixon et al. |
| 10,682,227 B2 | 6/2020 | Hariton et al. |
| 10,695,173 B2 | 6/2020 | Gross et al. |
| 10,695,177 B2 | 6/2020 | Hariton et al. |
| 10,702,385 B2 | 7/2020 | Hacohen |
| 10,722,354 B2 | 7/2020 | Cohen-Tzemach et al. |
| 10,722,360 B2 | 7/2020 | Hariton et al. |
| 10,736,742 B2 | 8/2020 | Hariton et al. |
| 10,758,342 B2 | 9/2020 | Chau et al. |
| 10,758,344 B2 | 9/2020 | Hariton et al. |
| 10,779,939 B2 | 9/2020 | Hariton et al. |
| 10,799,345 B2 | 10/2020 | Hariton et al. |
| 10,813,760 B2 | 10/2020 | Metchik et al. |
| 10,820,998 B2 | 11/2020 | Marr et al. |
| 10,835,377 B2 | 11/2020 | Hacohen et al. |
| 10,842,627 B2 | 11/2020 | Delgado et al. |
| 10,849,748 B2 | 12/2020 | Hariton et al. |
| 10,856,972 B2 | 12/2020 | Hariton et al. |
| 10,856,975 B2 | 12/2020 | Hariton et al. |
| 10,856,978 B2 | 12/2020 | Straubinger et al. |
| 10,864,078 B2 | 12/2020 | Hariton et al. |
| 10,874,514 B2 | 12/2020 | Dixon et al. |
| 10,881,511 B2 | 1/2021 | Hariton et al. |
| 10,888,422 B2 | 1/2021 | Hariton et al. |
| 10,888,425 B2 | 1/2021 | Delgado et al. |
| 10,888,644 B2 | 1/2021 | Ratz et al. |
| 10,905,548 B2 | 2/2021 | Hariton et al. |
| 10,905,549 B2 | 2/2021 | Hariton et al. |
| 10,905,552 B2 | 2/2021 | Dixon et al. |
| 10,905,554 B2 | 2/2021 | Cao |
| 10,918,481 B2 | 2/2021 | Hariton et al. |
| 10,918,483 B2 | 2/2021 | Metchik et al. |
| 10,925,595 B2 | 2/2021 | Hacohen et al. |
| 10,925,732 B2 | 2/2021 | Delgado et al. |
| 10,945,843 B2 | 3/2021 | Delgado et al. |
| 10,945,844 B2 | 3/2021 | McCann et al. |
| 10,952,850 B2 | 3/2021 | Hariton et al. |
| 10,959,846 B2 | 3/2021 | Marr et al. |
| 10,973,636 B2 | 4/2021 | Hariton et al. |
| 10,993,809 B2 | 5/2021 | McCann et al. |
| 11,065,114 B2 | 7/2021 | Raanani et al. |
| 11,065,117 B2 | 7/2021 | Zeng |
| 11,083,582 B2 | 8/2021 | McCann et al. |
| 11,135,059 B2 | 10/2021 | Hammer et al. |
| 11,147,672 B2 | 10/2021 | McCann et al. |
| 11,179,240 B2 | 11/2021 | Delgado et al. |
| 11,246,704 B2 | 2/2022 | Hariton et al. |
| 11,291,545 B2 | 4/2022 | Hacohen |
| 11,291,546 B2 | 4/2022 | Gross et al. |
| 11,291,547 B2 | 4/2022 | Gross et al. |
| 11,304,804 B2 | 4/2022 | Hariton et al. |
| 11,304,805 B2 | 4/2022 | Hariton et al. |
| 11,304,806 B2 | 4/2022 | Hariton et al. |
| 11,318,014 B2 | 5/2022 | Hariton et al. |
| 11,318,015 B2 | 5/2022 | Hariton et al. |
| 11,337,802 B2 | 5/2022 | Hariton et al. |
| 11,337,803 B2 | 5/2022 | Hariton et al. |
| 11,337,804 B2 | 5/2022 | Hariton et al. |
| 11,389,297 B2 | 7/2022 | Franklin et al. |
| 2001/0002445 A1 | 5/2001 | Vesely |
| 2001/0005787 A1 | 6/2001 | Oz et al. |
| 2001/0021872 A1 | 9/2001 | Bailey et al. |
| 2001/0021874 A1 | 9/2001 | Carpentier et al. |
| 2001/0044656 A1 | 11/2001 | Williamson et al. |
| 2001/0056295 A1 | 12/2001 | Solem |
| 2002/0013571 A1 | 1/2002 | Goldfarb et al. |

(56) References Cited

U.S. PATENT DOCUMENTS

| | | |
|---|---|---|
| 2002/0022862 A1 | 2/2002 | Grafton et al. |
| 2002/0029080 A1 | 3/2002 | Mortier et al. |
| 2002/0032481 A1 | 3/2002 | Gabbay |
| 2002/0042621 A1 | 4/2002 | Liddicoat et al. |
| 2002/0082525 A1 | 6/2002 | Oslund et al. |
| 2002/0087048 A1 | 7/2002 | Brock et al. |
| 2002/0099436 A1 | 7/2002 | Thornton et al. |
| 2002/0103532 A1 | 8/2002 | Langberg et al. |
| 2002/0151916 A1 | 10/2002 | Muramatsu et al. |
| 2002/0151961 A1 | 10/2002 | Lashinski et al. |
| 2002/0151970 A1 | 10/2002 | Garrison et al. |
| 2002/0169358 A1 | 11/2002 | Mortier et al. |
| 2002/0173841 A1 | 11/2002 | Ortiz et al. |
| 2002/0177894 A1 | 11/2002 | Acosta et al. |
| 2002/0177904 A1 | 11/2002 | Huxel et al. |
| 2002/0198586 A1 | 12/2002 | Inoue |
| 2003/0009236 A1 | 1/2003 | Godin |
| 2003/0018358 A1 | 1/2003 | Saadat |
| 2003/0036791 A1 | 2/2003 | Philipp et al. |
| 2003/0050693 A1 | 3/2003 | Quijano et al. |
| 2003/0050694 A1 | 3/2003 | Yang et al. |
| 2003/0060846 A1 | 3/2003 | Egnelov et al. |
| 2003/0060875 A1 | 3/2003 | Wittens |
| 2003/0069635 A1 | 4/2003 | Cartledge |
| 2003/0074052 A1 | 4/2003 | Besselink |
| 2003/0074059 A1 | 4/2003 | Nguyen et al. |
| 2003/0078465 A1 | 4/2003 | Pai et al. |
| 2003/0078653 A1 | 4/2003 | Vesely et al. |
| 2003/0083742 A1 | 5/2003 | Spence et al. |
| 2003/0100943 A1 | 5/2003 | Bolduc |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0130731 A1 | 7/2003 | Vidlund et al. |
| 2003/0158578 A1 | 8/2003 | Pantages et al. |
| 2003/0167062 A1 | 9/2003 | Gambale et al. |
| 2003/0171760 A1 | 9/2003 | Gambale |
| 2003/0191528 A1 | 10/2003 | Quijano et al. |
| 2003/0199974 A1 | 10/2003 | Lee et al. |
| 2003/0204195 A1 | 10/2003 | Keane et al. |
| 2003/0229350 A1 | 12/2003 | Kay |
| 2003/0229395 A1 | 12/2003 | Cox |
| 2003/0233142 A1 | 12/2003 | Morales et al. |
| 2004/0010272 A1 | 1/2004 | Manetakis et al. |
| 2004/0019377 A1 | 1/2004 | Taylor et al. |
| 2004/0024451 A1 | 2/2004 | Johnson et al. |
| 2004/0030382 A1 | 2/2004 | St. Goar et al. |
| 2004/0039414 A1 | 2/2004 | Carley et al. |
| 2004/0039436 A1 | 2/2004 | Spenser et al. |
| 2004/0039442 A1 | 2/2004 | St. Goar et al. |
| 2004/0049207 A1 | 3/2004 | Goldfarb et al. |
| 2004/0059413 A1 | 3/2004 | Argento |
| 2004/0092962 A1 | 5/2004 | Thornton et al. |
| 2004/0093060 A1 | 5/2004 | Seguin et al. |
| 2004/0122448 A1 | 6/2004 | Levine |
| 2004/0122503 A1 | 6/2004 | Campbell et al. |
| 2004/0122514 A1 | 6/2004 | Fogarty et al. |
| 2004/0127982 A1 | 7/2004 | Machold et al. |
| 2004/0127983 A1 | 7/2004 | Mortier et al. |
| 2004/0133220 A1 | 7/2004 | Lashinski et al. |
| 2004/0133267 A1 | 7/2004 | Lane |
| 2004/0133274 A1 | 7/2004 | Webler et al. |
| 2004/0133374 A1 | 7/2004 | Kattan |
| 2004/0138744 A1 | 7/2004 | Lashinski et al. |
| 2004/0138745 A1 | 7/2004 | Macoviak et al. |
| 2004/0143315 A1 | 7/2004 | Bruun et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0153146 A1 | 8/2004 | Lashinski et al. |
| 2004/0172046 A1 | 9/2004 | Hlavka et al. |
| 2004/0176788 A1 | 9/2004 | Opolski |
| 2004/0176839 A1 | 9/2004 | Huynh et al. |
| 2004/0181287 A1 | 9/2004 | Gellman |
| 2004/0186558 A1 | 9/2004 | Pavcnik et al. |
| 2004/0186565 A1 | 9/2004 | Schreck |
| 2004/0186566 A1 | 9/2004 | Hindrichs et al. |
| 2004/0210244 A1 | 10/2004 | Vargas et al. |
| 2004/0210304 A1 | 10/2004 | Seguin et al. |
| 2004/0220593 A1 | 11/2004 | Greenhalgh |
| 2004/0225354 A1 | 11/2004 | Allen et al. |
| 2004/0236354 A1 | 11/2004 | Seguin |
| 2004/0236419 A1 | 11/2004 | Milo |
| 2004/0249433 A1 | 12/2004 | Freitag |
| 2004/0249453 A1 | 12/2004 | Cartledge et al. |
| 2004/0260317 A1 | 12/2004 | Bloom et al. |
| 2004/0260389 A1 | 12/2004 | Case et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0021056 A1 | 1/2005 | St. Goar et al. |
| 2005/0027305 A1 | 2/2005 | Shiu et al. |
| 2005/0027348 A1 | 2/2005 | Case et al. |
| 2005/0038494 A1 | 2/2005 | Eidenschink |
| 2005/0055038 A1 | 3/2005 | Kelleher et al. |
| 2005/0055086 A1 | 3/2005 | Stobie |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075726 A1 | 4/2005 | Svanidze et al. |
| 2005/0075727 A1 | 4/2005 | Wheatley |
| 2005/0075731 A1 | 4/2005 | Artof et al. |
| 2005/0080430 A1 | 4/2005 | Wright et al. |
| 2005/0080474 A1 | 4/2005 | Andreas et al. |
| 2005/0085900 A1 | 4/2005 | Case et al. |
| 2005/0085903 A1 | 4/2005 | Lau |
| 2005/0090827 A1 | 4/2005 | Gedebou |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137681 A1 | 6/2005 | Shoemaker et al. |
| 2005/0137686 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137695 A1 | 6/2005 | Salahieh et al. |
| 2005/0137697 A1 | 6/2005 | Salahieh et al. |
| 2005/0137699 A1 | 6/2005 | Salahieh et al. |
| 2005/0143809 A1 | 6/2005 | Salahieh et al. |
| 2005/0149160 A1 | 7/2005 | McFerran |
| 2005/0154443 A1 | 7/2005 | Linder et al. |
| 2005/0159728 A1 | 7/2005 | Armour et al. |
| 2005/0171601 A1 | 8/2005 | Cosgrove et al. |
| 2005/0177180 A1 | 8/2005 | Kaganov et al. |
| 2005/0177222 A1 | 8/2005 | Mead |
| 2005/0177228 A1 | 8/2005 | Solem et al. |
| 2005/0182483 A1 | 8/2005 | Osborne et al. |
| 2005/0182486 A1 | 8/2005 | Gabbay |
| 2005/0187613 A1 | 8/2005 | Bolduc et al. |
| 2005/0192596 A1 | 9/2005 | Jugenheimer et al. |
| 2005/0197695 A1 | 9/2005 | Stacchino et al. |
| 2005/0197696 A1 | 9/2005 | Gomez Duran |
| 2005/0203549 A1 | 9/2005 | Realyvasquez |
| 2005/0203606 A1 | 9/2005 | VanCamp |
| 2005/0203618 A1 | 9/2005 | Sharkawy et al. |
| 2005/0216039 A1 | 9/2005 | Lederman |
| 2005/0216079 A1 | 9/2005 | MaCoviak |
| 2005/0222665 A1 | 10/2005 | Aranyi |
| 2005/0222678 A1 | 10/2005 | Lashinski et al. |
| 2005/0234508 A1 | 10/2005 | Cummins et al. |
| 2005/0240200 A1 | 10/2005 | Bergheim |
| 2005/0251251 A1 | 11/2005 | Cribier |
| 2005/0256532 A1 | 11/2005 | Nayak et al. |

(56) References Cited

U.S. PATENT DOCUMENTS

| | | |
|---|---|---|
| 2005/0256566 A1 | 11/2005 | Gabbay |
| 2005/0267478 A1 | 12/2005 | Corradi et al. |
| 2005/0267573 A9 | 12/2005 | Macoviak et al. |
| 2005/0273138 A1 | 12/2005 | To et al. |
| 2005/0288776 A1 | 12/2005 | Shaoulian et al. |
| 2005/0288778 A1 | 12/2005 | Shaoulian et al. |
| 2005/0288781 A1 | 12/2005 | Moaddeb et al. |
| 2006/0004439 A1 | 1/2006 | Spenser et al. |
| 2006/0004442 A1 | 1/2006 | Spenser et al. |
| 2006/0004443 A1 | 1/2006 | Liddicoat et al. |
| 2006/0004469 A1 | 1/2006 | Sokel |
| 2006/0015171 A1 | 1/2006 | Armstrong |
| 2006/0020275 A1 | 1/2006 | Goldfarb et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025855 A1 | 2/2006 | Lashinski et al. |
| 2006/0025858 A1 | 2/2006 | Alameddine |
| 2006/0030885 A1 | 2/2006 | Hyde |
| 2006/0041189 A1 | 2/2006 | Vancaillie |
| 2006/0041319 A1 | 2/2006 | Taylor et al. |
| 2006/0047297 A1 | 3/2006 | Case |
| 2006/0052867 A1 | 3/2006 | Revuelta et al. |
| 2006/0052868 A1 | 3/2006 | Mortier |
| 2006/0058871 A1 | 3/2006 | Zakay et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0089627 A1 | 4/2006 | Burnett et al. |
| 2006/0095009 A1 | 5/2006 | Lampropoulos et al. |
| 2006/0106423 A1 | 5/2006 | Weisel et al. |
| 2006/0111773 A1 | 5/2006 | Rittgers et al. |
| 2006/0116750 A1 | 6/2006 | Herbert et al. |
| 2006/0116757 A1 | 6/2006 | Lashinski et al. |
| 2006/0122692 A1 | 6/2006 | Gilad et al. |
| 2006/0129166 A1 | 6/2006 | Lavelle |
| 2006/0135964 A1 | 6/2006 | Vesley |
| 2006/0149280 A1 | 7/2006 | Harvine et al. |
| 2006/0149360 A1 | 7/2006 | Schwammenthal et al. |
| 2006/0149368 A1 | 7/2006 | Spence |
| 2006/0155357 A1 | 7/2006 | Melsheimer |
| 2006/0161250 A1 | 7/2006 | Shaw |
| 2006/0161265 A1 | 7/2006 | Levine et al. |
| 2006/0178700 A1 | 8/2006 | Quinn |
| 2006/0178740 A1 | 8/2006 | Stacchino et al. |
| 2006/0184203 A1 | 8/2006 | Martin et al. |
| 2006/0184240 A1 | 8/2006 | Jimenez et al. |
| 2006/0184242 A1 | 8/2006 | Lichtenstein |
| 2006/0190036 A1 | 8/2006 | Wendel et al. |
| 2006/0190038 A1 | 8/2006 | Carley et al. |
| 2006/0195134 A1 | 8/2006 | Crittenden |
| 2006/0195183 A1 | 8/2006 | Navia et al. |
| 2006/0195184 A1 | 8/2006 | Lane et al. |
| 2006/0201519 A1 | 9/2006 | Frazier et al. |
| 2006/0212107 A1 | 9/2006 | Case et al. |
| 2006/0212111 A1 | 9/2006 | Case et al. |
| 2006/0216404 A1 | 9/2006 | Seyler et al. |
| 2006/0229708 A1 | 10/2006 | Powell et al. |
| 2006/0241622 A1 | 10/2006 | Zergiebel |
| 2006/0241656 A1 | 10/2006 | Starksen et al. |
| 2006/0241745 A1 | 10/2006 | Solem |
| 2006/0241748 A1 | 10/2006 | Lee et al. |
| 2006/0247680 A1 | 11/2006 | Amplatz et al. |
| 2006/0247763 A1 | 11/2006 | Slater |
| 2006/0253191 A1 | 11/2006 | Salahieh et al. |
| 2006/0259135 A1 | 11/2006 | Navia et al. |
| 2006/0259136 A1 | 11/2006 | Nguyen et al. |
| 2006/0259137 A1 | 11/2006 | Artof et al. |
| 2006/0271166 A1 | 11/2006 | Thill et al. |
| 2006/0271171 A1 | 11/2006 | McQuinn et al. |
| 2006/0271175 A1 | 11/2006 | Woolfson |
| 2006/0282150 A1 | 12/2006 | Olson et al. |
| 2006/0282161 A1 | 12/2006 | Huyn et al. |
| 2006/0287661 A1 | 12/2006 | Bolduc et al. |
| 2006/0287716 A1 | 12/2006 | Banbury et al. |
| 2006/0287719 A1 | 12/2006 | Rowe et al. |
| 2007/0001627 A1 | 1/2007 | Lin et al. |
| 2007/0008018 A1 | 1/2007 | Nagashima et al. |
| 2007/0016286 A1 | 1/2007 | Herrmann et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027528 A1 | 2/2007 | Agnew |
| 2007/0027533 A1 | 2/2007 | Douk |
| 2007/0027536 A1 | 2/2007 | Mihaljevic et al. |
| 2007/0027549 A1 | 2/2007 | Godin |
| 2007/0038221 A1 | 2/2007 | Fine et al. |
| 2007/0038293 A1 | 2/2007 | St. Goar et al. |
| 2007/0038295 A1 | 2/2007 | Case et al. |
| 2007/0043435 A1 | 2/2007 | Seguin et al. |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0055340 A1 | 3/2007 | Pryor |
| 2007/0056346 A1 | 3/2007 | Spenser et al. |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0078510 A1 | 4/2007 | Ryan |
| 2007/0080188 A1 | 4/2007 | Spence et al. |
| 2007/0083168 A1 | 4/2007 | Whiting et al. |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0173932 A1 | 7/2007 | Cali et al. |
| 2007/0197858 A1 | 8/2007 | Goldfarb et al. |
| 2007/0198077 A1 | 8/2007 | Cully et al. |
| 2007/0198082 A1 | 8/2007 | Kapadia et al. |
| 2007/0198097 A1 | 8/2007 | Zegdi |
| 2007/0208550 A1 | 9/2007 | Cao et al. |
| 2007/0213582 A1 | 9/2007 | Zollinger et al. |
| 2007/0213810 A1 | 9/2007 | Newhauser et al. |
| 2007/0213813 A1 | 9/2007 | Von Segesser et al. |
| 2007/0219558 A1 | 9/2007 | Deutsch |
| 2007/0219630 A1 | 9/2007 | Chu |
| 2007/0225759 A1 | 9/2007 | Thommen et al. |
| 2007/0225760 A1 | 9/2007 | Moszner et al. |
| 2007/0233186 A1 | 10/2007 | Meng |
| 2007/0233237 A1 | 10/2007 | Krivoruchko |
| 2007/0233239 A1 | 10/2007 | Navia et al. |
| 2007/0239208 A1 | 10/2007 | Crawford |
| 2007/0239265 A1 | 10/2007 | Birdsall et al. |
| 2007/0239272 A1 | 10/2007 | Navia et al. |
| 2007/0239273 A1 | 10/2007 | Allen |
| 2007/0244546 A1 | 10/2007 | Francis |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255397 A1 | 11/2007 | Ryan et al. |
| 2007/0255400 A1 | 11/2007 | Parravicini et al. |
| 2007/0270755 A1 | 11/2007 | Von Oepen et al. |
| 2007/0270943 A1 | 11/2007 | Solem et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2007/0299424 A1 | 12/2007 | Cumming et al. |
| 2008/0004688 A1 | 1/2008 | Spenser et al. |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |

(56)                References Cited

U.S. PATENT DOCUMENTS

| 2008/0035160 A1 | 2/2008 | Woodson et al. |
| 2008/0039935 A1 | 2/2008 | Buch |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Macoviak et al. |
| 2008/0071361 A1 | 3/2008 | Tuval et al. |
| 2008/0071363 A1 | 3/2008 | Tuval et al. |
| 2008/0071366 A1 | 3/2008 | Tuval et al. |
| 2008/0071369 A1 | 3/2008 | Tuval et al. |
| 2008/0077235 A1 | 3/2008 | Kirson |
| 2008/0082083 A1 | 4/2008 | Forde et al. |
| 2008/0082159 A1 | 4/2008 | Tseng et al. |
| 2008/0082166 A1 | 4/2008 | Styrc et al. |
| 2008/0086138 A1 | 4/2008 | Stone et al. |
| 2008/0086164 A1 | 4/2008 | Rowe et al. |
| 2008/0086203 A1 | 4/2008 | Roberts |
| 2008/0086204 A1 | 4/2008 | Rankin |
| 2008/0091257 A1 | 4/2008 | Andreas et al. |
| 2008/0091261 A1 | 4/2008 | Long et al. |
| 2008/0097523 A1 | 4/2008 | Bolduc et al. |
| 2008/0097595 A1 | 4/2008 | Gabbay |
| 2008/0103581 A1 | 5/2008 | Goto |
| 2008/0132989 A1 | 6/2008 | Snow et al. |
| 2008/0140003 A1 | 6/2008 | Bei et al. |
| 2008/0140116 A1 | 6/2008 | Bonutti |
| 2008/0147182 A1 | 6/2008 | Righini et al. |
| 2008/0161910 A1 | 7/2008 | Revuelta et al. |
| 2008/0167705 A1 | 7/2008 | Agnew |
| 2008/0167714 A1 | 7/2008 | St. Goar et al. |
| 2008/0188929 A1 | 8/2008 | Schreck |
| 2008/0195126 A1 | 8/2008 | Solem |
| 2008/0195200 A1 | 8/2008 | Vidlund et al. |
| 2008/0200980 A1 | 8/2008 | Robin et al. |
| 2008/0208265 A1 | 8/2008 | Frazier et al. |
| 2008/0208328 A1 | 8/2008 | Antocci et al. |
| 2008/0208330 A1 | 8/2008 | Keranen |
| 2008/0208332 A1 | 8/2008 | Lamphere et al. |
| 2008/0221672 A1 | 9/2008 | Lamphere et al. |
| 2008/0234814 A1 | 9/2008 | Salahieh et al. |
| 2008/0243245 A1 | 10/2008 | Thambar et al. |
| 2008/0255580 A1 | 10/2008 | Hoffman et al. |
| 2008/0262609 A1 | 10/2008 | Gross et al. |
| 2008/0269879 A1 | 10/2008 | Sathe et al. |
| 2008/0275300 A1 | 11/2008 | Rothe et al. |
| 2008/0275469 A1 | 11/2008 | Fanton et al. |
| 2008/0275551 A1 | 11/2008 | Alfieri |
| 2008/0281411 A1 | 11/2008 | Berreklouw |
| 2008/0288044 A1 | 11/2008 | Osborne |
| 2008/0288062 A1 | 11/2008 | Andrieu et al. |
| 2008/0294234 A1 | 11/2008 | Hartley et al. |
| 2008/0300629 A1 | 12/2008 | Surti |
| 2009/0005863 A1 | 1/2009 | Goetz et al. |
| 2009/0036966 A1 | 2/2009 | O'Connor et al. |
| 2009/0036977 A1 | 2/2009 | Rassat et al. |
| 2009/0043153 A1 | 2/2009 | Zollinger et al. |
| 2009/0043381 A1 | 2/2009 | Macoviak et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |
| 2009/0082844 A1 | 3/2009 | Zacharias et al. |
| 2009/0088836 A1 | 4/2009 | Bishop et al. |
| 2009/0088837 A1 | 4/2009 | Gillinov et al. |
| 2009/0099554 A1 | 4/2009 | Forster et al. |
| 2009/0099650 A1 | 4/2009 | Bolduc et al. |
| 2009/0099653 A1 | 4/2009 | Suri et al. |
| 2009/0105794 A1 | 4/2009 | Ziarno et al. |
| 2009/0105816 A1 | 4/2009 | Olsen et al. |
| 2009/0112159 A1 | 4/2009 | Slattery et al. |
| 2009/0125098 A1 | 5/2009 | Chuter |
| 2009/0125102 A1 | 5/2009 | Cartledge |
| 2009/0149872 A1 | 6/2009 | Gross et al. |
| 2009/0157175 A1 | 6/2009 | Benichou |
| 2009/0163934 A1 | 6/2009 | Raschdorf, Jr. et al. |
| 2009/0171363 A1 | 7/2009 | Chocron |
| 2009/0171439 A1 | 7/2009 | Nissl |
| 2009/0177266 A1 | 7/2009 | Powell et al. |
| 2009/0177274 A1 | 7/2009 | Scorsin et al. |
| 2009/0177277 A1 | 7/2009 | Milo |
| 2009/0177278 A1 | 7/2009 | Spence |
| 2009/0192601 A1 | 7/2009 | Rafiee et al. |
| 2009/0210052 A1 | 8/2009 | Forster et al. |
| 2009/0222081 A1 | 9/2009 | Linder et al. |
| 2009/0240320 A1 | 9/2009 | Tuval et al. |
| 2009/0241656 A1 | 10/2009 | Jacquemin |
| 2009/0248143 A1 | 10/2009 | Laham |
| 2009/0248148 A1 | 10/2009 | Shaolian et al. |
| 2009/0254103 A1 | 10/2009 | Deustch |
| 2009/0259306 A1 | 10/2009 | Rowe |
| 2009/0259307 A1 | 10/2009 | Gross et al. |
| 2009/0264859 A1 | 10/2009 | Mas |
| 2009/0264994 A1 | 10/2009 | Saadat |
| 2009/0264995 A1 | 10/2009 | Subramanian |
| 2009/0276040 A1 | 11/2009 | Rowe et al. |
| 2009/0281619 A1 | 11/2009 | Le et al. |
| 2009/0287299 A1 | 11/2009 | Tabor et al. |
| 2009/0287304 A1 | 11/2009 | Dahlgren et al. |
| 2009/0299409 A1 | 12/2009 | Coe et al. |
| 2009/0299449 A1 | 12/2009 | Styrc |
| 2009/0306768 A1 | 12/2009 | Quardi |
| 2009/0319037 A1 | 12/2009 | Rowe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0022823 A1 | 1/2010 | Goldfarb et al. |
| 2010/0023117 A1 | 1/2010 | Yoganathan et al. |
| 2010/0023118 A1 | 1/2010 | Medlock et al. |
| 2010/0023120 A1 | 1/2010 | Holecek et al. |
| 2010/0030014 A1 | 2/2010 | Ferrazzi |
| 2010/0036479 A1 | 2/2010 | Hill et al. |
| 2010/0036484 A1 | 2/2010 | Hariton et al. |
| 2010/0042147 A1 | 2/2010 | Janovsky et al. |
| 2010/0049306 A1 | 2/2010 | House et al. |
| 2010/0049313 A1 | 2/2010 | Alon et al. |
| 2010/0063542 A1 | 3/2010 | Van der Burg et al. |
| 2010/0063550 A1 | 3/2010 | Felix et al. |
| 2010/0063586 A1 | 3/2010 | Hasenkam et al. |
| 2010/0069852 A1 | 3/2010 | Kelley |
| 2010/0076499 A1 | 3/2010 | McNamara et al. |
| 2010/0076548 A1 | 3/2010 | Konno |
| 2010/0082094 A1 | 4/2010 | Quadri et al. |
| 2010/0094248 A1 | 4/2010 | Nguyen et al. |
| 2010/0100167 A1 | 4/2010 | Bortlein et al. |
| 2010/0114180 A1 | 5/2010 | Rock |
| 2010/0114299 A1 | 5/2010 | Ben-Muvhar et al. |
| 2010/0121349 A1 | 5/2010 | Meier |
| 2010/0130992 A1 | 5/2010 | Machold et al. |
| 2010/0131054 A1 | 5/2010 | Tuval et al. |
| 2010/0137979 A1 | 6/2010 | Tuval et al. |
| 2010/0152845 A1 | 6/2010 | Bloom et al. |
| 2010/0160958 A1 | 6/2010 | Clark |
| 2010/0161036 A1 | 6/2010 | Pintor et al. |
| 2010/0161041 A1 | 6/2010 | Maisano et al. |
| 2010/0161042 A1 | 6/2010 | Maisano et al. |
| 2010/0161043 A1 | 6/2010 | Maisano et al. |
| 2010/0161047 A1 | 6/2010 | Cabiri |
| 2010/0168845 A1 | 7/2010 | Wright |
| 2010/0174358 A1 | 7/2010 | Rabkin et al. |
| 2010/0174363 A1 | 7/2010 | Castro |
| 2010/0179574 A1 | 7/2010 | Longoria et al. |
| 2010/0179643 A1 | 7/2010 | Shalev |
| 2010/0179648 A1 | 7/2010 | Richter et al. |
| 2010/0179649 A1 | 7/2010 | Richter et al. |
| 2010/0185277 A1 | 7/2010 | Braido et al. |
| 2010/0198347 A1 | 8/2010 | Zakay et al. |
| 2010/0217382 A1 | 8/2010 | Chau et al. |
| 2010/0222810 A1 | 9/2010 | DeBeer et al. |
| 2010/0228285 A1 | 9/2010 | Miles et al. |
| 2010/0234935 A1 | 9/2010 | Bashiri et al. |
| 2010/0234940 A1 | 9/2010 | Dolan |
| 2010/0249908 A1 | 9/2010 | Chau et al. |
| 2010/0249915 A1 | 9/2010 | Zhang |
| 2010/0249917 A1 | 9/2010 | Zhang |

(56)                References Cited

U.S. PATENT DOCUMENTS

| | | |
|---|---|---|
| 2010/0249920 A1 | 9/2010 | Bolling et al. |
| 2010/0256737 A1 | 10/2010 | Pollock et al. |
| 2010/0262232 A1 | 10/2010 | Annest |
| 2010/0262233 A1 | 10/2010 | He |
| 2010/0280603 A1 | 11/2010 | Maisano et al. |
| 2010/0280604 A1 | 11/2010 | Zipory et al. |
| 2010/0280605 A1 | 11/2010 | Hammer et al. |
| 2010/0280606 A1 | 11/2010 | Naor |
| 2010/0286628 A1 | 11/2010 | Gross |
| 2010/0286767 A1 | 11/2010 | Zipory et al. |
| 2010/0305475 A1 | 12/2010 | Hinchliffe et al. |
| 2010/0312333 A1 | 12/2010 | Navia et al. |
| 2010/0324595 A1 | 12/2010 | Linder et al. |
| 2010/0331971 A1 | 12/2010 | Keränen et al. |
| 2011/0004210 A1 | 1/2011 | Johnson et al. |
| 2011/0004227 A1 | 1/2011 | Goldfarb et al. |
| 2011/0004296 A1 | 1/2011 | Lutter et al. |
| 2011/0004298 A1 | 1/2011 | Lee et al. |
| 2011/0004299 A1 | 1/2011 | Navia et al. |
| 2011/0011917 A1 | 1/2011 | Loulmet |
| 2011/0015729 A1 | 1/2011 | Jimenez et al. |
| 2011/0015731 A1 | 1/2011 | Carpentier et al. |
| 2011/0015739 A1 | 1/2011 | Cheung et al. |
| 2011/0021985 A1 | 1/2011 | Spargias |
| 2011/0022165 A1 | 1/2011 | Oba et al. |
| 2011/0026208 A1 | 2/2011 | Otsuro et al. |
| 2011/0029066 A1 | 2/2011 | Gilad et al. |
| 2011/0029067 A1 | 2/2011 | Mcguckin, Jr. et al. |
| 2011/0029072 A1 | 2/2011 | Gabbay |
| 2011/0035000 A1 | 2/2011 | Nieminen et al. |
| 2011/0040374 A1 | 2/2011 | Goetz et al. |
| 2011/0040375 A1 | 2/2011 | Letac et al. |
| 2011/0046662 A1 | 2/2011 | Moszner et al. |
| 2011/0054466 A1 | 3/2011 | Rothstein et al. |
| 2011/0054596 A1 | 3/2011 | Taylor |
| 2011/0054598 A1 | 3/2011 | Johnson |
| 2011/0066231 A1 | 3/2011 | Cartledge et al. |
| 2011/0066233 A1 | 3/2011 | Thornton et al. |
| 2011/0067770 A1 | 3/2011 | Pederson et al. |
| 2011/0071626 A1 | 3/2011 | Wright et al. |
| 2011/0077730 A1 | 3/2011 | Fentster |
| 2011/0082538 A1 | 4/2011 | Dahlgren et al. |
| 2011/0087146 A1 | 4/2011 | Ryan et al. |
| 2011/0087322 A1 | 4/2011 | Letac et al. |
| 2011/0093002 A1 | 4/2011 | Rucker et al. |
| 2011/0093063 A1 | 4/2011 | Schreck |
| 2011/0098525 A1 | 4/2011 | Kermode et al. |
| 2011/0098802 A1 | 4/2011 | Braido et al. |
| 2011/0098805 A1 | 4/2011 | Dwork et al. |
| 2011/0106245 A1 | 5/2011 | Miller et al. |
| 2011/0106247 A1 | 5/2011 | Miller et al. |
| 2011/0112625 A1 | 5/2011 | Ben-Muvhar et al. |
| 2011/0112632 A1 | 5/2011 | Chau et al. |
| 2011/0113768 A1 | 5/2011 | Bauer et al. |
| 2011/0118830 A1 | 5/2011 | Liddicoat et al. |
| 2011/0118832 A1 | 5/2011 | Punjabi |
| 2011/0125257 A1 | 5/2011 | Seguin et al. |
| 2011/0125258 A1 | 5/2011 | Centola |
| 2011/0137326 A1 | 6/2011 | Bachman |
| 2011/0137397 A1 | 6/2011 | Chau et al. |
| 2011/0137409 A1 | 6/2011 | Yang et al. |
| 2011/0137410 A1 | 6/2011 | Hacohen |
| 2011/0144703 A1 | 6/2011 | Krause et al. |
| 2011/0144742 A1 | 6/2011 | Madrid et al. |
| 2011/0166636 A1 | 7/2011 | Rowe |
| 2011/0166649 A1 | 7/2011 | Gross et al. |
| 2011/0172784 A1 | 7/2011 | Richter |
| 2011/0178597 A9 | 7/2011 | Navia et al. |
| 2011/0184510 A1 | 7/2011 | Maisano et al. |
| 2011/0190877 A1 | 8/2011 | Lane et al. |
| 2011/0190879 A1 | 8/2011 | Bobo et al. |
| 2011/0202076 A1 | 8/2011 | Richter |
| 2011/0202130 A1 | 8/2011 | Cartledge et al. |
| 2011/0208283 A1 | 8/2011 | Rust |
| 2011/0208293 A1 | 8/2011 | Tabor |
| 2011/0208298 A1 | 8/2011 | Tuval et al. |
| 2011/0213459 A1 | 9/2011 | Garrison et al. |
| 2011/0213461 A1 | 9/2011 | Seguin et al. |
| 2011/0218619 A1 | 9/2011 | Benichou et al. |
| 2011/0218620 A1 | 9/2011 | Meiri et al. |
| 2011/0224785 A1 | 9/2011 | Hacohen |
| 2011/0230941 A1 | 9/2011 | Markus |
| 2011/0230961 A1 | 9/2011 | Langer et al. |
| 2011/0238088 A1 | 9/2011 | Bodluc et al. |
| 2011/0238094 A1 | 9/2011 | Thomas et al. |
| 2011/0238159 A1 | 9/2011 | Guyenot et al. |
| 2011/0245911 A1 | 10/2011 | Quill et al. |
| 2011/0245917 A1 | 10/2011 | Savage et al. |
| 2011/0251675 A1 | 10/2011 | Dwork |
| 2011/0251676 A1 | 10/2011 | Sweeney et al. |
| 2011/0251678 A1 | 10/2011 | Eidenschink et al. |
| 2011/0251679 A1 | 10/2011 | Weimeyer et al. |
| 2011/0251680 A1 | 10/2011 | Tran et al. |
| 2011/0251682 A1 | 10/2011 | Murray, III et al. |
| 2011/0251683 A1 | 10/2011 | Tabor |
| 2011/0257433 A1 | 10/2011 | Walker |
| 2011/0257633 A1 | 10/2011 | Cartledge et al. |
| 2011/0257721 A1 | 10/2011 | Tabor |
| 2011/0257728 A1 | 10/2011 | Kuehn |
| 2011/0257729 A1 | 10/2011 | Spenser et al. |
| 2011/0257736 A1 | 10/2011 | Marquez et al. |
| 2011/0257737 A1 | 10/2011 | Fogarty et al. |
| 2011/0264191 A1 | 10/2011 | Rothstein |
| 2011/0264196 A1 | 10/2011 | Savage et al. |
| 2011/0264198 A1 | 10/2011 | Murray, III et al. |
| 2011/0264199 A1 | 10/2011 | Tran et al. |
| 2011/0264200 A1 | 10/2011 | Tran et al. |
| 2011/0264201 A1 | 10/2011 | Yeung |
| 2011/0264202 A1 | 10/2011 | Murray, III et al. |
| 2011/0264203 A1 | 10/2011 | Dwork et al. |
| 2011/0264206 A1 | 10/2011 | Tabor |
| 2011/0264208 A1 | 10/2011 | Duffy |
| 2011/0270276 A1 | 11/2011 | Rothstein et al. |
| 2011/0271967 A1 | 11/2011 | Mortier et al. |
| 2011/0276062 A1 | 11/2011 | Bolduc |
| 2011/0282361 A1 | 11/2011 | Miller et al. |
| 2011/0282438 A1 | 11/2011 | Drews et al. |
| 2011/0282439 A1 | 11/2011 | Thill et al. |
| 2011/0282440 A1 | 11/2011 | Cao |
| 2011/0283514 A1 | 11/2011 | Fogarty et al. |
| 2011/0288435 A1 | 11/2011 | Christy et al. |
| 2011/0288632 A1 | 11/2011 | White |
| 2011/0288634 A1 | 11/2011 | Tuval et al. |
| 2011/0288635 A1 | 11/2011 | Miller et al. |
| 2011/0295354 A1 | 12/2011 | Bueche et al. |
| 2011/0295363 A1 | 12/2011 | Girard et al. |
| 2011/0301498 A1 | 12/2011 | Maenhout et al. |
| 2011/0301688 A1 | 12/2011 | Dolan |
| 2011/0301698 A1 | 12/2011 | Miller et al. |
| 2011/0301701 A1 | 12/2011 | Padala et al. |
| 2011/0301702 A1 | 12/2011 | Rust et al. |
| 2011/0306916 A1 | 12/2011 | Nitzan et al. |
| 2011/0307049 A1 | 12/2011 | Kao |
| 2011/0313452 A1 | 12/2011 | Carley et al. |
| 2011/0313515 A1 | 12/2011 | Quadri et al. |
| 2011/0319989 A1 | 12/2011 | Lane et al. |
| 2011/0319991 A1 | 12/2011 | Hariton et al. |
| 2012/0010694 A1 | 1/2012 | Lutter et al. |
| 2012/0016468 A1 | 1/2012 | Robin et al. |
| 2012/0022557 A1 | 1/2012 | Cabiri et al. |
| 2012/0022629 A1 | 1/2012 | Perera et al. |
| 2012/0022633 A1 | 1/2012 | Olson et al. |
| 2012/0022637 A1 | 1/2012 | Ben-Movhar et al. |
| 2012/0022639 A1 | 1/2012 | Hacohen et al. |
| 2012/0022640 A1 | 1/2012 | Gross et al. |
| 2012/0022644 A1 | 1/2012 | Reich et al. |
| 2012/0035703 A1 | 2/2012 | Lutter et al. |
| 2012/0035712 A1 | 2/2012 | Maisano et al. |
| 2012/0035713 A1 | 2/2012 | Lutter et al. |
| 2012/0035722 A1 | 2/2012 | Tuval et al. |
| 2012/0041547 A1 | 2/2012 | Duffy et al. |
| 2012/0041551 A1 | 2/2012 | Spenser et al. |
| 2012/0046738 A1 | 2/2012 | Lau et al. |
| 2012/0046742 A1 | 2/2012 | Tuval et al. |

(56)         References Cited

U.S. PATENT DOCUMENTS

| | | |
|---|---|---|
| 2012/0053676 A1 | 3/2012 | Ku et al. |
| 2012/0053680 A1 | 3/2012 | Bolling et al. |
| 2012/0053682 A1 | 3/2012 | Kovalsky et al. |
| 2012/0053688 A1 | 3/2012 | Fogarty et al. |
| 2012/0059337 A1 | 3/2012 | Eilat |
| 2012/0059454 A1 | 3/2012 | Millwee et al. |
| 2012/0059458 A1 | 3/2012 | Buchbinder et al. |
| 2012/0065464 A1 | 3/2012 | Ellis et al. |
| 2012/0078237 A1 | 3/2012 | Wang et al. |
| 2012/0078353 A1 | 3/2012 | Quadri et al. |
| 2012/0078355 A1 | 3/2012 | Zipory et al. |
| 2012/0078357 A1 | 3/2012 | Conklin |
| 2012/0078359 A1 | 3/2012 | Li et al. |
| 2012/0083832 A1 | 4/2012 | Delaloye et al. |
| 2012/0083839 A1 | 4/2012 | Letac et al. |
| 2012/0083874 A1 | 4/2012 | Dale et al. |
| 2012/0083879 A1 | 4/2012 | Eberhardt et al. |
| 2012/0089022 A1 | 4/2012 | House et al. |
| 2012/0089223 A1 | 4/2012 | Nguyen et al. |
| 2012/0095552 A1 | 4/2012 | Spence et al. |
| 2012/0101570 A1 | 4/2012 | Tuval et al. |
| 2012/0101571 A1 | 4/2012 | Thambar et al. |
| 2012/0101572 A1 | 4/2012 | Kovalsky et al. |
| 2012/0109155 A1 | 5/2012 | Robinson et al. |
| 2012/0123511 A1 | 5/2012 | Brown |
| 2012/0123529 A1 | 5/2012 | Levi et al. |
| 2012/0123530 A1 | 5/2012 | Carpentier et al. |
| 2012/0123531 A1 | 5/2012 | Tsukashima et al. |
| 2012/0130473 A1 | 5/2012 | Norris et al. |
| 2012/0130474 A1 | 5/2012 | Buckley |
| 2012/0130475 A1 | 5/2012 | Shaw |
| 2012/0136434 A1 | 5/2012 | Carpentier et al. |
| 2012/0136436 A1 | 5/2012 | Cabiri et al. |
| 2012/0143323 A1 | 6/2012 | Hasenkam et al. |
| 2012/0150218 A1 | 6/2012 | Sandgren et al. |
| 2012/0150290 A1 | 6/2012 | Gabbay |
| 2012/0158021 A1 | 6/2012 | Morrill |
| 2012/0165915 A1 | 6/2012 | Melsheimer et al. |
| 2012/0165930 A1 | 6/2012 | Gifford, III et al. |
| 2012/0179086 A1 | 7/2012 | Shank et al. |
| 2012/0179244 A1 | 7/2012 | Schankereli et al. |
| 2012/0191182 A1 | 7/2012 | Hauser et al. |
| 2012/0197292 A1 | 8/2012 | Chin-Chen et al. |
| 2012/0197388 A1 | 8/2012 | Khairkhahan et al. |
| 2012/0215303 A1 | 8/2012 | Quadri et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0277845 A1 | 11/2012 | Bowe |
| 2012/0283757 A1 | 11/2012 | Miller et al. |
| 2012/0283824 A1 | 11/2012 | Lutter et al. |
| 2012/0290062 A1 | 11/2012 | McNamara et al. |
| 2012/0296349 A1 | 11/2012 | Smith et al. |
| 2012/0296360 A1 | 11/2012 | Norris et al. |
| 2012/0296417 A1 | 11/2012 | Hill et al. |
| 2012/0296418 A1 | 11/2012 | Bonyuet et al. |
| 2012/0296419 A1 | 11/2012 | Richardson |
| 2012/0300063 A1 | 11/2012 | Majkrzak et al. |
| 2012/0303116 A1 | 11/2012 | Gorman, III et al. |
| 2012/0310328 A1 | 12/2012 | Olson et al. |
| 2012/0310330 A1 | 12/2012 | Buchbinder et al. |
| 2012/0323313 A1 | 12/2012 | Seguin |
| 2012/0323316 A1 | 12/2012 | Chau et al. |
| 2012/0323317 A1 | 12/2012 | Karapetian et al. |
| 2012/0330408 A1 | 12/2012 | Hillukka et al. |
| 2012/0330410 A1 | 12/2012 | Hammer et al. |
| 2012/0330411 A1 | 12/2012 | Gross et al. |
| 2013/0006347 A1 | 1/2013 | McHugo |
| 2013/0018450 A1 | 1/2013 | Hunt |
| 2013/0018458 A1 | 1/2013 | Yohanan et al. |
| 2013/0023758 A1 | 1/2013 | Fabro |
| 2013/0030519 A1 | 1/2013 | Tran et al. |
| 2013/0030522 A1 | 1/2013 | Rowe et al. |
| 2013/0035759 A1 | 2/2013 | Gross et al. |
| 2013/0041204 A1 | 2/2013 | Heilman et al. |
| 2013/0041451 A1 | 2/2013 | Patterson et al. |
| 2013/0046373 A1 | 2/2013 | Cartledge et al. |
| 2013/0066341 A1 | 3/2013 | Ketai et al. |
| 2013/0066342 A1 | 3/2013 | Dell et al. |
| 2013/0079872 A1 | 3/2013 | Gallagher |
| 2013/0079873 A1 | 3/2013 | Migliazza et al. |
| 2013/0085529 A1 | 4/2013 | Housman |
| 2013/0090724 A1 | 4/2013 | Subramanian et al. |
| 2013/0096673 A1 | 4/2013 | Hill et al. |
| 2013/0116776 A1 | 5/2013 | Gross et al. |
| 2013/0116779 A1 | 5/2013 | Weber |
| 2013/0116780 A1 | 5/2013 | Miller et al. |
| 2013/0123896 A1 | 5/2013 | Bloss et al. |
| 2013/0123900 A1 | 5/2013 | Eblacas et al. |
| 2013/0123910 A1 | 5/2013 | Cartledge et al. |
| 2013/0131791 A1 | 5/2013 | Hlavka et al. |
| 2013/0131792 A1 | 5/2013 | Miller et al. |
| 2013/0138068 A1 | 5/2013 | Hu et al. |
| 2013/0144381 A1 | 6/2013 | Quadri et al. |
| 2013/0150945 A1 | 6/2013 | Crawford et al. |
| 2013/0150956 A1 | 6/2013 | Yohanan et al. |
| 2013/0158647 A1 | 6/2013 | Norris et al. |
| 2013/0166017 A1 | 6/2013 | Cartledge et al. |
| 2013/0166022 A1 | 6/2013 | Conklin |
| 2013/0172978 A1 | 7/2013 | Vidlund et al. |
| 2013/0172992 A1 | 7/2013 | Gross et al. |
| 2013/0178930 A1 | 7/2013 | Straubinger et al. |
| 2013/0190857 A1 | 7/2013 | Mitra et al. |
| 2013/0190861 A1 | 7/2013 | Chau et al. |
| 2013/0190863 A1 | 7/2013 | Call et al. |
| 2013/0190866 A1 | 7/2013 | Zipory et al. |
| 2013/0197622 A1 | 8/2013 | Mitra et al. |
| 2013/0197632 A1 | 8/2013 | Kovach et al. |
| 2013/0204361 A1 | 8/2013 | Adams et al. |
| 2013/0211501 A1 | 8/2013 | Buckley et al. |
| 2013/0211508 A1 | 8/2013 | Lane et al. |
| 2013/0226289 A1 | 8/2013 | Shaolian et al. |
| 2013/0226290 A1 | 8/2013 | Yellin et al. |
| 2013/0231735 A1 | 9/2013 | Deem et al. |
| 2013/0245742 A1 | 9/2013 | Norris |
| 2013/0253643 A1 | 9/2013 | Rolando et al. |
| 2013/0261737 A1 | 10/2013 | Costello |
| 2013/0261738 A1 | 10/2013 | Clague et al. |
| 2013/0268069 A1 | 10/2013 | Zakai et al. |
| 2013/0274870 A1 | 10/2013 | Lombardi et al. |
| 2013/0274873 A1 | 10/2013 | Delaloye et al. |
| 2013/0282059 A1 | 10/2013 | Ketai et al. |
| 2013/0289711 A1 | 10/2013 | Liddy et al. |
| 2013/0289718 A1 | 10/2013 | Tsukashima et al. |
| 2013/0289740 A1 | 10/2013 | Liddy et al. |
| 2013/0297013 A1 | 11/2013 | Klima et al. |
| 2013/0304093 A1 | 11/2013 | Serina et al. |
| 2013/0304197 A1 | 11/2013 | Buchbinder et al. |
| 2013/0304200 A1 | 11/2013 | McLean et al. |
| 2013/0310928 A1 | 11/2013 | Morriss et al. |
| 2013/0325114 A1 | 12/2013 | McLean et al. |
| 2013/0325118 A1 | 12/2013 | Cartledge |
| 2013/0331929 A1 | 12/2013 | Mitra et al. |
| 2014/0000112 A1 | 1/2014 | Braido et al. |
| 2014/0005767 A1 | 1/2014 | Glazier et al. |
| 2014/0005778 A1 | 1/2014 | Buchbinder et al. |
| 2014/0018911 A1 | 1/2014 | Zhou et al. |
| 2014/0018914 A1 | 1/2014 | Zipory et al. |
| 2014/0018915 A1 | 1/2014 | Biadillah et al. |
| 2014/0031928 A1 | 1/2014 | Murphy et al. |
| 2014/0046430 A1 | 2/2014 | Shaw |
| 2014/0052237 A1 | 2/2014 | Lane et al. |
| 2014/0067050 A1 | 3/2014 | Costello et al. |
| 2014/0067054 A1 | 3/2014 | Chau et al. |
| 2014/0081376 A1 | 3/2014 | Burkart et al. |
| 2014/0088368 A1 | 3/2014 | Park |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0099726 A1 | 4/2014 | Heller |
| 2014/0106951 A1 | 4/2014 | Brandon |
| 2014/0120287 A1 | 5/2014 | Jacoby et al. |
| 2014/0121749 A1 | 5/2014 | Roeder |
| 2014/0121763 A1 | 5/2014 | Duffy et al. |

(56)                    References Cited

U.S. PATENT DOCUMENTS

| | | |
|---|---|---|
| 2014/0135799 A1 | 5/2014 | Henderson |
| 2014/0135894 A1 | 5/2014 | Norris et al. |
| 2014/0135895 A1 | 5/2014 | Andress et al. |
| 2014/0142619 A1 | 5/2014 | Serina et al. |
| 2014/0142681 A1 | 5/2014 | Norris |
| 2014/0142688 A1 | 5/2014 | Duffy et al. |
| 2014/0142695 A1 | 5/2014 | Gross et al. |
| 2014/0148849 A1 | 5/2014 | Serina et al. |
| 2014/0148891 A1 | 5/2014 | Johnson |
| 2014/0148898 A1 | 5/2014 | Gross et al. |
| 2014/0155783 A1 | 6/2014 | Starksen et al. |
| 2014/0163668 A1 | 6/2014 | Rafiee |
| 2014/0163670 A1 | 6/2014 | Alon et al. |
| 2014/0163690 A1 | 6/2014 | White |
| 2014/0172069 A1 | 6/2014 | Roeder et al. |
| 2014/0172077 A1 | 6/2014 | Bruchman et al. |
| 2014/0172082 A1 | 6/2014 | Bruchman et al. |
| 2014/0188108 A1 | 7/2014 | Goodine et al. |
| 2014/0188140 A1 | 7/2014 | Meier et al. |
| 2014/0188210 A1 | 7/2014 | Beard et al. |
| 2014/0188215 A1 | 7/2014 | Hlavka et al. |
| 2014/0188221 A1 | 7/2014 | Chung et al. |
| 2014/0194970 A1 | 7/2014 | Chobotov |
| 2014/0194976 A1 | 7/2014 | Starksen et al. |
| 2014/0194981 A1 | 7/2014 | Menk et al. |
| 2014/0194983 A1 | 7/2014 | Kovalsky et al. |
| 2014/0207175 A1 | 7/2014 | Aggerholm |
| 2014/0207231 A1 | 7/2014 | Hacohen et al. |
| 2014/0214157 A1 | 7/2014 | Börtlein et al. |
| 2014/0214159 A1 | 7/2014 | Vidlund et al. |
| 2014/0222136 A1 | 8/2014 | Geist et al. |
| 2014/0222137 A1 | 8/2014 | Miller et al. |
| 2014/0222142 A1 | 8/2014 | Kovalsky et al. |
| 2014/0236287 A1 | 8/2014 | Clague et al. |
| 2014/0236289 A1 | 8/2014 | Alkhatib |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0249622 A1 | 9/2014 | Carmi et al. |
| 2014/0257461 A1 | 9/2014 | Robinson et al. |
| 2014/0257467 A1 | 9/2014 | Lane et al. |
| 2014/0257475 A1 | 9/2014 | Gross et al. |
| 2014/0257476 A1 | 9/2014 | Montorfano et al. |
| 2014/0275757 A1 | 9/2014 | Goodwin et al. |
| 2014/0276648 A1 | 9/2014 | Hammer et al. |
| 2014/0277358 A1 | 9/2014 | Slazas |
| 2014/0277409 A1 | 9/2014 | Börtlein et al. |
| 2014/0277411 A1 | 9/2014 | Börtlein et al. |
| 2014/0277412 A1 | 9/2014 | Börtlein et al. |
| 2014/0277413 A1 | 9/2014 | Richter et al. |
| 2014/0277417 A1 | 9/2014 | Schraut et al. |
| 2014/0277418 A1 | 9/2014 | Miller |
| 2014/0277422 A1 | 9/2014 | Ratz et al. |
| 2014/0277427 A1 | 9/2014 | Ratz et al. |
| 2014/0296962 A1 | 10/2014 | Cartledge et al. |
| 2014/0296969 A1 | 10/2014 | Tegels et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0324164 A1 | 10/2014 | Gross et al. |
| 2014/0329225 A1 | 11/2014 | Morin |
| 2014/0331475 A1 | 11/2014 | Duffy et al. |
| 2014/0336744 A1 | 11/2014 | Tani et al. |
| 2014/0343668 A1 | 11/2014 | Zipory et al. |
| 2014/0343670 A1 | 11/2014 | Bakis et al. |
| 2014/0350662 A1 | 11/2014 | Vaturi |
| 2014/0350670 A1 | 11/2014 | Keränen |
| 2014/0358222 A1 | 12/2014 | Gorman, III et al. |
| 2014/0358224 A1 | 12/2014 | Tegels et al. |
| 2014/0378331 A1 | 12/2014 | Morin |
| 2014/0379006 A1 | 12/2014 | Sutherland et al. |
| 2014/0379065 A1 | 12/2014 | Johnson et al. |
| 2014/0379074 A1 | 12/2014 | Spence et al. |
| 2014/0379076 A1 | 12/2014 | Vidlund et al. |
| 2015/0012087 A1 | 1/2015 | Miller et al. |
| 2015/0018940 A1 | 1/2015 | Quill et al. |
| 2015/0018944 A1 | 1/2015 | O'Connor et al. |
| 2015/0032205 A1 | 1/2015 | Matheny |
| 2015/0045880 A1 | 2/2015 | Hacohen |
| 2015/0045881 A1 | 2/2015 | Lim |
| 2015/0051697 A1 | 2/2015 | Spence et al. |
| 2015/0073544 A1 | 3/2015 | Gorman, III et al. |
| 2015/0081011 A1 | 3/2015 | Young et al. |
| 2015/0081014 A1 | 3/2015 | Gross et al. |
| 2015/0094802 A1 | 4/2015 | Buchbinder et al. |
| 2015/0105855 A1 | 4/2015 | Cabiri et al. |
| 2015/0119970 A1 | 4/2015 | Nakayama et al. |
| 2015/0127097 A1 | 5/2015 | Neumann et al. |
| 2015/0142100 A1 | 5/2015 | Morriss et al. |
| 2015/0142103 A1 | 5/2015 | Vidlund |
| 2015/0148894 A1 | 5/2015 | Damm et al. |
| 2015/0148896 A1 | 5/2015 | Karapetian et al. |
| 2015/0157457 A1 | 6/2015 | Hacohen |
| 2015/0157458 A1 | 6/2015 | Thambar et al. |
| 2015/0164640 A1 | 6/2015 | McLean et al. |
| 2015/0173896 A1 | 6/2015 | Richter et al. |
| 2015/0173897 A1 | 6/2015 | Raanani et al. |
| 2015/0182336 A1 | 7/2015 | Zipory et al. |
| 2015/0196390 A1 | 7/2015 | Ma et al. |
| 2015/0196393 A1 | 7/2015 | Vidlund et al. |
| 2015/0216661 A1 | 8/2015 | Hacohen et al. |
| 2015/0230924 A1 | 8/2015 | Miller et al. |
| 2015/0238313 A1 | 8/2015 | Spence et al. |
| 2015/0238315 A1 | 8/2015 | Rabito et al. |
| 2015/0245934 A1 | 9/2015 | Lombardi et al. |
| 2015/0250588 A1 | 9/2015 | Yang et al. |
| 2015/0272730 A1 | 10/2015 | Melnick et al. |
| 2015/0272731 A1 | 10/2015 | Racchini et al. |
| 2015/0272734 A1 | 10/2015 | Sheps et al. |
| 2015/0282964 A1 | 10/2015 | Beard et al. |
| 2015/0305903 A1 | 10/2015 | Kitaoka |
| 2015/0320556 A1 | 11/2015 | Levi et al. |
| 2015/0327994 A1 | 11/2015 | Morriss et al. |
| 2015/0328000 A1 | 11/2015 | Ratz et al. |
| 2015/0335429 A1 | 11/2015 | Morriss et al. |
| 2015/0342736 A1 | 12/2015 | Rabito et al. |
| 2015/0351903 A1 | 12/2015 | Morriss et al. |
| 2015/0351904 A1 | 12/2015 | Cooper et al. |
| 2015/0351906 A1 | 12/2015 | Hammer et al. |
| 2015/0359629 A1 | 12/2015 | Ganesan et al. |
| 2015/0359631 A1 | 12/2015 | Sheahan et al. |
| 2016/0008129 A1 | 1/2016 | Siegel |
| 2016/0030165 A1 | 2/2016 | Mitra et al. |
| 2016/0030169 A1 | 2/2016 | Shahriari |
| 2016/0030170 A1 | 2/2016 | Alkhatib et al. |
| 2016/0030171 A1 | 2/2016 | Quijano et al. |
| 2016/0038281 A1 | 2/2016 | Delaloye et al. |
| 2016/0089482 A1 | 3/2016 | Siegenthaler |
| 2016/0095700 A1 | 4/2016 | Righini |
| 2016/0100939 A1 | 4/2016 | Armstrong et al. |
| 2016/0106537 A1 | 4/2016 | Christianson et al. |
| 2016/0106539 A1 | 4/2016 | Buchbinder et al. |
| 2016/0113765 A1 | 4/2016 | Ganesan et al. |
| 2016/0113766 A1 | 4/2016 | Ganesan et al. |
| 2016/0113768 A1 | 4/2016 | Ganesan et al. |
| 2016/0125160 A1 | 5/2016 | Heneghan et al. |
| 2016/0157862 A1 | 6/2016 | Hernandez et al. |
| 2016/0175095 A1 | 6/2016 | Dienno et al. |
| 2016/0184098 A1 | 6/2016 | Vaturi |
| 2016/0200773 A1 | 7/2016 | Morin |
| 2016/0213473 A1 | 7/2016 | Hacohen et al. |
| 2016/0220367 A1 | 8/2016 | Barrett |
| 2016/0228244 A1 | 8/2016 | Cerf et al. |
| 2016/0228247 A1 | 8/2016 | Maimon et al. |
| 2016/0228249 A1 | 8/2016 | Mantanus et al. |
| 2016/0242902 A1 | 8/2016 | Morriss et al. |
| 2016/0245802 A1 | 8/2016 | Morin et al. |
| 2016/0258939 A1 | 9/2016 | Morin et al. |
| 2016/0262885 A1 | 9/2016 | Sandstrom et al. |
| 2016/0266089 A1 | 9/2016 | Morin et al. |
| 2016/0270911 A1 | 9/2016 | Ganesan et al. |
| 2016/0296330 A1 | 10/2016 | Hacohen |
| 2016/0296332 A1 | 10/2016 | Zhou et al. |

(56)　　References Cited

U.S. PATENT DOCUMENTS

| | | |
|---|---|---|
| 2016/0310268 A1 | 10/2016 | Oba et al. |
| 2016/0310274 A1 | 10/2016 | Gross et al. |
| 2016/0317301 A1 | 11/2016 | Quadri et al. |
| 2016/0317305 A1 | 11/2016 | Pelled et al. |
| 2016/0324633 A1 | 11/2016 | Gross et al. |
| 2016/0324635 A1 | 11/2016 | Vidlund et al. |
| 2016/0324640 A1 | 11/2016 | Gifford et al. |
| 2016/0331526 A1 | 11/2016 | Schweich et al. |
| 2016/0331527 A1 | 11/2016 | Vidlund et al. |
| 2016/0338706 A1 | 11/2016 | Rowe |
| 2016/0367360 A1 | 12/2016 | Cartledge et al. |
| 2016/0367368 A1 | 12/2016 | Vidlund et al. |
| 2016/0374801 A1 | 12/2016 | Jimenez et al. |
| 2016/0374802 A1 | 12/2016 | Levi et al. |
| 2017/0042678 A1 | 2/2017 | Ganesan et al. |
| 2017/0049435 A1 | 2/2017 | Sauer et al. |
| 2017/0056166 A1 | 3/2017 | Ratz et al. |
| 2017/0056169 A1 | 3/2017 | Johnson et al. |
| 2017/0056171 A1 | 3/2017 | Cooper et al. |
| 2017/0065407 A1 | 3/2017 | Hacohen et al. |
| 2017/0065411 A1 | 3/2017 | Grundeman et al. |
| 2017/0074855 A1 | 3/2017 | Morin et al. |
| 2017/0100236 A1 | 4/2017 | Robertson et al. |
| 2017/0128205 A1 | 5/2017 | Tamir et al. |
| 2017/0135816 A1 | 5/2017 | Lashinski et al. |
| 2017/0143938 A1 | 5/2017 | Ogle et al. |
| 2017/0165054 A1 | 6/2017 | Benson et al. |
| 2017/0165063 A1 | 6/2017 | Anderson et al. |
| 2017/0189174 A1 | 7/2017 | Braido et al. |
| 2017/0196688 A1 | 7/2017 | Christianson et al. |
| 2017/0196692 A1 | 7/2017 | Kirk et al. |
| 2017/0209264 A1 | 7/2017 | Chau et al. |
| 2017/0216026 A1 | 8/2017 | Quill et al. |
| 2017/0224323 A1 | 8/2017 | Rowe et al. |
| 2017/0231757 A1 | 8/2017 | Gassler |
| 2017/0231759 A1 | 8/2017 | Geist et al. |
| 2017/0231760 A1 | 8/2017 | Lane et al. |
| 2017/0231766 A1 | 8/2017 | Hariton et al. |
| 2017/0234850 A1 | 8/2017 | Morin |
| 2017/0239048 A1 | 8/2017 | Goldfarb et al. |
| 2017/0252159 A1 | 9/2017 | Hacohen et al. |
| 2017/0266003 A1 | 9/2017 | Hammer et al. |
| 2017/0325948 A1 | 11/2017 | Wallace et al. |
| 2017/0333183 A1 | 11/2017 | Backus |
| 2017/0333187 A1 | 11/2017 | Hariton et al. |
| 2017/0349940 A1 | 12/2017 | Morin et al. |
| 2017/0360426 A1 | 12/2017 | Hacohen et al. |
| 2017/0367823 A1 | 12/2017 | Hariton et al. |
| 2018/0000580 A1 | 1/2018 | Wallace et al. |
| 2018/0014930 A1 | 1/2018 | Hariton et al. |
| 2018/0014932 A1 | 1/2018 | Hammer et al. |
| 2018/0021129 A1 | 1/2018 | Peterson et al. |
| 2018/0023114 A1 | 1/2018 | Morin et al. |
| 2018/0023115 A1 | 1/2018 | Morin et al. |
| 2018/0028215 A1 | 2/2018 | Cohen |
| 2018/0028311 A1 | 2/2018 | Hacohen |
| 2018/0049873 A1 | 2/2018 | Manash et al. |
| 2018/0055628 A1 | 3/2018 | Patel et al. |
| 2018/0055629 A1 | 3/2018 | Oba et al. |
| 2018/0055630 A1 | 3/2018 | Patel et al. |
| 2018/0098850 A1 | 4/2018 | Rafiee et al. |
| 2018/0116790 A1 | 5/2018 | Ratz et al. |
| 2018/0116843 A1 | 5/2018 | Schreck et al. |
| 2018/0125644 A1 | 5/2018 | Conklin |
| 2018/0132999 A1 | 5/2018 | Perouse |
| 2018/0147059 A1 | 5/2018 | Hammer et al. |
| 2018/0153687 A1 | 6/2018 | Hariton et al. |
| 2018/0153689 A1 | 6/2018 | Maimon et al. |
| 2018/0153696 A1 | 6/2018 | Albitov et al. |
| 2018/0161159 A1 | 6/2018 | Lee et al. |
| 2018/0177593 A1 | 6/2018 | Hariton et al. |
| 2018/0177594 A1 | 6/2018 | Patel et al. |
| 2018/0185148 A1 | 7/2018 | Hariton et al. |
| 2018/0206983 A1 | 7/2018 | Noe et al. |
| 2018/0214263 A1 | 8/2018 | Rolando et al. |
| 2018/0243086 A1 | 8/2018 | Barbarino et al. |
| 2018/0250126 A1 | 9/2018 | O'connor et al. |
| 2018/0250130 A1 | 9/2018 | Hariton et al. |
| 2018/0250147 A1 | 9/2018 | Syed |
| 2018/0256323 A1 | 9/2018 | Hariton et al. |
| 2018/0256325 A1 | 9/2018 | Hariton et al. |
| 2018/0271654 A1 | 9/2018 | Hariton et al. |
| 2018/0271655 A1 | 9/2018 | Hariton et al. |
| 2018/0280136 A1 | 10/2018 | Hariton et al. |
| 2018/0289479 A1 | 10/2018 | Hariton et al. |
| 2018/0296333 A1 | 10/2018 | Dixon et al. |
| 2018/0296336 A1 | 10/2018 | Cooper et al. |
| 2018/0296341 A1 | 10/2018 | Noe et al. |
| 2018/0325671 A1 | 11/2018 | Abunassar et al. |
| 2018/0338829 A1 | 11/2018 | Hariton et al. |
| 2018/0338830 A1 | 11/2018 | Hariton et al. |
| 2018/0338831 A1 | 11/2018 | Hariton et al. |
| 2018/0344457 A1 | 12/2018 | Gross et al. |
| 2018/0344490 A1 | 12/2018 | Fox et al. |
| 2018/0353294 A1 | 12/2018 | Calomeni et al. |
| 2018/0360457 A1 | 12/2018 | Ellis et al. |
| 2019/0000613 A1 | 1/2019 | Delgado et al. |
| 2019/0008640 A1 | 1/2019 | Cooper et al. |
| 2019/0015093 A1 | 1/2019 | Hacohen et al. |
| 2019/0015200 A1 | 1/2019 | Delgado et al. |
| 2019/0021852 A1 | 1/2019 | Delgado et al. |
| 2019/0021857 A1 | 1/2019 | Hacohen et al. |
| 2019/0038404 A1 | 2/2019 | Iamberger et al. |
| 2019/0038405 A1 | 2/2019 | Iamberger et al. |
| 2019/0046314 A1 | 2/2019 | Levi et al. |
| 2019/0053895 A1 | 2/2019 | Levi |
| 2019/0053896 A1 | 2/2019 | Adamek-bowers et al. |
| 2019/0060060 A1 | 2/2019 | Chau et al. |
| 2019/0060068 A1 | 2/2019 | Cope et al. |
| 2019/0060070 A1 | 2/2019 | Groothuis et al. |
| 2019/0069997 A1 | 3/2019 | Ratz et al. |
| 2019/0069998 A1 | 3/2019 | Hacohen |
| 2019/0076244 A1 | 3/2019 | Yohanan et al. |
| 2019/0083242 A1 | 3/2019 | Hariton et al. |
| 2019/0083243 A1 | 3/2019 | Hariton et al. |
| 2019/0083244 A1 | 3/2019 | Hariton et al. |
| 2019/0083245 A1 | 3/2019 | Hariton et al. |
| 2019/0083246 A1 | 3/2019 | Hariton et al. |
| 2019/0083247 A1 | 3/2019 | Hariton et al. |
| 2019/0083248 A1 | 3/2019 | Hariton et al. |
| 2019/0083249 A1 | 3/2019 | Hariton et al. |
| 2019/0083250 A1 | 3/2019 | Hariton et al. |
| 2019/0083251 A1 | 3/2019 | Hariton et al. |
| 2019/0083252 A1 | 3/2019 | Hariton et al. |
| 2019/0083253 A1 | 3/2019 | Hariton et al. |
| 2019/0083254 A1 | 3/2019 | Hariton et al. |
| 2019/0083261 A1 | 3/2019 | Perszyk et al. |
| 2019/0083262 A1 | 3/2019 | Hariton et al. |
| 2019/0083263 A1 | 3/2019 | Hariton et al. |
| 2019/0105153 A1 | 4/2019 | Barash et al. |
| 2019/0117391 A1 | 4/2019 | Humair |
| 2019/0167423 A1 | 6/2019 | Hariton et al. |
| 2019/0175339 A1 | 6/2019 | Vidlund |
| 2019/0175342 A1 | 6/2019 | Hariton et al. |
| 2019/0183639 A1 | 6/2019 | Moore |
| 2019/0183644 A1 | 6/2019 | Hacohen |
| 2019/0192295 A1 | 6/2019 | Spence et al. |
| 2019/0216602 A1 | 7/2019 | Lozonschi |
| 2019/0224008 A1 | 7/2019 | Bressloff et al. |
| 2019/0231525 A1 | 8/2019 | Hariton et al. |
| 2019/0240010 A1 | 8/2019 | Hacohen |
| 2019/0254818 A1 | 8/2019 | Quill et al. |
| 2019/0321172 A1 | 10/2019 | Gross et al. |
| 2019/0328519 A1 | 10/2019 | Hariton et al. |
| 2019/0336280 A1 | 11/2019 | Naor |
| 2019/0343627 A1 | 11/2019 | Hariton et al. |
| 2019/0350701 A1 | 11/2019 | Adamek-Bowers et al. |
| 2019/0365530 A1 | 12/2019 | Hoang et al. |
| 2019/0388218 A1 | 12/2019 | Vidlund et al. |
| 2019/0388220 A1 | 12/2019 | Vidlund et al. |
| 2019/0388223 A1 | 12/2019 | Hariton et al. |
| 2020/0000449 A1 | 1/2020 | Goldfarb et al. |
| 2020/0000579 A1 | 1/2020 | Manash et al. |
| 2020/0000580 A1 | 1/2020 | Hacohen |

(56) References Cited

U.S. PATENT DOCUMENTS

| | | | |
|---|---|---|---|
| 2020/0015964 A1 | 1/2020 | Noe et al. |
| 2020/0030098 A1 | 1/2020 | Delgado et al. |
| 2020/0038181 A1 | 2/2020 | Hariton et al. |
| 2020/0046496 A1 | 2/2020 | Hammer et al. |
| 2020/0046497 A1 | 2/2020 | Hariton et al. |
| 2020/0054335 A1 | 2/2020 | Hernandez et al. |
| 2020/0054451 A1 | 2/2020 | Hariton et al. |
| 2020/0060818 A1 | 2/2020 | Geist et al. |
| 2020/0069417 A1 | 3/2020 | Morin et al. |
| 2020/0069424 A1 | 3/2020 | Hariton et al. |
| 2020/0078002 A1 | 3/2020 | Hacohen et al. |
| 2020/0113677 A1 | 4/2020 | McCann et al. |
| 2020/0113689 A1 | 4/2020 | McCann et al. |
| 2020/0113692 A1 | 4/2020 | McCann et al. |
| 2020/0129294 A1 | 4/2020 | Hariton et al. |
| 2020/0138567 A1 | 5/2020 | Marr et al. |
| 2020/0146671 A1 | 5/2020 | Hacohen et al. |
| 2020/0146824 A1 | 5/2020 | Hammer et al. |
| 2020/0163760 A1 | 5/2020 | Hariton et al. |
| 2020/0163761 A1 | 5/2020 | Hariton et al. |
| 2020/0205969 A1 | 7/2020 | Hacohen |
| 2020/0214832 A1 | 7/2020 | Metchik et al. |
| 2020/0237512 A1 | 7/2020 | McCann et al. |
| 2020/0246136 A1 | 8/2020 | Marr et al. |
| 2020/0246140 A1 | 8/2020 | Hariton et al. |
| 2020/0253600 A1 | 8/2020 | Darabian |
| 2020/0261094 A1 | 8/2020 | Goldfarb et al. |
| 2020/0281721 A1 | 9/2020 | Hariton et al. |
| 2020/0297486 A1 | 9/2020 | Hariton et al. |
| 2020/0306037 A1 | 10/2020 | Siegel et al. |
| 2020/0315786 A1 | 10/2020 | Metchik et al. |
| 2020/0315797 A1 | 10/2020 | Hariton et al. |
| 2020/0330221 A1 | 10/2020 | Hacohen |
| 2020/0330227 A1 | 10/2020 | Hacohen |
| 2020/0337842 A1 | 10/2020 | Metchik et al. |
| 2020/0360139 A1 | 11/2020 | Hammer et al. |
| 2020/0390546 A1 | 12/2020 | Hariton et al. |
| 2020/0390548 A1 | 12/2020 | Hariton et al. |
| 2020/0397573 A1 | 12/2020 | Hariton et al. |
| 2021/0085455 A1 | 3/2021 | Bateman et al. |
| 2021/0085457 A1 | 3/2021 | Hariton et al. |
| 2021/0093449 A1 | 4/2021 | Hariton et al. |
| 2021/0106419 A1 | 4/2021 | Abunassar |
| 2021/0113331 A1 | 4/2021 | Quadri et al. |
| 2021/0137680 A1 | 5/2021 | Kizuka et al. |
| 2021/0145578 A1 | 5/2021 | Hariton et al. |
| 2021/0169467 A1 | 6/2021 | Hacohen et al. |
| 2021/0196461 A1 | 7/2021 | Hariton et al. |
| 2021/0259835 A1 | 8/2021 | Tyler, II et al. |
| 2021/0330456 A1 | 10/2021 | Hacohen et al. |
| 2021/0361422 A1 | 11/2021 | Gross et al. |
| 2021/0361426 A1 | 11/2021 | Hacohen |
| 2021/0393402 A1 | 12/2021 | Hammer et al. |
| 2021/0401573 A1 | 12/2021 | Gross et al. |
| 2022/0000612 A1 | 1/2022 | Hacohen |
| 2023/0201015 A1 | 6/2023 | Gurovich et al. |

FOREIGN PATENT DOCUMENTS

| | | |
|---|---|---|
| CN | 101653365 | 2/2010 |
| CN | 103974674 | 8/2014 |
| CN | 103997990 | 8/2014 |
| CN | 105324091 | 2/2016 |
| CN | 112603598 | 4/2021 |
| EP | 0170262 | 2/1986 |
| EP | 06/14342 | 9/1994 |
| EP | 10/06905 | 6/2000 |
| EP | 0954257 | 8/2000 |
| EP | 1258437 | 11/2002 |
| EP | 1264582 | 12/2002 |
| EP | 0871417 | 10/2003 |
| EP | 1266641 | 10/2004 |
| EP | 1034753 | 2/2005 |
| EP | 1258232 | 1/2006 |
| EP | 1637092 | 3/2006 |
| EP | 1990014 | 11/2008 |
| EP | 1562522 | 12/2008 |
| EP | 1420723 | 1/2009 |
| EP | 1903991 | 9/2009 |
| EP | 1418865 | 10/2009 |
| EP | 2119399 | 11/2009 |
| EP | 1531762 | 4/2010 |
| EP | 1450733 | 2/2011 |
| EP | 2 446 915 A1 | 5/2012 |
| EP | 2088965 | 11/2012 |
| EP | 1768630 | 1/2015 |
| EP | 1861045 | 3/2015 |
| EP | 1465555 | 5/2015 |
| EP | 2349124 | 10/2018 |
| EP | 2739214 | 10/2018 |
| EP | 3417813 | 12/2018 |
| EP | 3583922 | 12/2019 |
| EP | 3270825 | 4/2020 |
| EP | 2485795 | 9/2020 |
| IL | 223448 | 12/2012 |
| JP | S53152790 | 12/1978 |
| KR | 20010046894 | 6/2001 |
| WO | 92/05093 | 4/1992 |
| WO | 93/10714 | 6/1993 |
| WO | 96/39963 | 12/1996 |
| WO | 96/40344 | 12/1996 |
| WO | 97/01369 | 1/1997 |
| WO | 98/46149 | 10/1998 |
| WO | 1998/043557 | 10/1998 |
| WO | 1999/030647 | 6/1999 |
| WO | 00/22981 | 4/2000 |
| WO | 2000-047139 | 8/2000 |
| WO | 01/26586 | 4/2001 |
| WO | 01/56457 | 8/2001 |
| WO | 2001-062189 | 8/2001 |
| WO | 01/82832 | 11/2001 |
| WO | 02/085250 | 10/2002 |
| WO | 02/085251 | 10/2002 |
| WO | 02/085252 | 10/2002 |
| WO | 2003/020179 | 3/2003 |
| WO | 2003/028558 | 4/2003 |
| WO | 03/047467 | 6/2003 |
| WO | 2003/049647 | 6/2003 |
| WO | 2003/105667 | 12/2003 |
| WO | 2004/028399 | 4/2004 |
| WO | 04/103434 | 12/2004 |
| WO | 2004/108191 | 12/2004 |
| WO | 05/021063 | 3/2005 |
| WO | 05/046488 | 5/2005 |
| WO | 2005/062931 | 7/2005 |
| WO | 2005/107650 | 11/2005 |
| WO | 2006/007389 | 1/2006 |
| WO | 2006/007401 | 1/2006 |
| WO | 06/012013 | 2/2006 |
| WO | 06/012038 | 2/2006 |
| WO | 06/054930 | 5/2006 |
| WO | 2006/065212 | 6/2006 |
| WO | 2006/070372 | 7/2006 |
| WO | 06/086434 | 8/2006 |
| WO | 2006/089236 | 8/2006 |
| WO | 2006/091163 | 8/2006 |
| WO | 06/097931 | 9/2006 |
| WO | 06/105084 | 10/2006 |
| WO | 06/116558 | 11/2006 |
| WO | 2006/128193 A2 | 11/2006 |
| WO | 07/011799 | 1/2007 |
| WO | 2007/030063 | 3/2007 |
| WO | 2007/047488 | 4/2007 |
| WO | 2007/059252 | 5/2007 |
| WO | 07/121314 | 10/2007 |
| WO | 07/136783 | 11/2007 |
| WO | 07/136981 | 11/2007 |
| WO | 08/013915 | 1/2008 |
| WO | 2008/014144 | 1/2008 |
| WO | 2008/029296 | 3/2008 |
| WO | 2008/031103 | 3/2008 |
| WO | 2008/058940 | 5/2008 |
| WO | 08/068756 | 6/2008 |
| WO | 2008/070797 | 6/2008 |

(56)                References Cited

FOREIGN PATENT DOCUMENTS

| WO | 2008/103722 | | 8/2008 |
|----|----|----|----|
| WO | 2009/026563 | | 2/2009 |
| WO | 09/033469 | | 3/2009 |
| WO | 09/053497 | | 4/2009 |
| WO | 2009/080801 | | 7/2009 |
| WO | 2009/091509 | | 7/2009 |
| WO | 2009/160631 | | 10/2009 |
| WO | 10/004546 | | 1/2010 |
| WO | 2010/000454 | | 1/2010 |
| WO | 2010/005827 | | 1/2010 |
| WO | 2010/006627 | | 1/2010 |
| WO | 2010/006905 | | 1/2010 |
| WO | 2010/027485 | | 3/2010 |
| WO | 2010/037141 | | 4/2010 |
| WO | 2010/044851 | | 4/2010 |
| WO | 2010/045297 | | 4/2010 |
| WO | 2010/057262 | | 5/2010 |
| WO | 2010/073246 | | 7/2010 |
| WO | 2010/081033 | | 7/2010 |
| WO | 2010/085649 | | 7/2010 |
| WO | 2010/099032 | A2 | 9/2010 |
| WO | 2010/121076 | | 10/2010 |
| WO | 2010/128502 | | 11/2010 |
| WO | 2010/128503 | | 11/2010 |
| WO | 2010/150178 | | 12/2010 |
| WO | 2011/025972 | | 3/2011 |
| WO | 2011/051942 | | 5/2011 |
| WO | 2011/067770 | | 6/2011 |
| WO | 2011/069048 | | 6/2011 |
| WO | 2011/089401 | | 7/2011 |
| WO | 2011/089601 | | 7/2011 |
| WO | 2011/106137 | | 9/2011 |
| WO | 2011/111047 | | 9/2011 |
| WO | 01/87190 | | 11/2011 |
| WO | 2011/137531 | | 11/2011 |
| WO | 2011-143263 | | 11/2011 |
| WO | 2011/144351 | | 11/2011 |
| WO | 2011/148374 | | 12/2011 |
| WO | 2011/154942 | | 12/2011 |
| WO | 2012/011108 | | 1/2012 |
| WO | 2012/014201 | | 2/2012 |
| WO | 2012/024428 | | 2/2012 |
| WO | 2012/036740 | | 3/2012 |
| WO | 2012/048035 | | 4/2012 |
| WO | 2012/068541 | | 5/2012 |
| WO | 2012/127309 | | 9/2012 |
| WO | 2012/176195 | | 12/2012 |
| WO | 2012/177942 | | 12/2012 |
| WO | 2013/021374 | | 2/2013 |
| WO | 2013/021375 | | 2/2013 |
| WO | 2013/021384 | | 2/2013 |
| WO | 2013/059747 | | 4/2013 |
| WO | 2013/069019 | | 5/2013 |
| WO | 2013/072496 | | 5/2013 |
| WO | 2013/078497 | | 6/2013 |
| WO | 2013/088327 | | 6/2013 |
| WO | 2013/114214 | | 8/2013 |
| WO | 2013/128436 | | 9/2013 |
| WO | 2013/175468 | | 11/2013 |
| WO | 2014/022124 | | 2/2014 |
| WO | 2014/064694 | | 5/2014 |
| WO | 2014/064695 | | 5/2014 |
| WO | 2014/076696 | | 5/2014 |
| WO | 2014/087402 | | 6/2014 |
| WO | 2014/115149 | | 7/2014 |
| WO | 2014/121280 | | 8/2014 |
| WO | 2014/144937 | | 9/2014 |
| WO | 2014/145338 | | 9/2014 |
| WO | 2014/164364 | | 10/2014 |
| WO | 2014/194178 | | 12/2014 |
| WO | 2014/195786 | | 12/2014 |
| WO | 2015/059699 | | 4/2015 |
| WO | 2015/173794 | | 11/2015 |
| WO | 2015/191923 | | 12/2015 |
| WO | 2016/016899 | | 2/2016 |
| WO | 2016/093877 | | 6/2016 |
| WO | 2016/098104 | | 6/2016 |
| WO | 2016/125160 | | 8/2016 |
| WO | 2016/150806 | | 9/2016 |
| WO | 2016/183526 | | 11/2016 |
| WO | 2017/223486 | | 12/2017 |
| WO | 2018/025260 | | 2/2018 |
| WO | 2018/025263 | | 2/2018 |
| WO | 2018/029680 | | 2/2018 |
| WO | 2018/039631 | | 3/2018 |
| WO | 2018/106837 | | 6/2018 |
| WO | 2018/112429 | | 6/2018 |
| WO | 2018/118717 | | 6/2018 |
| WO | 2018/131042 | | 7/2018 |
| WO | 2018/131043 | | 7/2018 |
| WO | 2019/026059 | | 2/2019 |
| WO | 2019/027507 | | 2/2019 |
| WO | 2019/030753 | | 2/2019 |
| WO | 2019/077595 | | 4/2019 |
| WO | 2019/116369 | | 6/2019 |
| WO | 2019/138400 | | 7/2019 |
| WO | 2019/195860 | | 10/2019 |
| WO | 2019/202579 | | 10/2019 |
| WO | 2020/058972 | | 3/2020 |
| WO | 2020/167677 | | 8/2020 |
| WO | 2021/156866 | | 8/2021 |
| WO | 2021/178400 | | 9/2021 |
| WO | 2021/186424 | | 9/2021 |

OTHER PUBLICATIONS

An Office Action dated July 3. 2024, which issued during the prosecution of U.S. Appl. No. 18/109,937.

An Office Action dated Jul. 24, 2024, which issued during the prosecution of U.S. Appl. No. 18/234,745.

An Office Action dated August 1. 2024, which issued during the prosecution of U.S. Appl. No. 18/368,250.

An Office Action dated Aug. 9, 2024, which issued during the prosecution of Chinese Patent Application No. 202210336863.0.

Submissions ahead of oral proceedings, dated Jan. 17, 2025.

Letter accompanying subsequently filed items, dated Jan. 30, 2025.

Bharucha, Tara, et al. "Cor triatriatum or divided atriums: which approach provides the better understanding?." Cardiology in the Young 25.2 (2015): 193-207.

Zhu 2015 (The Cardiac Skeleton and the Aortic Root Chap. 9).

An Office Action dated Mar. 25, 2024, which issued during the prosecution of U.S. Appl. No. 17/841,912.

Notice of Allowance dated Sep. 27, 2023, which issued during the prosecution of U.S. Appl. No. 17/010,886.

Notice of Allowance dated Apr. 10, 2024, which issued during the prosecution of U.S. Appl. No. 17/010,886.

An Office Action dated Apr. 25, 2024, which issued during the prosecution of U.S. Appl. No. 17/397,235.

A Brief Communication together with a Letter from the opponent regarding European Patent Application No. 14710060.6, dated Apr. 12, 2024.

A Letter from the opponent regarding European Patent Application No. 14710060.6, dated Apr. 5, 2024.

Summons to Attend Oral Proceedings regarding European Patent Application No. 14710060.6, dated May 10, 2024.

An Office Action dated Dec. 19, 2023, which issued during the prosecution of U.S. Appl. No. 17/010,886.

European Search Report dated Nov. 14, 2023 which issued during the prosecution of Applicant's European App No. 23191562.0.

An International Search Report and a Written Opinion both dated Jan. 18, 2024, which issued during the prosecution of Applicant's PCT/IL2023/050958.

An Office Action dated Nov. 3, 2023, which issued during the prosecution of Canadian Patent Application No. 3,162,308.

An Office Action dated Jan. 25, 2024, which issued during the prosecution of U.S. Appl. No. 18/090,058.

Notice of Allowance dated Mar. 13, 2024, which issued during the prosecution of U.S. Appl. No. 18/216,391.

(56)          References Cited

OTHER PUBLICATIONS

Opposition To European Patent No. EP 2 948 103 dated Sep. 6, 2023.

Communication issued Sep. 12, 2023 in European Application No. 14710060.6.

European Search Report dated Mar. 20, 2023 which issued during the prosecution of Applicant's European App No. 22204764.9.

An Office Action dated Apr. 14, 2023, which issued during the prosecution of U.S. Appl. No. 16/144,054.

An Office Action dated May 15, 2023, which issued during the prosecution of U.S. Appl. No. 16/656,790.

An Office Action dated May 16, 2023, which issued during the prosecution of U.S. Appl. No. 17/114,771.

An Office Action dated May 17, 2023, which issued during the prosecution of U.S. Appl. No. 17/466,785.

An Office Action dated May 25, 2023, which issued during the prosecution of U.S. Appl. No. 17/397,235.

An Office Action dated Mar. 3, 2023, which issued during the prosecution of European Patent Application No. 17 751 143.3.

An Office Action dated Mar. 20, 2023, which issued during the prosecution of U.S. Appl. No. 17/181,722.

An Office Action dated Sep. 29, 2022, which issued during the prosecution of U.S. Appl. No. 17/010,886.

An Office Action dated Sep. 29, 2022, which issued during the prosecution of U.S. Appl. No. 16/656,790.

An Office Action dated Nov. 2, 2022, which issued during the prosecution of U.S. Appl. No. 17/004,693.

An Office Action dated Nov. 28, 2022, which issued during the prosecution of U.S. Appl. No. 17/141,853.

An Office Action dated Oct. 19, 2022, which issued during the prosecution of U.S. Appl. No. 17/875,589.

An Office Action dated Oct. 26, 2022, which issued during the prosecution of U.S. Appl. No. 16/746,489.

An Office Action dated Jul. 27, 2022, which issued during the prosecution of U.S. Appl. No. 16/881,350.

An Office Action dated Sep. 21, 2022, which issued during the prosecution of U.S. Appl. No. 16/776,581.

An Office Action dated Jul. 20, 2022, which issued during the prosecution of U.S. Appl. No. 17/101,787.

An Office Action dated Sep. 16, 2022, which issued during the prosecution of U.S. Appl. No. 16/135,466.

An Office Action dated Aug. 1, 2022, which issued during the prosecution of European Patent Application No. 18826823.9.

European Search Report dated Sep. 6, 2022 which issued during the prosecution of Applicant's European App No. 22161862.2.

IPR2021-01051 Petitioners' Reply To Preliminary Guidance dated Aug. 2, 2022.

IPR2021-01051 Patent Owner's Sur-Reply To Petitioners' Reply To Preliminary Guidance dated Aug. 23, 2022.

An Office Action dated Aug. 5, 2022, which issued during the prosecution of U.S. Appl. No. 16/760,147.

An Office Action dated Sep. 8, 2022, which issued during the prosecution of U.S. Appl. No. 16/896,858.

Extended European Search Report issued Oct. 11, 2021 in European Application No. 21176010.3.

Fann et al., "Beating Heart Catheter-Based Edge-to-Edge Mitral Valve Procedure in a Porcine Model", Circulation, 2004, vol. 110, pp. 988-993, Cardiovalve Exhibit 2006 (6 pages total).

Feldman et al., "Percutaneous Mitral Leaflet Repair: MitralClip Therapy for Mitral Regurgitation", Informa Healthcare, 2012, CRC Press, pp. 31-44, Cardiovalve Exhibit 2009 (8 pages total).

Feldman et al., "Percutaneous Mitral Valve Repair Using the Edge-to-Edge Technique", Journal of the American College of Cardiology, 2005, vol. 46, No. 11, pp. 2134-2140 (7 pages total).

IPR2021-00383 "Patent Owner's Contingent Motion to Amend", dated Oct. 13, 2021 (35 pages total).

IPR2021-00383 "Patent Owner's Response", dated Oct. 13, 2021 (75 pages total).

Maisano et al., "The Evolution From Surgery to Percutaneous Mitral Valve Interventions", Journal of the American College of Cardiology, 2011, vol. 58, No. 21, pp. 2174-2182 (9 pages total).

Notice of Allowance issued Sep. 15, 2021 in U.S. Appl. No. 16/135,599.

Office Action issued Oct. 14, 2021 in U.S. Appl. No. 16/680,739.

Office Action issued Oct. 21, 2021 in U.S. Appl. No. 17/306,231.

Office Action issued Oct. 21, 2021 in U.S. Appl. No. 17/335,845.

Office Action issued Sep. 9, 2021 in U.S. Appl. No. 16/768,909.

Second Declaration of Dr. Michael Sacks, Oct. 13, 2021, IPR2021-00383, U.S. Pat. No. 10,226,341, United States Patent and Trademark Office, Before the Patent Trial and Appeal Board, Cardiovalve Exhibit 2014 (28 pages total).

Transcript of Dr. Vesely, Sep. 22, 2021, Case No. IPR2021-00383, U.S. Pat. No. 10,226,341 United States Patent and Trademark Office Before the Patent Trial and Appeal Board, Cardiovalve Exhibit 2010 (170 pages total).

An Office Action dated Nov. 23, 2012, which issued during the prosecution of U.S. Appl. No. 13/033,852.

An Office Action dated Dec. 31, 2012, which issued during the prosecution of U.S. Appl. No. 13/044,694.

An Office Action dated Feb. 6, 2013, which issued during the prosecution of U.S. Appl. No. 13/412,814.

Langer F et al., "RING plus STRING: Papillary muscle repositioning as an adjunctive repair technique for ischemic mitral regurgitation," J Thorac Cardiovasc Surg 133:247-9, Jan. 2007.

Langer F et al., "RING+STRING: Successful repair technique for ischemic mitral regurgitation with severe leaflet tethering," Circulation 120[suppl 1]: S85-S91, Sep. 2009.

"Transcatheter Valve-in-Valve Implantation for Failed Bioprosthetic Heart Valves", J Webb et al., Circulation, Apr. 2010; 121: 1848-1857.

Jansen, J., Willeke, S., Reul, H. and Rum, G. (1992), Detachable Shape-Memory Sewing Ring for Heart Valves. Artificial Organs, 16:294-297. 1992 (an abstract).

Alexander S. Geha, et al., Replacement of degenerated mitral and aortic bioprostheses without explanation Ann Thorac Surg. Jun. 2001; 72:1509-1514.

An International Search Report and a Written Opinion both dated Oct. 13, 2011 which issued during the prosecution of Applicant's PCT/IL11/00231.

An Office Action dated Jul. 1, 2016, which issued during the prosecution of U.S. Appl. No. 14/161,921.

An International Search Report and a Written Opinion both dated Dec. 5, 2011, which issued during the prosecution of Applicant's PCT/IL11/00582.

An Office Action dated May 29, 2012, which issued during the prosecution of U.S. Appl. No. 12/840,463.

U.S. Appl. No. 61/555,160, filed Nov. 3, 2011.

U.S. Appl. No. 61/525,281, filed Aug. 19, 2011.

U.S. Appl. No. 61/537,276, filed Sep. 21, 2011.

U.S. Appl. No. 61/515,372, filed Aug. 5, 2011.

U.S. Appl. No. 61/492,449, filed Jun. 2, 2011.

U.S. Appl. No. 61/588,892, filed Jan. 20, 2012.

An International Search Report and a Written Opinion both dated Feb. 6, 2013, which issued during the prosecution of Applicant's PCT/IL12/00292.

An International Search Report and a Written Opinion both dated Feb. 6, 2013, which issued during the prosecution of Applicant's PCT/IL12/00293.

An Office Action dated Nov. 28, 2012, which issued during the prosecution of U.S. Appl. No. 12/961,721.

An Office Action dated Feb. 15, 2013, which issued during the prosecution of U.S. Appl. No. 12/840,463.

An Office Action dated Feb. 10, 2014, which issued during the prosecution of U.S. Appl. No. 13/033,852.

An Office Action dated Sep. 19, 2014, which issued during the prosecution of U.S. Appl. No. 13/044,694.

An International Search Report and a Written Opinion both dated Sep. 4, 2014 which issued during the prosecution of Applicant's PCT/IL2014/050087.

Invitation to Pay Additional Fees dated Jun. 12, 2014 PCT/IL2014/050087.

(56)     References Cited

OTHER PUBLICATIONS

An Office Action dated Jun. 17, 2014, which issued during the prosecution of U.S. Appl. No. 12/961,721.
An Office Action dated Jul. 3, 2014, which issued during the prosecution of U.S. Appl. NO. 13/033,852.
An Office Action dated May 23, 2014, which issued during the prosecution of U.S. Appl. No. 13/412,814.
Dominique Himbert; Mitral Regurgitation and Stenosis from Bioprosthesis and Annuloplasty Failure: Transcatheter approaches and outcomes, 24 pages Oct. 28, 2013.
An International Search Report and a Written Opinion both dated Mar. 17, 2014 which issued during the prosecution of Applicant's PCT/IL2013/050937.
An International Preliminary Report on patentability dated Dec. 2, 2013, which issued during the prosecution of Applicant's PCT/IL11/00582.
An Office Action dated Sep. 12, 2013, which issued during the prosecution of U.S. Appl. No. 13/412,814.
An Office Action dated Aug. 2, 2013, which issued during the prosecution of U.S. Appl. No. 13/033,852.
An Internatioanl Preliminary Report on patentability dated Sep. 11, 2012, which issued during the prosecution of Applicant's PCT/IL2011/000231.
An Office Action dated Jul. 2, 2014, which issued during the prosecution of U.S. Appl. No. 13/811,308.
An Office Action dated Jan. 20, 2016, which issued during the prosecution of U.S. Appl. No. 14/161,921.
An Office Action dated Jul. 23, 2013, which issued during the prosecution of U.S. Appl. No. 12/961,721.
An Office Action dated Jul. 18, 2013, which issued during the prosecution of U.S. Appl. No. 13/044,694.
An Office Action dated Nov. 8, 2013, which issued during the prosecution of U.S. Appl. No. 12/840,463.
An Office Action dated Jun. 4, 2014, which issued during the prosecution of U.S. Appl. No. 12/840,463.
An Office Action dated Aug. 13, 2012, which issued during the prosecution of U.S. Appl. No. 13/044,694.
An Office Action dated Jul. 2, 2012, which issued during the prosecution of U.S. Appl. No. 13/033,852.
An Office Action dated Feb. 3, 2014, which issued during the prosecution of U.S. Appl. No. 13/811,308.
An International Preliminary Report on patentability dated Feb. 11, 2014, which issued during the prosecution of Applicant's PCT/IL12/00292.
An International Preliminary Report on patentability dated Feb. 11, 2014, which issued during the prosecution of Applicant's PCT/IL12/00293.
A Notice of Allowance dated Aug. 15, 2014, which issued during the prosecution of U.S. Appl. No. 13/412,814.
An Office Action dated Aug. 14, 2012, which issued during the prosecution of U.S. Appl. No. 12/961,721.
U.S. Appl. No. 61/283,819, filed Dec. 8, 2009.
Notice of Allowance dated Apr. 8, 2016, which issued during the prosecution of U.S. Appl. No. 14/237,258.
U.S. Appl. No. 61/756,034, filed Jan. 24, 2013.
U.S. Appl. No. 61/756,049, filed Jan. 24, 2013.
An International Preliminary Report on Patentability dated Jan. 31, 2017, which issued during the prosecution of Applicant's PCT/IL2015/050792.
U.S. Appl. No. 62/372,861, filed Aug. 10, 2016.
Notice of Allowance dated Aug. 13, 2018, which issued during the prosecution of U.S. Appl. No. 15/995,597.
Notice of Allowance dated Apr. 20, 2018, which issued during the prosecution of U.S. Appl. No. 15/878,206.
An Office Action dated Dec. 10, 2015, which issued during the prosecutino of U.S. Appl. No. 14/237,258.
An International Preliminary Report on Patentability dated Jul. 28, 2015, which prosecution of Applicant's PCT/IL2014/050087.
An Office Action dated Nov. 27, 2015, which issued during the prosecution of U.S. Appl. No. 14/626,267.

An Office Action dated Jan. 21, 2016, which issued during the prosecution of U.S. Appl. No. 14/237,264.
An Office Action dated Jan. 30, 2015, which issued during the prosecution of UK Patent Application No. 1413474.6.
An International Search Report and a Written Opinion both dated May 30, 2016, which issued during the prosecution of Applicant's PCT/IL2016/050125.
An Office Action dated Sep. 26, 2016, which issued during the prosecution of U.S. Appl. No. 14/763,004.
An Office Action dated Jan. 18, 2017, which issued during the prosecution of U.S. Appl. No. 14/626,267.
An Office Action dated Feb. 7, 2017, which issued during the prosecution of U.S. Appl. No. 14/689,608.
An Office Action dated Feb. 8, 2017, which issued during the prosecution of UK Patent Application No. 1613219.3.
An Office Action together dated Feb. 10, 2017, which issued during the prosecution of European Patent Application No. 12821522.5.
An International Search Report and a Written Opinion both dated Oct. 27, 2015, which issued during the prosecution of Applicant's PCT/IL2015/050792.
European Search Report dated Feb. 18. 2015, which issued during the prosecution of Applicant's European App No. 12821522.5.
Saturn Project—a novel solution for transcatheter heart valve replacement specifically designed to address clinical therapeutic needs on mitral valve: Dec. 2016.
Righini presentation EuroPCR May 2015 (Saturn)—(downloaded from: https://www.pcronline.com/Cases-resourcesimages/Resources/Course-videos-slides/2015/Cardiovascularinnovation-pipeline-Mitral-and-tricuspid-valve-interventions).
An Advisory Action dated Apr. 2, 2018, which issued during the prosecution of U.S. Appl. No. 14/763,004.
An Office Action dated Jul. 26, 2018, which issued during the prosecution of U.S. Appl. No. 15/872,501.
An Office Action dated May 4, 2018, which issued during the prosecution of U.S. Appl. No. 15/872,501.
An Office Action dated Apr. 20, 2018, which issued during the prosecution of U.S. Appl. No. 15/886,517.
An Office Action dated Aug. 9, 2018, which issued during the prosecution of U.S. Appl. No. 15/899,858.
An Office Action dated Aug. 9, 2018, which issued during the prosecution of U.S. Appl. No. 15/902,403.
An Office Action dated Jun. 28, 2018, which issued during the prosecution of Design U.S. Appl. No. 29/635,658.
An Office Action dated Jun. 28, 2018, which issued during the prosecution of Design U.S. Appl. No. 29/635,661.
Georg Lutter, MD, et al; "Percutaneous Valve Replacement: Current State and Future Prospects", The Annals of Thoracic Surgery ; vol. 78, pp. 2199-2206; Dec. 2004.
An Office Action dated Jun. 6, 2018, which issued during the prosecution of UK Patent Application No. 1720803.4.
An International Search Report and a Written Opinion both dated Jun. 20, 2018, which issued during the prosecution of Applicant's PCT/IL2018/050024.
An Office Action dated Jun. 18, 2018, which issued during the prosecution of UK Patent Application No. 1800399.6.
An Office Action dated Oct. 23, 2017, which issued during the prosecution of U.S. Appl. No. 14/763,004.
An Office Action dated Dec. 7, 2017, which issued during the prosecution of U.S. Appl. No. 15/213,791.
Interview Summary dated Feb. 8, 2018, which issued during the prosecution of U.S. Appl. No. 15/213,791.
An Office Action dated Feb. 7, 2018, which issued during the prosecution of U.S. Appl. No. 15/197,069.
An International Search Report and a Written Opinion both dated Nov. 24, 2017, which issued during the prosecution of Applicant's PCT/IL2017/050873.
An Office Action dated Jan. 5, 2018, which issued during the prosecution of U.S. Appl. No. 15/541,783.
An Office Action dated Feb. 2, 2018, which issued during the prosecution of U.S. Appl. No. 15/329,920.
An Invitation to pay additional fees dated Jan. 2, 2018, which issued during the prosecution of Applicant's PCT/IL2017/050849.

(56)            References Cited

OTHER PUBLICATIONS

An Invitation to pay additional fees dated Sep. 29, 2017, which issued during the prosecution of Applicant's PCT/IL2017/050873.
European Search Report dated Jun. 29, 2017, which issued during the prosecution of Applicant's European App No. 11809374.9.
An Invitation to pay additional fees dated Oct. 11, 2018, which issued during the prosecution of Applicant's PCT/IL2018/050725.
An Office Action dated Dec. 4, 2018, which issued during the prosecution of U.S. Appl. No. 16/045,059.
An Office Action together with the English translation dated Nov. 5, 2018 which issued during the prosecution of Chinese Patent Application No. 201680008328.5.
Notice of Allowance dated Sep. 25, 2018, which issued during the prosecution of U.S. Appl. No. 15/188,507.
European Search Report dated Sep. 26, 2018 which issued during the prosecution of Applicant's European App No. 18186784.7.
An Office Action dated Jun. 30, 2015, which issued during the prosecution of U.S. Appl. No. 14/522,987.
Notice of Allowance dated Dec. 13, 2013, which issued during the prosecution of U.S. Appl. No. 13/675,119.
An International Preliminary Report on Patentability dated Aug. 8, 2017, which issued during the prosecution of Applicant's PCT/IL2016/050125.
An Office Action dated Jan. 17, 2018, which issued during the prosecution of U.S. Appl. No. 14/763,004.
An Office Action dated Mar. 25, 2015, which issued during the prosecution of U.S. Appl. No. 12/840,463.
An Office Action dated Feb. 25, 2016, which issued during the prosecution of U.S. Appl. No. 14/522,987.
An Office Action dated Apr. 13, 2016, which issued during the prosecution of U.S. Appl. No. 14/626,267.
An Office Action dated Aug. 28, 2015, which issued during the prosecution of U.S. Appl. No. 14/237,264.
Maisano (2015) TCR presentation re Cardiovalve.
Notice of Allowance dated Sep. 29, 2016, which issued during the prosecution of U.S. Appl. No. 14/442,541.
Notice of Allowance dated May 10, 2016, which issued during the prosecution of U.S. Appl. No. 14/237,258.
Notice of Allowance dated May 20, 2016, which issued during the prosecution of U.S. Appl. No. 14/237,258.
An International Preliminary Report on Patentability dated May 19. 2015, which issued during the prosecution of Applicant's PCT/IL2013/050937.
Dusan Pavcnik, MD, PhD2, et al; "Development and Initial Experimental Evaluation of a Prosthetic Aortic Valve for Transcatheter Placement", Cardiovascular Radiology. Radiology Apr. 1992, vol. 183, pp. 151-154.
Notice of Allowance dated Oct. 16, 2013, which issued during the prosecution of U.S. Appl. No. 13/675,119.
Notice of Allowance dated Feb. 11, 2015, which issued during the prosecution of U.S. Appl. No. 13/033,852.
Notice of Allowance dated May 5, 2015, which issued during the prosecution of U.S. Appl. No. 12/840,463.
Notice of Allowance dated Mar. 10, 2015, which issued during the prosecution of U.S. Appl. No. 13/811,308.
Notice of Allowance dated Jul. 1, 2016, which issued during the prosecution of U.S. Appl. No. 14/442,541.
An Office Action dated Mar. 25, 2019, which issued during the prosecution of European Patent Application No. 14710060.6.
An International Search Report and a Written Opinion both dated Nov. 9, 2018, which issued during the prosecution of Applicant's PCT/IL2018/050869.
An International Search Report and a Written Opinion both dated Dec. 5, 2018, which issued during the prosecution of Applicant's PCT/IL2018/050725.
An International Search Report and a Written Opinion both dated Apr. 25, 2019, which issued during the prosecution of Applicant's PCT/IL2019/050142.

An International Preliminary Report on Patentability dated Feb. 12, 2019, which issued during the prosecution of Applicant's PCT/IL2017/050873.
An Office Action dated Sep. 13, 2019, which issued during the prosecution of U.S. Appl. No. 16/460,313.
An Office Action dated Nov. 26, 2019, which issued during the prosecution of U.S. Appl. No. 16/532,945.
An Office Action dated Aug. 16, 2019, which issued during the prosecution of U.S. Appl. No. 15/668,659.
An Office Action dated Nov. 1, 2019, which issued during the prosecution of U.S. Appl. No. 15/872,501.
An Office Action dated Jun. 14, 2019, which issued during the prosecution of U.S. Appl. No. 15/703,385.
An Office Action dated Oct. 4, 2019, which issued during the prosecution of U.S. Appl. No. 16/183,140.
An Office Action dated Jun. 13, 2019, which issued during the prosecution of U.S. Appl. No. 16/388,038.
An International Preliminary Report on Patentability dated Feb. 4, 2020, which issued during the prosecution of Applicant's PCT/IL2018/050725.
An International Search Report and a Written Opinion both dated Jan. 25, 2019, which issued during the prosecution of Applicant's PCT/IL2018/051122.
An International Search Report and a Written Opinion both dated May 13, 2019, which issued during the prosecution of Applicant's PCT/IL2018/051350.
An International Preliminary Report on Patentability dated Feb. 5, 2019, which issued during the prosecution of Applicant's PCT/IL2017/050849.
An Office Action dated Oct. 25, 2018, which issued during the prosecution of U.S. Appl. No. 14/763,004.
An Office Action dated Mar. 4, 2019, which issued during the prosecution of U.S. Appl. No. 14/763,004.
An Office Action dated Jan. 9, 2019, which issued during the prosecution of U.S. Appl. No. 15/329,920.
An Office Action dated Jan. 30, 2019, which issued during the prosecution of U.S. Appl. No. 15/872,501.
An Office Action dated Feb. 5, 2019, which issued during the prosecution of U.S. Appl. No. 15/899,858.
An Office Action dated May 23, 2019, which issued during the prosecution of U.S. Appl. No. 15/668,659.
An Office Action dated May 1, 2019, which issued during the prosecution of U.S. Appl. No. 15/691,032.
An Office Action dated Aug. 1, 2019, which issued during the prosecution of U.S. Appl. No. 15/668,559.
An Office Action dated Jun. 19, 2019, which issued during the prosecution of U.S. Appl. No. 15/682,789.
Notice of Allowance dated Jan. 13, 2020, which issued during the prosecution of U.S. Appl. No. 15/956,956.
An Office Action dated Jun. 25, 2019, which issued during the prosecution of U.S. Appl. No. 15/329,920.
An Office Action dated May 16, 2019, which issued during the prosecution of U.S. Appl. No. 15/433,547.
U.S. Appl. No. 62/560,384, filed Sep. 19, 2017.
U.S. Appl. No. 62/112,343, filed Feb. 5, 2015.
An International Preliminary Report on Patentability dated Feb. 11, 2020, which issued during the prosecution of Applicant's PCT/IL2018/050869.
An International Preliminary Report on Patentability dated Oct. 20, 2020, which issued during the prosecution of Applicant's PCT/IL2019/050142.
An Office Action dated Jan. 6, 2020, which issued during the prosecution of U.S. Appl. No. 16/660,231.
An Office Action dated Dec. 31. 2019, which issued during the prosecution of U.S. Appl. No. 16/183,140.
Notice of Allowance dated Apr. 24, 2019, which issued during the prosecution of U.S. Appl. No. 16/045,059.
An Office Action dated Jan. 14, 2020, which issued during the prosecution of U.S. Appl. No. 16/284,331.
European Search Report dated Mar. 5, 2020 which issued during the prosecution of Applicant's European App No. 17752184.6.
European Search Report dated Mar. 4, 2020 which issued during the prosecution of Applicant's European App No. 16706913.7.

(56) References Cited

OTHER PUBLICATIONS

Notice of Allowance dated Mar. 12, 2020, which issued during the prosecution of U.S. Appl. No. 16/460,313.
An Office Action dated Jan. 9, 2020, which issued during the prosecution of U.S. Appl. No. 15/600,190.
An Office Action dated Jan. 3, 2020, which issued during the prosecution of U.S. Appl. No. 16/678,355.
An Office Action dated Feb. 6, 2020, which issued during the prosecution of U.S. Appl. No. 15/668,659.
Notice of Allowance dated Jan. 16, 2020, which issued during the prosecution of U.S. Appl. No. 16/532,945.
Notice of Allowance dated Aug. 19, 2020, which issued during the prosecution of U.S. Appl. No. 16/637,166.
Notice of Allowance dated Jul. 27, 2020, which issued during the prosecution of U.S. Appl. No. 16/637,166.
Notice of Allowance dated Jun. 23, 2020, which issued during the prosecution of U.S. Appl. No. 16/637,166.
Notice of Allowance dated May 7, 2020, which issued during the prosecution of U.S. Appl. No. 16/637,166.
Sündermann, Simon H., et al. "Feasibility of the Engager™ aortic transcatheter valve system using a flexible over-the-wire design." European Journal of Cardio-Thoracic Surgery 42.4 (2012): e48-e52.
An Office Action summarized English translation and Search Report dated Jul. 3, 2020, which issued during the prosecution of Chinese Patent Application No. 201780061210.3.
Serruys, P. W., Piazza, N., Cribier, A., Webb, J., Laborde, J. C., & de Jaegere, P. (Eds.). (2009). Transcatheter aortic valve implantation: tips and tricks to avoid failure. CRC Press.—Screenshots from Google Books downloaded from: https://books.google.co.il/books?id=FLzLBQAAQBAJ&lpg=PA198&ots=soqWrDH-y_&dq=%20%22Edwards%20SAPIEN%22&lr&pg=PA20#y=onepage&q=%22Edwards%20SAPIEN%22&f=false ; Downloaded on Jun. 18, 2020.
An International Search Report and a Written Opinion both dated Jun. 24, 2020, which issued during the prosecution of Applicant's PCT/IL2019/051398.
An Office Action dated Jul. 14, 2020, which issued during the prosecution of U.S. Appl. No. 16/324,339.
Notice of Allowance dated Aug. 28, 2020, which issued during the proseuction of U.S. Appl. No. 16/324,339.
Notice of Allowance dated Jul. 29, 2020, which issued during the prosecution of U.S. Appl. No. 16/132,937.
An Office Action dated Jul. 29, 2020, which issued during the prosecution of U.S. Appl. No. 16/269,328.
Notice of Allowance dated Aug. 26, 2020, which issued during the proseuction of U.S. Appl. No. 16/269,328.
An Office Action dated Aug. 7, 2020, which issued during the prosecution of U.S. Appl. No. 15/668,659.
Tchetche, D. and Nicolas M. Van Mieghem: "New-generation TAVI devices: description and specifications" EuroIntervention, 2014, No. 10:U90-U100.
An Office Action dated Aug. 23, 2019, which issued during the prosecution of U.S. Appl. No. 15/600,190.
Symetis S.A.: "ACURATE neo™ Aortic Bioprosthesis for Implantation using the ACURATE neo™ TA Transapical Delivery System in Patients with Severe Aortic Stenosis," Clinical Investigation Plan, Protocol No. 2015-01, Vs. No. 2,2015:1-76.
Notice of Allowance dated Sep. 10, 2020, which issued during the prosecution of U.S. Appl. No. 15/600,190.
Notice of Allowance dated Sep. 10, 2020, which issued during the prosecution of U.S. Appl. No. 16/324,339.
Notice of Allowance dated Oct. 19, 2020, which issued during the prosecution of U.S. Appl. No. 16/324,339.
Notice of Allowance dated Sep. 21, 2020, which issued during the prosecution of U.S. Appl. No. 16/269,328.
Notice of Allowance dated Oct. 28, 2020, which issued during the prosecution of U.S. Appl. No. 16/269,328.
Notice of Allowance dated Jan. 16, 2020, which issued during the prosecution of U.S. Appl. No. 15/872,501.

An Office Action dated May 11, 2020, which issued during the prosecution of U.S. Appl. No. 16/811,732.
An Office Action dated Sep. 24, 2020, which issued during the prosecution of U.S. Appl. No. 16/811,732.
Notice of Allowance dated Mar. 29, 2017, which issued during the prosecution of U.S. Appl. No. 14/161,921.
Agarwal et al. International Cardiology Perspective Functional Tricuspid Regurgitation, Circ Cardiovasc Interv 2009;2;2;565-573 (2009).
Alfieri et al., "An effective technique to correct anterior mitral leaflet prolapse," J Card 14(6):468-470 (1999).
Alfieri et al., "The double orifice technique in mitral valve repair: a simple solution for complex problems," Journal of Thoracic Cardiovascular Surgery 122:674-681 (2001).
Alfieri, "The edge-to-edge repair of the mitral valve," [Abstract] 6th Annual NewEra Cardiac Care: Innovation & Technology, Heart Surgery Forum pp. 103. (2000).
Alfieri et al."Novel Suture Device for Beating-Heart Mitral Leaflet Approximation", Ann Thorac Surg. 2002, 74:1488-1493.
Alfieri et al., "The edge to edge technique," The European Association for Cardio-Thoracic Surgery 14th Annual Meeting Oct. 7-11, Book of Procees. (2000).
Amplatzer Cardiac Plug brochure (English pages), AGA Medical Corporation (Plymouth, MN) (copyright 2008-2010, downloaded Jan. 11, 2011).
An Amplatzer® Cribriform Occluder. A patient guide to Percutaneous, Transcatheter, Atrial Septal Defect Closuer, AGA Medical Corporation, Apr. 2008.
An Amplatzer® Septal Occluder. A patient guide to the Non-Surgical Closuer of the Atrial Septal Defect Using the AMPLATZER Septal Occluder System, AGA Medical Corporation, Apr. 2008.
Brennan, Jennifer, 510(k) Summary of safety and effectiveness, Jan. 2008.
Dictionary.com definition of "lock", Jul. 29, 2013.
Dang NC et al. "Simplified Placement of Multiple Artificial Mitral Valve Chords," The Heart Surgery Forum #2005-1005, 8 (3) (2005).
Maisano, The double-orifice technique as a standardized approach to treat mitral . . . , European Journal of Cardio-thoracic Surgery 17 (2000) 201-205.
"Two dimensional real-time ultrasonic imaging of the heart and great vessels", Mayo Clin Proc. vol. 53:271-303, 1978.
Odell JA et al., "Early Results 04yf a Simplified Method of Mitral Valve Annuloplasty," Circulation 92:150-154 (1995).
O'Reilly S et al., "Heart valve surgery pushes the envelope," Medtech Insight 8(3): 73, 99-108 (2006).
Swain CP et al., "An endoscopically deliverable tissue-transfixing device for securing biosensors in the gastrointestinal tract," Gastrointestinal Endoscopy 40(6): 730-734 (1994).
An Invitation to pay additional fees dated Jan. 31, 2014, which issued during the prosecution of Applicant's PCT/IL2013/050860.
U.S. Appl. No. 62/030,715, filed Jul. 30, 2014.
U.S. Appl. No. 62/139,854, filed Mar. 30, 2015.
U.S. Appl. No. 61/312,412, filed Mar. 10, 2010.
An Invitation to pay additional fees dated Jan. 31, 2014, which issued during the prosecution of Applicant's PCT/IL2013/050861.
An International Preliminary Report on Patentability dated Dec. 23. 2013, which issued during the prosecution of Applicant's PCT/IL2012/000250.
An International Preliminary Report on Patentability dated Sep. 18, 2007, which issued during the prosecution of Applicant's PCT/IL2006/000342.
An International Preliminary Report on Patentability dated Jun. 5, 2012, which issued during the prosecution of Applicant's PCT/IL2010/001024.
An International Preliminary Report on Patentability dated Apr. 28, 2015, which issued during the prosecution of Applicant's PCT/IL2013/050861.
An International Preliminary Report on Patentability dated Apr. 26, 2016, which issued during the prosecution of Applicant's PCT/IL2014/050914.
An International Preliminary Report on Patentability dated Jun. 10, 2009, which issued during the prosecution of Applicant's PCT/IL07/01503.

(56) References Cited

OTHER PUBLICATIONS

An International Preliminary Report on Patentability dated Dec. 18, 2010, which issued during the prosecution of Applicant's PCT/IL09/00593.
An International Preliminary Report on Patentability dated Jun. 29, 2011, which issued during the prosecution of Applicant's PCT/IL2009/001209.
Notice of Allowance dated Aug. 18, 2017, which issued during the prosecution of U.S. Appl. No. 14/689,608.
Notice of Allowance dated Jul. 6, 2017, which issued during the prosecution of U.S. Appl. No. 14/689,608.
Notice of Allowance dated May 22, 2017, which issued during the prosecution of U.S. Appl. No. 14/689,608.
An Office Action dated Apr. 21, 2017, which issued during the prosecution of U.S. Appl. No. 15/213,791.
An Office Action dated Sep. 29, 2017, which issued during the prosecution of U.S. Appl. No. 15/197,069.
An International Preliminary Report on Patentability dated Nov. 9, 2011, which issued during the prosecution of Applicant's PCT/IL2010/000357.
An International Preliminary Report on Patentability dated Nov. 9, 2011 which issued during the prosecution of Applicant's PCT/IL2010/000358.
An International Preliminary Report on Patentability dated Nov. 27, 2012, which issued during the prosecution of Applicant's PCT/IL2011/000404.
An International Preliminary Report on Patentability dated Feb. 4, 2014, which issued during the prosecution of Applicant's PCT/IL2011/000446.
An International Preliminary Report on Patentability dated Jan. 29, 2013, which issued during the prosecution of Applicant's PCT/IL2011/000600.
An International Preliminary Report on Patentability dated Dec. 23, 2014, which issued during the prosecution of Applicant's PCT/IL2012/050451.
A Notice of Allowance dated Jul. 30, 2015, which issued during the prosecution of U.S. Appl. No. 13/319,007.
An Office Action dated Sep. 29, 2014, which issued during the prosecution of U.S. Appl. No. 13/504,870.
An Office Action dated Jan. 13, 2015, which issued during the prosecution of U.S. Appl. No. 13/707,013.
An Office Action dated Mar. 23, 2015, which issued during the prosecution of U.S. Appl. No. 13/707,013.
Notice of Allowance dated Mar. 25, 2015, which issued during the prosecution of U.S. Appl. No. 13/749,153.
An Office Action dated Oct. 3, 2014, which issued during the prosecution of U.S. Appl. No. 13/749,153.
Notice of Allowance dated May 22, 2015, which issued during the prosecution of U.S. Appl. No. 13/749,153.
Notice of Allowance dated Aug. 3, 2015, which issued during the prosecution of U.S. Appl. No. 13/749,153.
An Office Action dated Dec. 19, 2013, which issued during the prosecution of U.S. Appl. No. 14/027,934.
An Office Action dated Jun. 11, 2014, which issued during the prosecution of U.S. Appl. No. 14/027,934.
An Office Action dated Aug. 22, 2014, which issued during the prosecution of U.S. Appl. No. 14/027,934.
An Office Action dated Apr. 2, 2015, which issued during the prosecution of U.S. Appl. No. 14/027,934.
An Office Action dated Jan. 5, 2016, which issued during the prosecution of U.S. Appl. No. 14/027,934.
An Office Action dated Jan. 5, 2016, which issued during the prosecution of U.S. Appl. No. 14/084,426.
An Office Action dated Mar. 16, 2015, which issued during the prosecution of U.S. Appl. No. 14/084,426.
An Office Action dated Jan. 6, 2016, which issued during the prosecution of U.S. Appl. No. 14/128,756.
An Office Action dated May 11, 2016, which issued the prosecution of U.S. Appl. No. 14/128,756.

Notice of Allowance dated Oct. 20, 2015, which issued during the prosecution of U.S. Appl. No. 12/996,954.
Notice of Allowance dated Feb. 19, 2014, which issued during the prosecution of U.S. Appl. No. 12/795,192.
An Office Action dated Jul. 20, 2012, which issued during the prosecution of U.S. Appl. No. 12/843,412.
An Office Action dated Mar. 27, 2013, which issued during the prosecution of U.S. Appl. No. 12/843,412.
A Restriction Requirement dated May 1, 2012, which issued during the prosecution of U.S. Appl. No. 12/843,412.
A Notice of Allowance dated May 2, 2013, which issued during the prosecution of U.S. Appl. No. 12/843,412.
A Restriction Requirement dated Nov. 19, 2012, which issued during the prosecution of U.S. Appl. No. 12/926,673.
An Office Action dated Feb. 12, 2013, which issued during the prosecution of U.S. Appl. No. 12/926,673.
An Office Action dated Oct. 22, 2013, which issued during the prosecution of U.S. Appl. No. 12/926,673.
A Notice of Allowance dated Jan. 7, 2014, which issued during the prosecution of U.S. Appl. No. 12/926,673.
An Office Action dated Oct. 9, 2013, which issued during the prosecution of U.S. Appl. No. 12/996,954.
An Office Action dated Mar. 24, 2015, which issued during the prosecution of U.S. Appl. No. 12/996,954.
An Office Action dated Oct. 5, 2012, which issued during the prosecution of U.S. Appl. No. 12/996,954.
Notice of Allowance dated Jul. 7, 2015, which issued during the prosecution of U.S. Appl. No. 12/996,954.
An Office Action dated Nov. 16, 2018, which issued during the prosecution of U.S. Appl. No. 16/042,028.
An International Search Report with Written Opinion both dated Feb. 2, 2012, which issued during the prosecution of Applicant's PCT/IL2011/000600.
An International Search Report together with Written Opinion both dated Mar. 30, 2011, which issued during the prosecution of Applicant's PCT/IL2010/001024.
An International Search Report and A Written Opinion both dated Feb. 10, 2011, which issued during the prosecution of Applicant's PCT/IL10/00890.
An Office Action dated May 28, 2015, which issued during the prosecution of U.S. Appl. No. 14/128,756.
An Office Action dated Sep. 6, 2018, which issued during the prosecution of U.S. Appl. No. 15/994,022.
An Office Action dated Sep. 7, 2018, which issued during the prosecution of U.S. Appl. No. 15/995,725.
An Office Action dated Nov. 26, 2018, which issued during the prosecution of U.S. Appl. No. 16/040,831.
An Office Action dated Jul. 11. 2018, which issued during the prosecution of U.S. Appl. No. 15/978,494.
An Office Action dated Nov. 23, 2018, which issued during the prosecution of U.S. Appl. No. 16/041,208.
An Office Action dated Jun. 15, 2018, which issued during the prosecution of U.S. Appl. No. 15/970,314.
An Office Action dated Oct. 12, 2018, which issued during the prosecution of U.S. Appl. No. 15/970,314.
An Office Action dated Jul. 26, 2018, which issued during the prosecution of U.S. Appl. No. 15/979,686.
An Office Action dated Sep. 10, 2018, which issued during the prosecution of U.S. Appl. No. 16/008,618.
An International Preliminary Report on Patentability dated Apr. 28, 2015, which issued during the prosecution of Applicant's PCT/IL2013/050860.
An Office Action dated Apr. 22, 2019, which issued during the prosecution of U.S. Appl. No. 15/668,559.
Notice of Allowance dated Aug. 30, 2019, which issued during the prosecution of U.S. Appl. No. 15/682,789.
Notice of Allowance dated Mar. 29, 2019, which issued during the prosecution of U.S. Appl. No. 15/541,783.
Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).

(56) References Cited

OTHER PUBLICATIONS

An Advisory Action dated Dec. 13, 2013, which issued during the prosecution of U.S. Appl. No. 12/961,721.
An Office Action dated Aug. 7, 2015, which issued during the prosecution of U.S. Appl. No. 14/128,756.
An Office Action dated May 19, 2011, which issued during the prosecution of U.S. Appl. No. 12/706,868.
An Office Action dated Sep. 1, 2011, which issued during the prosecution of U.S. Appl. No. 12/706,868.
An Office Action dated May 30, 2012, which issued during the prosecution of U.S. Appl. No. 12/706,868.
A Notice of Allowance dated Sep. 18, 2012, which issued during the prosecution of U.S. Appl. No. 12/706,868.
Restriction Requirement dated May 5, 2011, which issued during the prosecution of U.S. Appl. No. 12/706,868.
A Restriction Requirement dated Mar. 30, 2012, which issued during the prosecution of U.S. Appl. No. 12/785,717.
An Office Action dated Oct. 5, 2020, which issued during the prosecution of Canadian Patent Application No. 2,973,940.
An Office Action dated Nov. 30, 2020, which issued during the prosecution of U.S. Appl. No. 16/138,129.
An Office Action summarized English translation and Search Report dated Nov. 25, 2020, which issued during the prosecution of Chinese Patent Application No. 201910449820.1.
Notice of Allowance dated Nov. 19, 2020, which issued during the prosecution of U.S. Appl. No. 16/318,025.
An Office Action dated Aug. 2, 2011, which issued during the prosecution of U.S. Appl. No. 12/435,291.
Notice of Allowance dated Dec. 7, 2011, which issued during the prosecution of U.S. Appl. No. 12/435,291.
An Office Action dated Apr. 6, 2010, which issued during the prosecution of Applicant's U.S. Appl. No. 12/484,512.
An Office Action dated Oct. 6, 2010, which issued during the prosecution of Applicant's U.S. Appl. No. 12/484,512.
Notice of Allowance dated Apr. 20, 2011, which issued during the prosecution of U.S. Appl. No. 12/484,512.
Notice of Allowance dated Mar. 23, 2011, which issued during the prosecution of U.S. Appl. No. 12/484,512.
An Office Action dated Jan. 27, 2012, which issued during the prosecution of U.S. Appl. No. 12/548,991.
An Office Action dated Aug. 6, 2012, which issued during the prosecution of U.S. Appl. No. 12/548,991.
An Advisory Action dated Sep. 6, 2012 which issued during the prosecution of U.S. Appl. No. 12/548,991.
Notice of Allowance dated Jun. 23, 2014, which issued during the prosecution of U.S. Appl. No. 12/548,991.
A Restriction Requirement dated Nov. 14, 2011 which issued during the prosecution of U.S. Appl. No. 12/548,991.
Amendment, Terminal Disclaimer and Extension dated Jun. 27, 2012, which issued during the prosecution of U.S. Appl. No. 12/548,991.
A Restriction Requirement dated Jul. 05. 2012, which issued during the prosecution of U.S. Appl. No. 12/563,930.
An Office Action dated Apr. 2, 2013, which issued during the prosecution of U.S. Appl. No. 12/785,717.
An Office Action dated Dec. 27, 2013, which issued during the prosecution of U.S. Appl. No. 12/785,717.
An Office Action dated Nov. 5, 2012, which issued during the prosecution of U.S. Appl. No. 12/795,026.
An Office Action dated May 10, 2012, which issued during the prosecution of U.S. Appl. No. 12/795,026.
Notice of Allowance dated Nov. 13, 2014, which issued during the prosecution of U.S. Appl. No. 12/795,026.
Notice of Allowance dated Dec. 24, 2014, which issued during the prosecution of U.S. Appl. No. 12/795,026.
A Restriction Requirement dated Jan. 6, 2012, which issued during the prosecution of U.S. Appl. No. 12/795,026.
A Restriction Requirement dated Sep. 14, 2012, which issued during the prosecution of U.S. Appl. No. 12/795,192.

An Office Action dated Aug. 15, 2013, which issued during the prosecution of U.S. Appl. No. 12/795,192.
An Office Action dated Jan. 17. 2013, which issued during the prosecution of U.S. Appl. No. 12/795,192.
Notice of Allowance dated Nov. 19, 2013, which issued during the prosecution of U.S. Appl. No. 12/795,192.
A Notice of Allowance dated Jun. 26, 2012, which issued during the prosecution of U.S. Appl. No. 12/608,316.
An Office Action dated Nov. 14. 2011, which issued during the prosecution of U.S. Appl. No. 12/608,316.
A Restriction Requirement dated Apr. 1, 2011, which issued during the prosecution of U.S. Appl. No. 12/608,316.
An Office Action dated Jul. 6, 2012, which issued during the prosecution of U.S. Appl. No. 12/692,061.
An Office Action dated Jan. 23, 2012, which issued during the prosecution of U.S. Appl. No. 12/692,061.
An Office Action dated Mar. 9, 2012, which issued during the prosecution of U.S. Appl. No. 12/689,635.
An Office Action dated Nov. 30, 2012, which issued during the prosecution of U.S. Appl. No. 12/689,635.
A Notice of Allowance dated May 22. 2013, which issued during the prosecution of U.S. Appl. No. 12/689,635.
Restriction Requirement dated Nov. 14, 2011, which issued during the prosecution of U.S. Appl. No. 12/689,635.
An Office Action dated May 6, 2013, which issued during the prosecution of U.S. Appl. No. 12/689,693.
An Office Action dated Feb. 3, 2014, which issued during the prosecution of U.S. Appl. No. 12/689,693.
Notice of Allowance dated Jun. 11, 2014, which issued during the prosecution of U.S. Appl. No. 12/689,693.
A Restriction Requirement dated Sep. 17, 2012, which issued during the prosecution of U.S. Appl. No. 12/689,693.
A Notice of Allowance dated Sep. 3, 2014, which issued during the prosecution of U.S. Appl. No. 12/689,693.
European Search Report dated Jul. 8, 2016, which issued during the prosecution of Applicant's European App No. 13849843.1.
A Supplementary European Search Report dated Dec. 4, 2012, which issued during the prosecution of European Patent Application No. EP 09834225.6.
A Supplementary European Search Report dated Mar. 28, 2013, which issued during the prosecution of European Patent Application No. EP 1077 2091.4.
Search Report in European Patent Application 10772090.6 dated Jan. 17, 2014.
Supplementary European Search Report dated Oct. 23, 2014 which issued during the prosecution of Applicant's European App No. 10826224.7.
Notice of Allowance dated May 6, 2016, which issued during the prosecution of U.S. Appl. No. 14/667,090.
Notice of Allowance dated Apr. 12, 2016, which issued during the prosecution of U.S. Appl. No. 14/667,090.
An Office Action dated Jun. 7, 2013 which issued during the prosecution of U.S. Appl. No. 13/141,606.
An Office Action dated Jun. 13, 2014, which issued during the prosecution of U.S. Appl. No. 13/141,606.
Notice of Allowance dated Sep. 29, 2014, which issued during the prosecution of U.S. Appl. No. 13/141,606.
An Office Action dated Feb. 4, 2013 which issued during prosecution of U.S. Appl. No. 13/141,606.
An English translation of an Office Action dated Apr. 23, 2014 which issued during the prosecution of Chinese Patent Application No. 201080059948.4.
Communication dated Jul. 24, 2014, issued by the State Intellectual Property Office of the P.R. of China in counterpart Application No. 200980157331.3.
An International Search Report and a Written Opinion both dated Jan. 25, 2016, which issued during the prosecution of Applicant's PCT/IL2015/051027.
An International Search Report dated May 19, 2011, which issued during the prosecution of Applicant's PCT/IL2011/00064.
An International Search Report and a Written Opinion both dated Feb. 22, 2013, which issued during the prosecution of Applicant's PCT/IL201/050451.

(56) References Cited

OTHER PUBLICATIONS

An International Search Report & Written Opinion both dated Mar. 21, 2014, which issued during the prosecution of Applicant's PCT/IL13/50992.
An International Search Report and Written Opinion both dated Apr. 9, 2014, which issued during the prosecution of Applicant's PCT/IL13/50860.
An International Search Report and a Written Opinion both dated Apr. 15, 2014, which issued during the prosecution of Applicant's PCT/IL2013/050861.
An International Search Report & Written Opinion both dated May 12, 2015, which issued during the prosecution of Applicant's PCT/IL2014/050914.
An International Search Report and a Written Opinion both dated May 30, 2007, which issued during the prosecution of Applicant's PCT/IL2006/000342.
An International Search Report and a Written Opinion both dated Jun. 10, 2010, which issued during the prosecution of Applicant's PCT/IL09/01209.
An International Search Report and a Written Opinion both dated Aug. 17, 2010, which issued during the prosecution of Applicant's PCT/IL10/00357.
An International Search Report & Written Opinion both dated Sep. 8, 2009, which issued during the prosecution of Applicant's PCT/IL09/00593.
An International Search Report and a Written Opinion both dated Sep. 12, 2008, which issued during the prosecution of Applicant's PCT/IL07/01503.
An International Search Report and Written Opinion dated Nov. 8, 2010, which issued during the prosecution of Applicant's PCT/IL2010/000358.
An International Search Report and a Written Opinion both dated Nov. 23, 2011, which issued during the prosecution of Applicant's PCT/IL2011/000446.
Supplementary European Search Report dated Sep. 25, 2015, which issued during the prosecution of Applicant's European App No. 09794095.1.
A Supplementary European Search Report dated Feb. 1, 2011, which issued during the prosecution of European Patent Application No. EP 07849540.
An English translation of an Office Action dated Dec. 12, 2013 which issued during the prosecution of Chinese Patent Application No. 200980157331.3.
Communication regarding amended claims filed dated Dec. 27, 2012, regarding European App No. 11792047.0.
An Office Action dated Mar. 23, 2015, which issued during the prosecution of European Patent Application No. EP 09834225.6.
An English translation of an Office Action dated Jul. 17, 2015 which issued during the prosecution of Chinese Patent Application No. 201080059948.4.
An English translation of an Office Action dated Dec. 16, 2015 which issued during the prosecution of Chinese Patent Application No. 201080059948.4.
Communication from the European Patent Office dated Jun. 11, 2015, which issued during the prosecution of European Application No. 11811934.
A communication from the European Patent Office dated Sep. 28, 2011 which issued during the prosecution of European Application No. 09834225.6.
A communication from the European Patent Office dated Oct. 19, 2012 which issued during the prosecution of European Application No. 11792047.0.
An Office Action dated Oct. 23, 2012, which issued during the prosecution of Japanese Patent Application No. 2009-539871.
An English Translation of an Office Action dated Nov. 24, 2015, which issued during the prosecution of Israel Patent Application No. 223448. (the relevant part only).
Notice of Allowance dated Nov. 17, 2015, which issued during the prosecution of U.S. Appl. No. 14/486,226.

Notice of Allowance dated Jan. 29, 2016, which issued during the prosecution of U.S. Appl. No. 14/551,951.
An Office Action dated Jun. 18, 2015, which issued during the prosecution of U.S. Appl. No. 14/551,951.
An Office Action dated Jan. 4, 2016, which issued during the prosecution of U.S. Appl. No. 14/589,100.
An Office Action dated May 4, 2016, which issued the prosecution of U.S. Appl. No. 14/589,100.
An International Search Report and a Written Opinion both dated Nov. 14, 2011, which issued during the prosecution of Applicant's PCT/IL2011/000404.
An International Search Report and a Written Opinion both dated Dec. 6, 2012 which issued during the prosecution of Applicant's PCT/IL2012/000250.
A Notice of Allowance dated Apr. 3, 2013, which issued during the prosecution of U.S. Appl. No. 12/563,930.
An Office Action dated Aug. 24, 2012, which issued during the prosecution of U.S. Appl. No. 12/563,930.
An Office Action dated Dec. 29, 2011, which issued during the prosecution of U.S. Appl. No. 12/563,952.
A Restriction Requirement dated Oct. 27, 2011, which issued during the prosecution of U.S. Appl. No. 12/563,952.
A Notice of Allowance dated May 24, 2012, which issued during the prosecution of U.S. Appl. No. 12/563,952.
An Office Action dated Apr. 1, 2013 which issued during the prosecution of US Patent Application No. 13/167,476.
An Office Action dated Nov. 21, 2013, which issued during the prosecution of U.S. Appl. No. 13/167,476.
An Advisory Action dated Feb. 4, 2014, which issued during the prosecution of U.S. Appl. No. 13/167,476.
A Restriction Requirement dated Oct. 25, 2012 which issued during the prosecution of U.S. Appl. No. 13/167,444.
An Office Action dated Jan. 17, 2013, which issued during the prosecution of U.S. Appl. No. 13/167,444.
An Office Action dated Aug. 26, 2014 which issued during the prosecution of U.S. Appl. No. 13/167,444.
An Office Action dated Aug. 23, 2013 which issued during the prosecution of U.S. Appl. No. 13/167,444.
Notice of Allowance dated Nov. 12. 2015, which issued during the prosecution of U.S. Appl. No. 13/319,007.
Notice of Allowance dated Jan. 7, 2016, which issued during the prosecution of U.S. Appl. No. 13/319,007.
An Office Action dated Oct. 2, 2013, which issued during the prosecution of U.S. Appl. No. 13/167,492.
A Restriction Requirement dated Nov. 2, 2012, which issued during the prosecution of U.S. Appl. No. 13/167,492.
An Office Action dated Feb. 14. 2013 which issued during the prosecution of U.S. Appl. No. 13/167,492.
Notice of Allowance dated Nov. 7, 2014, which issued during the prosecution of U.S. Appl. No. 13/167,492.
An Office Action dated Jun. 10, 2014, which issued during the prosecution of U.S. Appl. No. 13/167,492.
Notice of Allowance dated Dec. 9, 2014, which issued during the prosecution of U.S. Appl. No. 13/167,476.
Notice of Allowance dated Jan. 22, 2015, which issued during the prosecution of U.S. Appl. No. 13/167,444.
An International Preliminary Report on Patentability dated May 1, 2012, which issued during the prosecution of Applicant's PCT/IL2010/000890.
An International Preliminary Report on Patentability dated Jun. 9, 2015, which issued during the prosecution of Applicant's PCT/IL2013/050992.
U.S. Appl. No. 60/873,075, filed Dec. 5, 2006.
U.S. Appl. No. 60/902,146, filed Feb. 16, 2007.
An Office Action dated Mar. 29, 2018, which issued during the prosecution of U.S. Appl. No. 15/188,507.
Notice of Allowance dated Sep. 17, 2014, which issued during the prosecution of U.S. Appl. No. 12/961,721.
An Office Action dated Oct. 1, 2015, which issued during the prosecution of U.S. Appl. No. 14/141,228.
A Restriction Requirement dated Jun. 2, 2014, which issued during the prosecution of U.S. Appl. No. 13/319,030.

(56) References Cited

OTHER PUBLICATIONS

An Office Action dated Oct. 14, 2014, which issued during the prosecution of U.S. Appl. No. 13/319,030.
An Office Action dated Jun. 18, 2015, which issued during the prosecution of U.S. Appl. No. 13/319,030.
An Office Action dated May 3, 2016, which issued during the prosecution of U.S. Appl. No. 13/319,030.
Notice of Allowance dated Dec. 30, 2016, which issued during the prosecution of U.S. Appl. No. 13/319,030.
An Office Action dated Apr. 7, 2015, which issued during the prosecution of U.S. Appl. No. 13/319,007.
An Office Action dated Apr. 8, 2016, which issued during the prosecution of U.S. Appl. No. 14/141,228.
An Office Action dated Oct. 5, 2015, which issued during the prosecution of U.S. Appl. No. 14/246,417.
An Office Action dated Apr. 7, 2016, which issued during the prosecution of U.S. Appl. No. 14/242,151.
An Office Action dated May 23, 2016, which issued during the prosecution of U.S. Appl. No. 14/209,171.
An Office Action dated Jul. 20, 2016, which issued during the prosecution of U.S. Appl. No. 14/246,417.
An Office Action dated Jun. 14, 2016, which issued during the prosecution of U.S. Appl. No. 14/273,155.
An Office Action dated Jun. 17, 2016, which issued during the prosecution of U.S. Appl. No. 14/357,040.
An Office Action dated Mar. 24, 2015, which issued during the prosecution of U.S. Appl. No. 14/486,226.
U.S. Appl. No. 61/001,013, filed Oct. 29, 2007.
U.S. Appl. No. 61/132,295, filed Jun. 16, 2008.
U.S. Appl. No. 61/265,936, filed Dec. 2, 2009.
U.S. Appl. No. 61/283,445, filed Dec. 2, 2009.
U.S. Appl. No. 61/207,908, filed Feb. 17, 2009.
U.S. Appl. No. 61/733,979, filed Dec. 6, 2012.
U.S. Appl. No. 61/717,303, filed Oct. 23, 2012.
U.S. Appl. No. 61/820,979, filed May 8, 2013.
U.S. Appl. No. 61/745,848, filed Dec. 6, 2012.
U.S. Appl. No. 61/555,570, filed Nov. 4, 2011.
U.S. Appl. No. 61/557,082, filed Nov. 8, 2011.
U.S. Appl. No. 60/662,616, filed Mar. 17, 2005.
U.S. Appl. No. 60/700,542, filed Jul. 18, 2005.
U.S. Appl. No. 61/782,121, filed Mar. 14, 2013.
European Search Report dated Jul. 15, 2016, which issued during the prosecution of Applicant's European App No. 13849947.0.
European Search Report dated Nov. 4, 2015, which issued during the prosecution of European Patent Application No. EP 1077 2091.4.
Search Report in European Patent Application 10826224.7 dated Nov. 16, 2015.
Supplementary European Search Report dated Dec. 23, 2014 which issued during the prosecution of Applicant's European U.S. Appl. No. 10/834,311.
Supplementary European Search Report dated Jan. 21, 2014 which issued during the prosecution of Applicant's European App No. 11 78 6226.
A Supplementary European Search Report dated Jan. 20, 2015, which issued during the prosecution of European Patent Application No. 12803037.6.
Supplementary European Search Report dated Aug. 4, 2014 which issued during the prosecution of Applicant's European App No. 11 81 1934.6.
European Search Report dated Jun. 24, 2016, which issued during the prosecution of European Patent Application No. EP 12847363.
Supplementary European Search Report dated Apr. 29, 2015, which issued during the prosecution of Applicant's European App No. 14200202.
An Office Action dated Dec. 16, 2013, which issued during the prosecution of U.S. Appl. No. 13/666,262.
An Office Action dated Dec. 18, 2013, which issued during the prosecution of U.S. Appl. No. 13/666,141.

Notice of Allowance dated Jun. 25, 2014, which issued during the prosecution of U.S. Appl. No. 13/666,262.
A Notice of Allowance dated Feb. 2, 2015, which issued during the prosecution of U.S. Appl. No. 13/504,870.
Notice of Allowance dated Aug. 19, 2013, which issued during the prosecution of U.S. Appl. No. 11/908,906.
An Office Action dated Jun. 8, 2012, which issued during the prosecution of U.S. Appl. No. 11/908,906.
An Office Action dated Dec. 21, 2013, which issued during the prosecution of U.S. Appl. No. 11/908,906.
A Restriction Requirement dated Aug. 5, 2011, which issued during the prosecution of U.S. Appl. No. 11/908,906.
An Office Action dated Sep. 16, 2009 which issued during the prosecution of U.S. Appl. No. 11/950,930.
Notice of Allowance dated Sep. 12, 2014, which issued during the prosecution of U.S. Appl. No. 11/950,930.
An Office Action dated Aug. 5, 2010 which issued during the prosecution of U.S. Appl. No. 11/950,930.
An Office Action dated Feb. 17, 2010 which issued during the prosecution of U.S. Appl. No. 11/950,930.
A Restriction Requirement dated Apr. 19, 2010 which issued during the prosecution of U.S. Appl. No. 12/341,960.
An Office Action dated Sep. 28, 2011, which issued during the prosecution of U.S. Appl. No. 12/437,103.
An Office Action dated Jun. 13, 2012, which issued during the prosecution of U.S. Appl. No. 12/437,103.
A Restriction Requirement dated Jul. 12, 2011, which issued during the prosecution of U.S. Appl. No. 12/437,103.
Notice of Allowance dated Mar. 6, 2014, which issued during the prosecution of U.S. Appl. No. 12/437,103.
Notice of Allowance dated Dec. 20, 2013, which issued during the prosecution of U.S. Appl. No. 12/437,103.
Notice of Allowance dated Apr. 27, 2012, which issued during the prosecution of U.S. Appl. No. 12/341,960.
An Office Action dated Mar. 29, 2011, which issued during the prosecution of U.S. Appl. No. 12/341,960.
An Office Action dated Aug. 4, 2010, which issued during the prosecution of U.S. Appl. No. 12/341,960.
An Interview Summary dated Jul. 27, 2011, which issued during the prosecution of U.S. Appl. No. 12/341,960.
Notice of Allowance dated Aug. 21, 2019, which issued during the prosecution of U.S. Appl. No. 15/703,385.
Notice of Allowance dated Oct. 16, 2019, which issued during the prosecution of U.S. Appl. No. 15/703,385.
Notice of Allowance dated Dec. 24, 2020, which issued during the prosecution of U.S. Appl. No. 15/668,659.
Notice of Allowance dated Oct. 21, 2020, which issued during the prosecution of U.S. Appl. No. 15/668,659.
Declaration of Ivan Vesely, Ph.D., in Support of Petition for Inter Partesreview of U.S. Pat. No. 7,563,267—dated May 29, 2019.
U.S. Appl. No. 60/128,690, filed Apr. 9, 1999.
U.S. Appl. No. 60/613,867, filed Sep. 27, 2004.
An Office Action dated Dec. 24, 2020, which issued during the prosecution of U.S. Appl. No. 16/144,054.
An Office Action dated Feb. 2, 2021, which issued during the prosecution of U.S. Appl. No. 16/811,732.
An Office Action dated Jan. 13, 2021, which issued during the prosecution of European Patent Application No. 15751089.2.
An Office Action together with an English summary dated Mar. 3, 2021, which issued during the prosecution of Chinese Patent Application No. 201780047391.4.
Declaration of Dr. Ivan Vesely, Ph.D. in Support of Petition for Inter Partes Review of U.S. Pat. No. 10,226,341—dated Dec. 17, 2020.
Petition for Inter Partes Review of U.S. Pat. No. 10,226,341 and Exhibits 1001-1013—dated Dec. 29, 2020.
Batista, Randas JV, et al. "Partial left ventriculectomy to treat end-stage heart disease." The Annals of thoracic surgery 64.3 (1997): 634-638.
Beall Jr, Arthur C., et al. "Clinical experience with a dacron velour-covered teflon-disc mitral-valve prosthesis." The Annals of thoracic surgery 5.5 (1968): 402-410.

(56)        References Cited

OTHER PUBLICATIONS

Kalbacher, D., et al. "1000 MitraClip™ procedures: Lessons learnt from the largest single-centre experience worldwide." (2019): 3137-3139.

Maisano, F., et al. "The edge-to-edge technique: a simplified method to correct mitral insufficiency." European journal of cardio-thoracic surgery 13.3 (1998): 240-246.

Fucci, C., et al. "Improved results with mitral valve repair using new surgical techniques." European journal of cardio-thoracic surgery 9.11 (1995): 621-627.

Notice of Allowance dated Nov. 19, 2019, which issued during the prosecution of U.S. Appl. No. 15/668,559.

Mitral Valve Academic Research Consortium. "Clinical Trial Design Principles and Endpoint Definitions for Transcatheter Mitral Valve Repair and Replacement: Part 1: Clinical Trial Design Principles A Consensus Document from the Mitral Valve Academic Research Consortium." Journal of the American College of Cardiology 66.3 (2015): 278-307.

An Office Action dated Aug. 29, 2018, which issued during the prosecution of U.S. Appl. No. 15/329,920.

An Office Action dated May 8, 2018, which issued during the prosecution of U.S. Appl. No. 15/902,403.

An Office Action dated May 11, 2018, which issued during the prosecution of U.S. Appl. No. 15/899,858.

Notice of Allowance dated Oct. 5, 2018, which issued during the prosecution of U.S. Appl. No. 15/886,517.

Notice of Allowance dated Jul. 19, 2019, which issued during the prosecution of U.S. Appl. No. 15/899,858.

Notice of Allowance dated Nov. 16, 2020, which issued during the prosecution of U.S. Appl. No. 16/324,339.

Notice of Allowance dated Apr. 27, 2020, which issued during the prosecution of U.S. Appl. No. 16/591,330.

An Advisory Action dated Jan. 2, 2020, which issued during the prosecution of U.S. Appl. No. 15/668,559.

Notice of Allowance dated Oct. 17, 2019, which issued during the prosecution of U.S. Appl. No. 15/329,920.

An Office Action dated Dec. 31, 2019, which issued during the prosecution of U.S. Appl. No. 16/591,330.

Notice of Allowance dated Feb. 9, 2021, which issued during the prosecution of U.S. Appl. No. 16/937,216.

An Advisory Action dated Nov. 18, 2020, which issued during the prosecution of U.S. Appl. No. 16/811,732.

An International Search Report and a Written Opinion both dated Mar. 27, 2018, which issued during the prosecution of Applicant's PCT/IL2017/050849.

Notice of Allowance dated Jun. 11, 2021, which issued during the prosecution of U.S. Appl. No. 16/811,732.

Notice of Allowance dated Jul. 16, 2021, which issued during the prosecution of U.S. Appl. No. 16/811,732.

Patent Trial and Appeal Board Decision Granting Institution in U.S. Pat. No. 10,226,341—Dated Jul. 20, 2021.

European Search Report dated Jun. 10, 2021 which issued during the prosecution of Applicant's European App No. 21157988.3.

Notice of Allowance dated Nov. 19, 2018, which issued during the prosecution of U.S. Appl. No. 15/197,069.

Poirier, Nancy C., et al. "A novel repair for patients with atrioventricular septal defect requiring reoperation for left atrioventricular valve regurgitation." European journal of cardio-thoracic surgery 18.1 (2000): 54-61.

An Office Action dated Mar. 29, 2021, which issued during the prosecution of U.S. Appl. No. 16/738,516.

Ando, Tomo, et al. "Iatrogenic ventricular septal defect following transcatheter aortic valve replacement: a systematic review." Heart, Lung and Circulation 25.10 (2016): 968-974.

Urena, Marina, et al. "Transseptal transcatheter mitral valve replacement using balloon-expandable transcatheter heart valves: a step-by-step approach." JACC: Cardiovascular Interventions 10.19 (2017): 1905-1919.

An English summary of an Official Action dated Mar. 29, 2021, which issued during the prosecution of Chinese Patent Application No. 201780061210.3.

An International Search Report and a Written Opinion both dated Jan. 28, 2020, which issued during the prosecution of Applicant's PCT/IL2019/051031.

An International Preliminary Report on Patentability dated Mar. 9, 2021, which issued during the prosecution of Applicant's PCT/IL2019/051031.

An Office Action dated May 4, 2021, which issued during the prosecution of U.S. Appl. No. 16/636,204.

Notice of Allowance dated May 17. 2021, which issued during the prosecution of U.S. Appl. No. 16/138,129.

Notice of Allowance dated Jun. 4, 2021, which issued during the prosecution of U.S. Appl. No. 16/802,353.

An Office Action dated May 12, 2021, which issued during the prosecution of Canadian Patent Application No. 2,973,940.

Petition for Inter Partes Review of U.S. Pat. No. 10,702,385—dated Jun. 4, 2021.

Declaration of Ivan Vesely, Ph.D. In Support of Petition for Inter Partes Review of U.S. Pat. No. 10,702,385—dated Jun. 4, 2021.

Notice of Allowance dated Oct. 30, 2018, which issued during the prosecution of U.S. Appl. No. 15/197,069.

An International Search Report and a Written Opinion both dated Jul. 12, 2021, which issued during the prosecution of Applicant's PCT/IL2021/050132.

Notice of Allowance dated Oct. 3, 2019, which issued during the prosecution of U.S. Appl. No. 15/691,032.

An Office Action dated Sep. 6, 2018, which issued during the prosecution of U.S. Appl. No. 15/213,791.

Condado, José Antonio, et al. "Percutaneous edge-to-edge mitral valve repair: 2-year follow-up in the first human case." Catheterization and cardiovascular interventions 67.2 (2006): 323-325.

Notice of Allowance dated Mar. 18. 2020, which issued during the prosecution of U.S. Appl. No. 16/284,331.

Feldman, Ted, et al. "Percutaneous mitral repair with the MitraClip system: safety and midterm durability in the initial EVEREST (Endovascular Valve Edge-to-Edge REpair Study) cohort." Journal of the American College of Cardiology 54.8 (2009): 686-694.

Notice of Allowance dated Nov. 21, 2018, which issued during the prosecution of U.S. Appl. No. 15/213,791.

Notice of Allowance dated Jul. 3, 2019, which issued during the prosecution of U.S. Appl. No. 15/691,032.

IPR2021-00383 Petitioners' Authorized Reply to Patent Owner's Preliminary Response dated May 27, 2021.

Exhibit 1014—Transcript of proceedings held May 20, 2021 (Edwards Lifesciences vs. Cardiovalve).

Exhibit 1015—Facilitate, Meriam-Webster.com, https://www.merriamwebster.com/dictionary/facilitate (visited May 26, 2021).

Patent Owner's Authorized Surreply to Petitioner's Reply to Patent Owner's Preliminary Response dated Jun. 4, 2021(Edwards Lifesciences vs. Cardiovalve).

An Invitation to pay additional fees dated May 19, 2021, which issued during the prosecution of Applicant's PCT/IL2021/050132.

An Office Action dated Aug. 18, 2021, which issued during the prosecution of U.S. Appl. No. 17/210,183.

An Office Action dated Nov. 6, 2015, which issued during the prosecution of U.S. Appl. No. 14/626,267.

An Office Action dated Jan. 26, 2022, which issued during the prosecution of U.S. Appl. No. 16/888,210.

Notice of Allowance dated Oct. 15, 2020, which issued during the prosecution of U.S. Appl. No. 16/740,659.

Notice of Allowance dated Aug. 5, 2020, which issued during the prosecution of U.S. Appl. No. 16/660,231.

Notice of Allowance dated Nov. 18, 2020, which issued during the prosecution of U.S. Appl. No. 16/660,231.

Notice of Allowance dated Dec. 7, 2020, which issued during the prosecution of U.S. Appl. No. 16/678,355.

Notice of Allowance dated Feb. 24. 2020, which issued during the prosecution of U.S. Appl. No. 16/730,090.

Notice of Allowance dated May 6, 2020, which issued during the prosecution of U.S. Appl. No. 16/730,090.

(56) References Cited

OTHER PUBLICATIONS

Notice of Allowance dated May 6, 2020, which issued during the prosecution of U.S. Appl. No. 16/559,365.
Notice of Allowance dated Jul. 23, 2020, which issued during the prosecution of U.S. Appl. No. 16/585,349.
Notice of Allowance dated November 2. 2020, which issued during the prosecution of U.S. Appl. No. 16/585,349.
Notice of Allowance dated Mar. 25, 2020, which issued during the prosecution of U.S. Appl. No. 16/559,365.
An Office Action summarized English translation and Search Report dated Aug. 12, 2021, which issued during the prosecution of Chinese Patent Application No. 201880058940.2.
An Office Action summarized English translation and Search Report dated Oct. 8, 2021, which issued during the prosecution of Chinese Patent Application No. 201780061210.3.
An Office Action dated Nov. 4, 2021, which issued during the prosecution of U.S. Appl. No. 17/366,711.
IPR2021-00383 Final Written Decision Determining All Challenged Claims Unpatentable Denying Patent Owner's Contingent Motion to Amend Granting-in-Part and Denying-in-Part Petitioner's Motion to Strike Denying Patent Owner's Motion to Exclude dated Jul. 18, 2022.
Notice of Allowance dated Dec. 16, 2020, which issued during the prosecution of U.S. Appl. No. 16/520,289.
Notice of Allowance dated Sep. 17, 2020, which issued during the prosecution of U.S. Appl. No. 16/520,289.
An Office Action dated Nov. 25, 2021, which issued during the prosecution of European Patent Application No. 18826823.9.
IPR2021-01051 Institution decision dated Dec. 10, 2021.
Notice of Allowance dated Dec. 7, 2021, which issued during the prosecution of U.S. Appl. No. 17/394,807.
Notice of Allowance dated Dec. 6, 2021, which issued during the prosecution of U.S. Appl. No. 16/738,516.
Notice of Allowance dated Dec. 29, 2021, which issued during the prosecution of U.S. Appl. No. 17/210,183.
IPR2021-00383 Petitioners' Reply To Patent Owner's Response dated Jan. 5, 2022.
IPR2021-00383 Petitioners' Opposition To Patent Owner's Contingent Motion To Amend dated Jan. 5, 2022.
An Office Action dated Sep. 22. 2021, which issued during the prosecution of European Patent Application No. 20714289.4.
Summary of Examination Notice dated Jan. 6, 2022, which issued during the prosecution of Chinese Patent Application No. 201880064313. X.
An Office Action dated Jan. 12, 2022, which issued during the prosecution of U.S. Appl. No. 17/101,787.
Notice of Allowance dated Jun. 20, 2017, which issued during the prosecution of U.S. Appl. No. 14/626,267.
Notice of Allowance dated Oct. 20, 2021, which issued during the prosecution of U.S. Appl. No. 16/636,204.
Notice of Allowance dated Jan. 31, 2022, which issued during the prosecution of U.S. Appl. No. 17/479,418.
An Office Action dated Jan. 13, 2022, which issued during the prosecution of U.S. Appl. No. 17/473,472.
An Office Action dated Apr. 11, 2022, which issued during the prosecution of U.S. Appl. No. 17/473,472.
IPR2021-00383 Preliminary Guidance dated Jan. 31, 2022.
An Office Action dated Mar. 18, 2022, which issued during the prosecution of U.S. Appl. No. 16/746,489.
Notice of Allowance dated Mar. 22, 2022, which issued during the prosecution of U.S. Appl. No. 17/366,711.
Notice of Allowance dated Mar. 4, 2022, which issued during the prosecution of U.S. Appl. No. 16/768,909.
An Office Action dated Dec. 9, 2021, which issued during the prosecution of U.S. Appl. No. 16/135,969.
An Office Action dated Jan. 24, 2022, which issued during the prosecution of U.S. Appl. No. 16/135,466.
U.S. Appl. No. 63/120,808, filed Dec. 3, 2020.
An Advisory Action dated Apr. 9, 2019, which issued during the prosecution of U.S. Appl. No. 15/970,314.

An Advisory Action dated Mar. 13, 2019, which issued during the prosecution of U.S. Appl. No. 15/979,686.
An Advisory Action dated Jul. 8, 2019, which issued during the prosecution of U.S. Appl. No. 15/995,725.
An Office Action dated Nov. 16, 2018, which issued during the prosecution of U.S. Appl. No. 16/042,129.
An Office Action dated Jul. 22, 2020, which issued during the prosecution of U.S. Appl. No. 16/135,447.
IPR2021-01051 Preliminary Guidance Patent Owner's Motion To Amend dated Jun. 24, 2022.
Ex Parte Quayle dated May 2, 2022, which issued during the prosecution of U.S. Appl. No. 16/879,952.
An International Search Report and a Written Opinion both dated May 3, 2022, which issued during the prosecution of Applicant's PCT/IL2021/051433.
An Office Action together with an English Summary dated May 7, 2022 which issued during the prosecution of Chinese Patent Application No. 201880058940.2.
Notice of Allowance dated May 4, 2022, which issued during the prosecution of U.S. Appl. No. 16/680,739.
An Office Action dated Jun. 28, 2022, which issued during the prosecution of U.S. Appl. No. 16/135,969.
An Office Action dated Jul. 8, 2022, which issued during the prosecution of U.S. Appl. No. 16/144,054.
An Advisory Action dated Jan. 2, 2020, which issued during the prosecution of U.S. Appl. No. 16/041,208.
Notice of Allowance dated Apr. 30, 2020, which issued during the prosecution of U.S. Appl. No. 15/970,314.
Notice of Allowance dated Feb. 28, 2022, which issued during the prosecution of U.S. Appl. No. 16/135,599.
Notice of Allowance dated Jan. 10, 2022, which issued during the prosecution of U.S. Appl. No. 16/135,599.
Notice of Allowance dated May 26, 2021, which issued during the prosecution of U.S. Appl. No. 16/135,599.
Notice of Allowance dated Feb. 2, 2022, which issued during the prosecution of U.S. Appl. No. 16/135,619.
Notice of Allowance dated Feb. 15 2022, which issued during the prosecution of U.S. Appl. No. 16/135,619.
Notice of Allowance dated May 12, 2021, which issued during the prosecution of U.S. Appl. No. 16/135,619.
Notice of Allowance dated May 19, 2021, which issued during the prosecution of U.S. Appl. No. 16/135,619.
Notice of Allowance dated Feb. 2, 2022, which issued during the prosecution of U.S. Appl. No. 16/135,663.
Notice of Allowance dated Feb. 16, 2022, which issued during the prosecution of U.S. Appl. No. 16/135,663.
Notice of Allowance dated Sep. 16, 2020, which issued during the prosecution of U.S. Appl. No. 16/135,770.
Notice of Allowance dated Feb. 4, 2022, which issued during the prosecution of U.S. Appl. No. 16/135,447.
Notice of Allowance dated Mar. 24, 2022, which issued during the prosecution of U.S. Appl. No. 16/135,447.
Notice of Allowance dated Mar. 14, 2022, which issued during the prosecution of U.S. Appl. No. 16/135,505.
Notice of Allowance dated Mar. 16, 2021, which issued during the prosecution of U.S. Appl. No. 16/135,505.
Notice of Allowance dated Jun. 15, 2020, which issued during the prosecution of U.S. Appl. No. 16/135,843.
Notice of Allowance dated Jun. 23, 2020, which issued during the prosecution of U.S. Appl. No. 16/135,843.
Notice of Allowance dated Aug. 24, 2021, which issued during the prosecution of U.S. Appl. No. 16/135,979.
Notice of Allowance dated Dec. 24, 2021, which issued during the prosecution of U.S. Appl. No. 16/135,979.
Notice of Allowance dated Feb. 22, 2022, which issued during the prosecution of U.S. Appl. No. 16/135,979.
Notice of Allowance dated Mar. 17, 2021, which issued during the prosecution of U.S. Appl. No. 16/135,979.
Notice of Allowance dated Feb. 8, 2022, which issued during the prosecution of U.S. Appl. No. 16/136,074.
Advisory Action dated Feb. 3, 2021, which issued during the prosecution of U.S. Appl. No. 16/135,505.

(56)          References Cited

OTHER PUBLICATIONS

Advisory Action dated Jan. 14, 2021, which issued during the prosecution of U.S. Appl. No. 16/135,663.

Advisory Action dated Dec. 15, 2020, which issued during the prosecution of U.S. Appl. No. 16/135,969.

Advisory Action dated Jul. 14, 2020, which issued during the prosecution of U.S. Appl. No. 16/520,289.

Notice of Allowance dated Mar. 8, 2019, which issued during the prosecution of U.S. Appl. No. 15/978,494.

Notice of Allowance dated May 22, 2019, which issued during the prosecution of U.S. Appl. No. 15/979,686.

Notice of Allowance dated Apr. 11, 2019, which issued during the prosecution of U.S. Appl. No. 15/994,022.

Notice of Allowance dated Feb. 12, 2020, which issued during the prosecution of U.S. Appl. No. 15/995,725.

Notice of Allowance dated May 1, 2020, which issued during the prosecution of U.S. Appl. No. 15/995,725.

Notice of Allowance dated Aug. 1, 2019, which issued during the prosecution of U.S. Appl. No. 16/008,618.

Notice of Allowance dated Nov. 13, 2019, which issued during the prosecution of U.S. Appl. No. 16/008,618.

Notice of Allowance dated Aug. 28, 2019, which issued during the prosecution of U.S. Appl. No. 16/040,831.

Notice of Allowance dated Dec. 10, 2019, which issued during the prosecution of U.S. Appl. No. 16/040,831.

Notice of Allowance dated Jan. 23, 2020, which issued during the prosecution of U.S. Appl. No. 16/041,208.

Notice of Allowance dated Mar. 5, 2020, which issued during the prosecution of U.S. Appl. No. 16/041,208.

Notice of Allowance dated May 6, 2020, which issued during the prosecution of U.S. Appl. No. 16/041,208.

Notice of Allowance dated Jun. 27, 2019, which issued during the prosecution of U.S. Appl. No. 16/042,028.

Notice of Allowance dated Jul. 3, 2019, which issued during the prosecution of U.S. Appl. No. 16/042,129.

Notice of Allowance dated Feb. 16, 2022, which issued during the prosecution of U.S. Appl. No. 16/136,074.

Notice of Allowance dated Jul. 30, 2021, which issued during the prosecution of U.S. Appl. No. 16/136,074.

Notice of Allowance dated Sep. 24, 2021, which issued during the prosecution of U.S. Appl. No. 16/136,074.

Notice of Allowance dated Dec. 23, 2021, which issued during the prosecution of U.S. Appl. No. 16/136,082.

Notice of Allowance dated Feb. 28, 2022, which issued during the prosecution of U.S. Appl. No. 16/136,082.

An Office Action dated Jun. 20, 2019, which issued during the prosecution of U.S. Appl. No. 15/970,314.

An Office Action dated Nov. 21, 2019, which issued during the prosecution of U.S. Appl. No. 15/970,314.

An Office Action dated Dec. 21, 2018, which issued during the prosecution of U.S. Appl. No. 15/978,494.

An Office Action dated Dec. 28, 2018, which issued during the prosecution of U.S. Appl. No. 15/979,686.

An Office Action dated Feb. 12, 2019, which issued during the prosecution of U.S. Appl. No. 15/994,022.

An Office Action dated Feb. 13, 2019, which issued during the prosecution of U.S. Appl. No. 15/995,725.

An Office Action dated Oct. 22, 2019, which issued during the prosecution of U.S. Appl. No. 15/995,725.

An Office Action dated Apr. 19, 2019, which issued during the prosecution of U.S. Appl. No. 16/008,618.

An Office Action dated Feb. 14, 2019, which issued during the prosecution of U.S. Appl. No. 16/008,618.

An Office Action dated Jun. 19, 2019, which issued during the prosecution of U.S. Appl. No. 16/040,831.

An Office Action dated Sep. 30, 2021, which issued during the prosecution of U.S. Appl. No. 16/135,447.

An Office Action dated Mar. 10, 2021, which issued during the prosecution of U.S. Appl. No. 16/135,447.

An Office Action dated Apr. 15, 2019, which issued during the prosecution of U.S. Appl. No. 15/041,208.

An Office Action dated Jun. 21, 2021, which issued during the prosecution of U.S. Appl. No. 16/135,447.

An Office Action dated Apr. 3, 2020, which issued during the prosecution of U.S. Appl. No. 16/135,466.

An Office Action dated Mar. 27, 2020, which issued during the prosecution of U.S. Appl. No. 16/135,505.

An Office Action dated Sep. 8, 2021, which issued during the prosecution of U.S. Appl. No. 16/135,505.

An Office Action dated Sep. 29,2020, which issued during the prosecution of U.S. Appl. No. 16/135,505.

An Office Action dated Aug. 11, 2020, which issued during the prosecution of U.S. Appl. No. 16/135,619.

An Office Action dated Dec. 21, 2020, which issued during the prosecution of U.S. Appl. No. 16/135,619.

An Office Action dated Apr. 10, 2020, which issued during the prosecution of U.S. Appl. No. 16/135,663.

An Office Action dated Jun. 28, 2021, which issued during the prosecution of U.S. Appl. No. 16/135,663.

An Office Action dated Mar. 8, 2021, which issued during the prosecution of U.S. Appl. No. 16/135,663.

An Office Action dated Sep. 23, 2020, which issued during the prosecution of U.S. Appl. No. 16/135,663.

An Office Action dated Mar. 16, 2020, which issued during the prosecution of U.S. Appl. No. 16/135,770.

An Office Action dated Dec. 10, 2020, which issued during the prosecution of U.S. Appl. No. 16/135,599.

An Office Action dated Jun. 1, 2020, which issued during the prosecution of U.S. Appl. No. 16/135,599.

An Office Action dated Mar. 5, 2020, which issued during the prosecution of U.S. Appl. No. 16/135,843.

An Office Action dated Apr. 9, 2020, which issued during the prosecution of U.S. Appl. No. 16/135,969.

An Office Action dated Jan. 14, 2021, which issued during the prosecution of U.S. Appl. No. 16/135,969.

An Office Action dated May 28, 2021, which issued during the prosecution of U.S. Appl. No. 16/135,969.

An Office Action dated Sep. 9, 2020, which issued during the prosecution of U.S. Appl. No. 16/135,969.

An Office Action dated Mar. 20, 2020, which issued during the prosecution of U.S. Appl. No. 16/135,979.

An Office Action dated Oct. 20, 2020, which issued during the prosecution of U.S. Appl. No. 16/135,979.

An Office Action dated Mar. 6, 2020, which issued during the prosecution of U.S. Appl. No. 16/136,074.

An Office Action dated Mar. 19, 2021, which issued during the prosecution of U.S. Appl. No. 16/136,074.

An Office Action dated Sep. 8, 2020, which issued during the prosecution of U.S. Appl. No. 16/136,074.

An Office Action dated Jan. 25, 2021, which issued during the prosecution of U.S. Appl. No. 16/136,082.

An Office Action dated Jun. 1, 2020, which issued during the prosecution of U.S. Appl. No. 16/136,082.

An Office Action dated Mar. 16, 2020, which issued during the prosecution of U.S. Appl. No. 16/136,110.

An Office Action dated Mar. 12, 2020, which issued during the prosecution of U.S. Appl. No. 16/136,123.

An Office Action dated Mar. 10, 2020, which issued during the prosecution of U.S. Appl. No. 16/136,150.

An Office Action dated Apr. 7, 2020, which issued during the prosecution of U.S. Appl. No. 16/520,289.

An Office Action dated Oct. 7, 2019, which issued during the prosecution of U.S. Appl. No. 16/520,289.

An Office Action dated Oct. 23, 2019, which issued during the prosecution of U.S. Appl. No. 16/559,365.

An Office Action dated Dec. 12, 2019, which issued during the prosecution of U.S. Appl. No. 16/585,349.

An Office Action dated Jul. 16, 2020, which issued during the prosecution of U.S. Appl. No. 16/678,355.

An Office Action dated Mar. 18, 2020, which issued during the prosecution of U.S. Appl. No. 16/740,659.

(56) References Cited

OTHER PUBLICATIONS

Notice of Allowance dated Aug. 11, 2020, which issued during the prosecution of U.S. Appl. No. 16/136,110.
Notice of Allowance dated Sep. 30, 2020, which issued during the prosecution of U.S. Appl. No. 16/136,123.
Notice of Allowance dated Aug. 26, 2020, which issued during the prosecution of U.S. Appl. No. 16/136,150.
Notice of Allowance dated Dec. 10, 2020, which issued during the prosecution of U.S. Appl. No. 16/136,150.
Notice of Allowance dated Dec. 11, 2019, which issued during the prosecution of U.S. Appl. No. 16/507,357.
Notice of Allowance dated Aug. 22, 2019, which issued during the prosecution of U.S. Appl. No. 16/507,357.

PROSTHETIC HEART VALVE WITH FRAMES

CROSS REFERENCES TO RELATED APPLICATIONS

The present application is a Continuation of U.S. Ser. No. 17/734,472 to HaCohen, filed May 2, 2022, and entitled "PROSTHETIC HEART VALVE WITH UPPER SKIRT," which published as US 2022/0257376 (now U.S. Pat. No. 11,839,541) and which is a Continuation of U.S. Ser. No. 17/479,418 to HaCohen, filed Sep. 20, 2021, and entitled "ROTATION-BASED ANCHORING OF AN IMPLANT," (now U.S. Pat. No. 11,351,026) and which is a Continuation of U.S. Ser. No. 16/811,732 to HaCohen, filed Mar. 6, 2020, and entitled "PROSTHETIC HEART VALVE WITH UPPER AND LOWER SKIRTS," (now U.S. Pat. No. 11,141,268) which published as US 2020/0205969 and which is a Continuation of U.S. Ser. No. 16/532,945 to HaCohen, filed Aug. 6, 2019, and entitled "PROSTHETIC HEART VALVE WITH UPPER SKIRT" (now U.S. Pat. No. 10,660,751), which is a Continuation of U.S. Ser. No. 16/388,038 to HaCohen, filed Apr. 18, 2019, and entitled "ROTATION-BASED ANCHORING OF AN IMPLANT" (now U.S. Pat. No. 10,548,726), which is a Continuation of U.S. Ser. No. 16/183,140 to HaCohen, filed Nov. 7, 2018, and entitled "FOLDING RING PROSTHETIC HEART VALVE" (now U.S. Pat. No. 10,610,359), which is a Divisional of U.S. Ser. No. 15/188,507 to HaCohen, filed Jun. 21, 2016, and entitled "FOLDING RING IMPLANT FOR HEART VALVE" (now U.S. Pat. No. 10,231,831), which is a Continuation of U.S. Ser. No. 14/522,987 to HaCohen, filed Oct. 24, 2014, and entitled "IMPLANT FOR ROTA-TION-BASED ANCHORING," which published as US 2015/0045880 (abandoned) and which is a Continuation of U.S. Ser. No. 12/961,721 to HaCohen, filed Dec. 7, 2010, and entitled "ROTATION-BASED ANCHORING OF AN IMPLANT" (now U.S. Pat. No. 8,870,950), which claims the benefit of U.S. Provisional Patent Application 61/283,819, entitled "FOLDABLE HINGED PROSTHETIC HEART VALVE," to Hacohen, filed Dec. 8, 2009, which is incorporated herein by reference.

FIELD OF EMBODIMENTS OF THE INVENTION

Embodiments of the present invention relates in general to valve replacement. More specifically, embodiments of the present invention relate to replacement of an atrioventricular valve and prosthetic valve therefor.

BACKGROUND

Ischemic heart disease causes regurgitation of a heart valve by the combination of ischemic dysfunction of the papillary muscles, and the dilatation of the ventricle that is present in ischemic heart disease, with the subsequent displacement of the papillary muscles and the dilatation of the valve annulus.

Dilation of the annulus of the valve prevents the valve leaflets from fully coapting when the valve is closed. Regurgitation of blood from the ventricle into the atrium results in increased total stroke volume and decreased cardiac output, and ultimate weakening of the ventricle secondary to a volume overload and a pressure overload of the atrium.

SUMMARY OF EMBODIMENTS

In some applications of the present invention, a prosthetic heart valve structure is provided that collapses and expands by means of one or more valve pivot joints. The prosthetic valve structure is typically designated for implantation in a native atrioventricular valve site of a heart of a patient, although for some applications, the prosthetic valve structure is designated for implantation at the aortic or tricuspid valve. The prosthetic valve structure comprises an annular ring portion that is designated for placement adjacent to the ventricular surface of the native valve of the patient. This annular ring portion comprises the valve pivot joints, which facilitate collapsing of the prosthetic valve structure for transcatheter advancement of the valve toward the heart of the patient. Additionally, the annular portion of the prosthetic valve structure is coupled to a plurality of anchors which are configured to grasp the native chordae tendineae of the heart of the patient. These anchors comprise generally curved prong structures which, in an expanded state of the prosthetic valve structure, are aligned circumferentially along the annular ring portion of the prosthetic valve structure (generally perpendicular to a radius of the annular ring portion). Once the annular ring portion is positioned adjacent to the ventricular surface of the native mitral valve, the prosthetic valve structure is rotated, in order for the anchors to engage the native chordae tendineae. During the engaging, portions of the native chordae tendineae are gathered between each anchor and a respective portion of the annular ring. This engaging provides support to the prosthetic valve structure as it is positioned in and replaces the native valve. Additionally, the prosthetic valve structure comprises ventricular and atrial skirts which provide flush positioning of the prosthetic valve in the native valve.

There is therefore provided, in accordance with some applications of the present invention, apparatus for use with a prosthetic valve that is designated for implantation at a native heart valve of a patient, including:

a valve ring having a plurality of ring segments, each of the segments being hingedly coupled to at least one adjacent segment at a pivot joint, the valve ring being configured:

to be placed adjacent to a surface of the native heart valve, the prosthetic valve having been coupled to the valve ring, in an expanded state thereof, to define a ring, all of the pivot joints being disposed in a plane that is perpendicular to a longitudinal axis of the ring, and to be foldable from the expanded state into a shape that has a generally circular cross-section that defines and surrounds at least in part a central lumen, by folding the segments with respect to each other, at the pivot joints.

For some applications, the segments of the ring are configured to become at least partially twisted due to the ring being folded from the expanded state.

For some applications, the prosthetic valve includes a trileaflet valve, and the ring has a number of ring segments that is a multiple of six.

For some applications, the ring has exactly six segments.

For some applications, the prosthetic valve includes a bileaflet valve, and the ring has a number of ring segments that is a multiple of four.

For some applications, the ring has exactly four segments.

There is further provided, in accordance with some applications of the present invention, a method for use with a prosthetic valve that is designated for implantation at a native heart valve of a patient, including:

placing in a vicinity a surface of the native heart valve, a valve ring that is coupled to the valve, while the valve ring is in a folded state thereof, the ring having a plurality of ring segments, each of the segments being hingedly coupled to at least one adjacent segment at a pivot joint, in the folded state thereof, the ring having a shape that has a generally circular cross-section that defines and surrounds at least in part a central lumen;

expanding the ring such that all of the pivot joints become disposed in a plane that is perpendicular to a longitudinal axis of the ring, by applying a force to at least some of the pivot joints; and when the ring is in an expanded state thereof, positioning the ring adjacent to a surface of the native valve.

For some applications, applying the force to some of the pivot joints includes pushing on pivot joints that are disposed on a proximal side of the ring, while the ring is in the folded state thereof.

For some applications, the native valve includes a native mitral valve, and positioning the ring adjacent to the surface of the valve includes positioning the ring adjacent to a ventricular surface of the native mitral valve.

There is additionally provided, in accordance with some applications of the present invention, apparatus for use with a prosthetic valve that is designated for implantation at a native mitral valve of a patient, including:

an annular ring configured to be placed at a ventricular surface of the native mitral valve, the prosthetic valve having been coupled to the annular ring; and at least one anchor disposed circumferentially with respect to the annular ring so as to define a space between the anchor and the annular ring.

For some applications, the anchor is configured to grasp a portion of native chordae tendineae of a heart of the patient by the annular ring being rotated.

For some applications, the annular ring is configured to be collapsible.

For some applications, the ring includes a plurality of ring segments, each of the segments being hingedly coupled to at least one adjacent segment at a pivot joint, and the ring is configured to be collapsed by folding the segments with respect to each other, at the pivot joints.

There is further provided, in accordance with some applications of the present invention, a method, including:

positioning an annular ring portion of a prosthetic valve structure at a ventricular surface of a native heart valve of a patient; and grasping a portion of native chordae tendineae of a heart of the patient by rotating the annular ring portion of the prosthetic valve structure.

In some applications of the present invention, grasping the portion of the native chordae tendineae includes facilitating placing the portion of the native chordae tendineae in a space between a segment of the annular ring portion and an anchor disposed circumferentially with respect to the segment of the annular ring portion.

In some applications of the present invention, positioning the annular ring portion includes:

transcatheterally advancing the prosthetic valve structure toward the native valve of the patient in a collapsed state thereof; and expanding the prosthetic valve structure from the collapsed state.

In some applications of the present invention, expanding the prosthetic valve structure includes pivoting a plurality of segments of the annular ring portion at respective pivot joints that couple together adjacent segments of the annular ring portion.

The present invention will be more fully understood from the following detailed description of embodiments thereof, taken together with the drawings, in which:

DETAILED DESCRIPTION OF THE EMBODIMENTS

Figure 1:
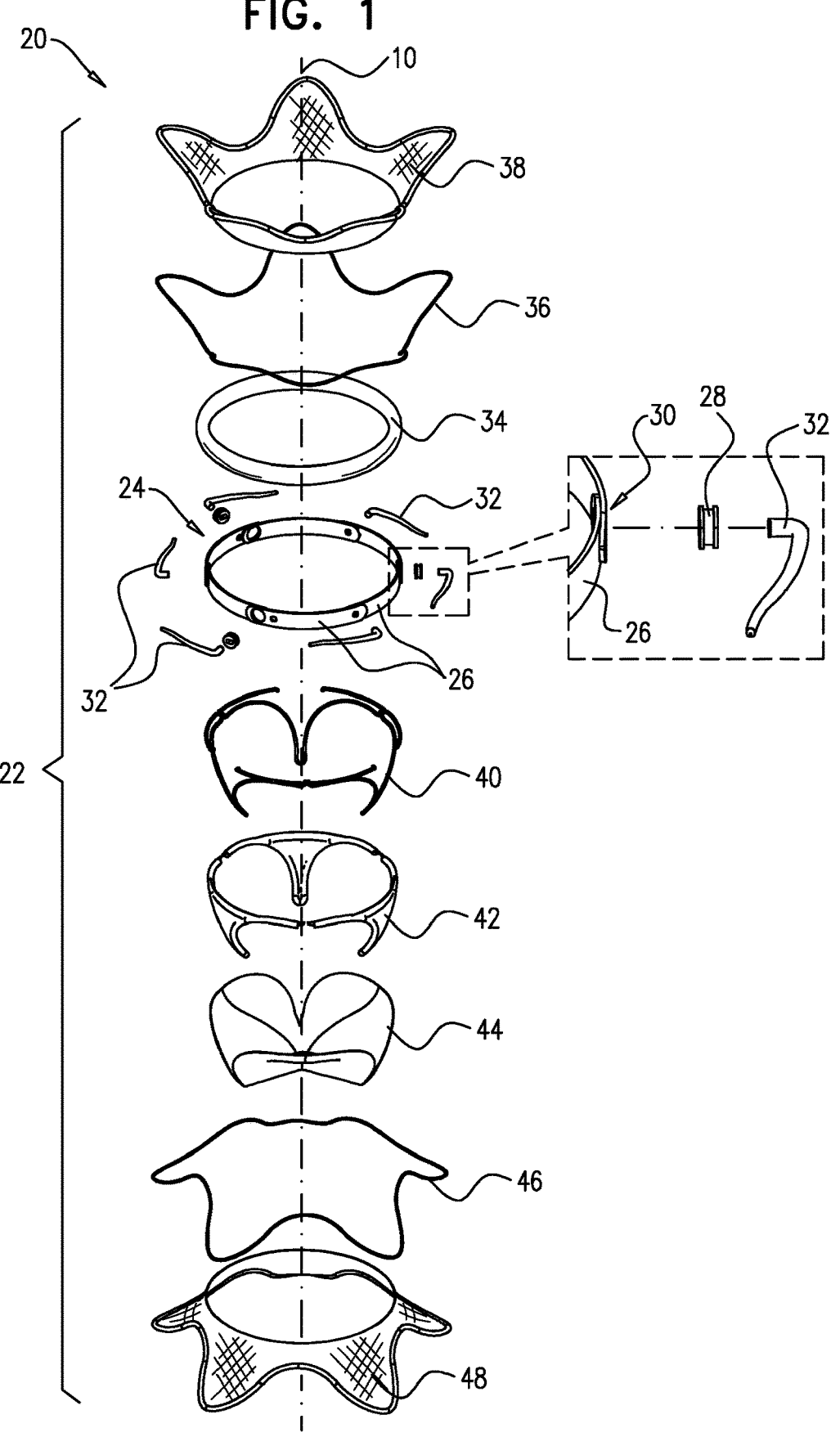
FIG. 1 is a schematic illustration of an exploded view of a prosthetic heart valve, in accordance with some applications of the present invention.

Reference is now made to FIGS. 1-4, which are schematic illustrations of an expandable and collapsible prosthetic valve structure 20, in accordance with some applications of the present invention. The prosthetic valve structure is configured for implantation in and replacement of a native atrioventricular valve of a patient. Typically, the prosthetic valve structure is configured for implantation in and replacement of a native mitral valve of the patient.

The prosthetic valve structure comprises an annular valve ring 24, which comprises a plurality of curved metal segments 26 and a plurality of pivot joints 30 which facilitate the collapsing and expanding of the prosthetic valve structure. The annular valve ring is typically surrounded by a valve ring fabric sleeve 34 comprising a braided mesh of fabric, e.g., Dacron. This sleeve promotes fibrosis following implantation of the prosthetic valve structure in the native valve of the patient. The annular valve ring is coupled to a prosthetic valve that includes a plurality of valve leaflets 44. The valve leaflets are coupled to a flexible valve leaflet frame 40 (e.g., comprising nitinol, by way of illustration and not limitation), which is, in turn, coupled to a valve leaflet frame fabric 42. Typically, the valve leaflet frame fabric (e.g., a fabric comprising Dacron) is coupled to (for example, sutured to) valve ring fabric sleeve 34.

For embodiments in which the prosthetic valve is designated to replace the native mitral valve of the patient, the prosthetic valve comprises three artificial or tissue-based leaflets 44a, 44b, and 44c (shown in FIG. 4), which are coupled to the inner perimeter of the annular valve ring. For example, the leaflets may include pericardium, a polymer, and/or other materials, as would be obvious to one skilled in the art.

Figure 4:
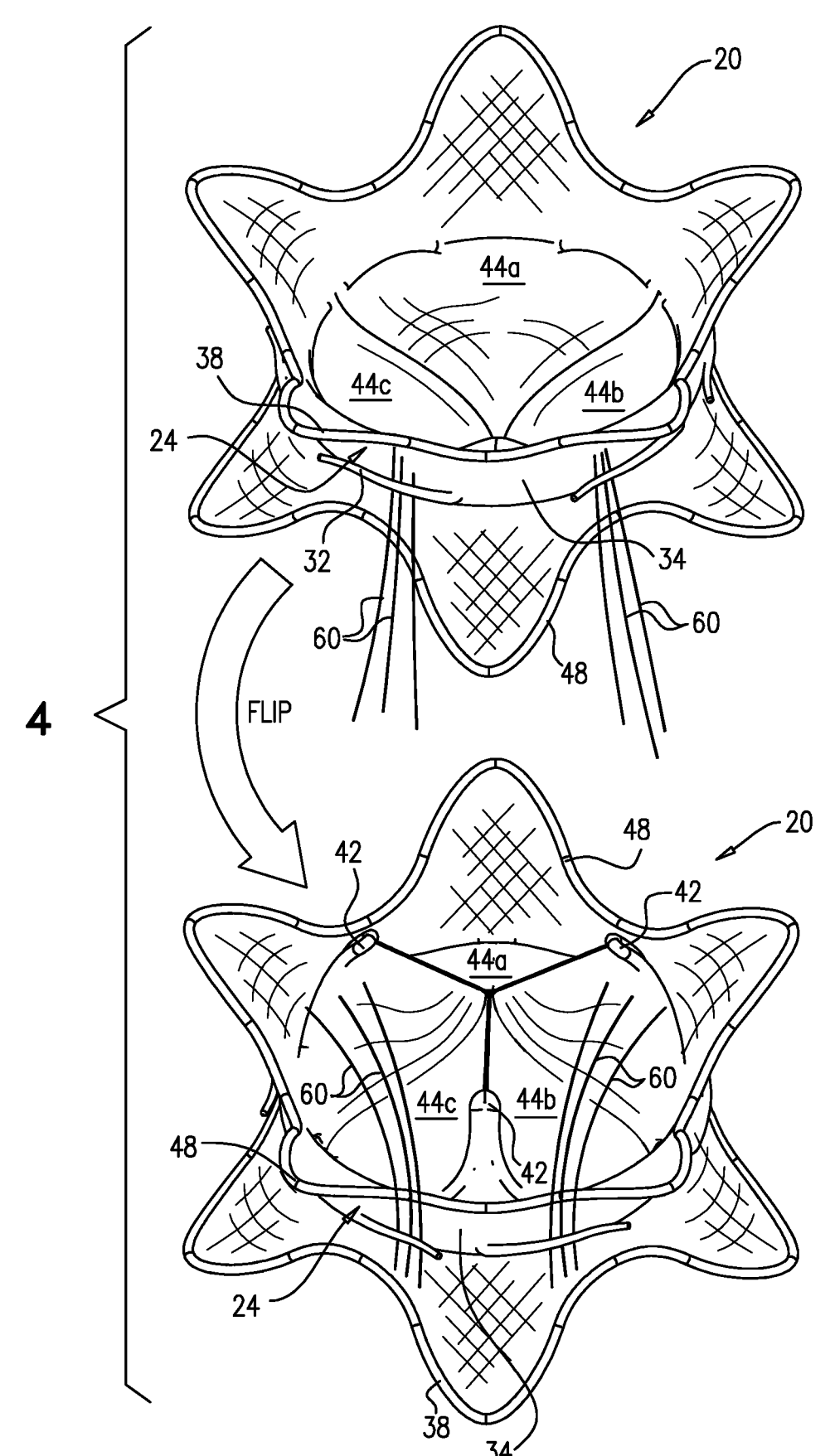
FIG. 4 is a schematic illustration of respective views of the prosthetic heart valve of FIG. 1, while anchors of the valve are anchoring the valve to chordae tendineae of a subject, in accordance with some applications of the present invention.

The annular valve ring portion of the prosthetic valve structure is coupled: (1) at a first surface thereof to an upper skirt, which comprises an upper skirt fabric 38 coupled to a flexible upper skirt frame 36, and (2) at a second surface thereof to a lower skirt, which comprises a lower skirt fabric 48 coupled to a flexible lower skirt frame 46. Typically, the upper and lower frames comprise a flexible material, e.g., nitinol by way of illustration and not limitation. Typically, when the prosthetic valve structure is implanted in the expanded state, as shown in FIG. 4:

(a) the annular valve ring portion is configured to be disposed at a ventricular surface of the native valve, (b) the upper skirt is designated to rest against an atrial portion of the native mitral valve, and (c) the lower skirt is designated to rest against a ventricular surface of the native valve and to push radially the native leaflets of the native valve.

Figure 2A:
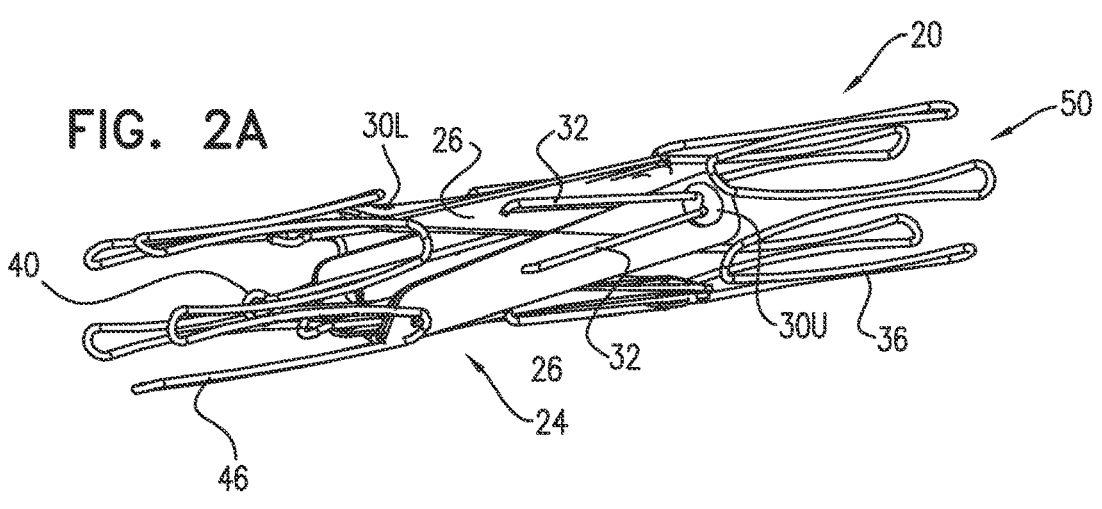
FIGS. 2A-B are schematic illustrations of the prosthetic heart valve of FIG. 1 in an assembled, collapsed state, in accordance with some applications of the present invention.

FIG. 1 shows components 22 of valve structure 20 in an exploded view. Each segment 26 of annular valve ring 24 is coupled at its respective ends to respective ends of adjacent segments via a hinge. For example, as shown, the hinge may include a connecting element 28 that is inserted into holes in the ends of the adjacent segments, such that the adjacent segments form a pivot joint 30. The pivot joints of the ring portion enable the entire prosthetic valve structure to pivot into a collapsed state, the collapsed state being shown in FIGS. 2A-B. Typically, the valve comprises: (a) three "upper" valve pivot joints 30U (shown in FIG. 2A) which are disposed at 120 degrees along the annular valve ring and are near the upper skirt frame 36, in the collapsed state of the valve, shown in FIG. 2A; and (b) three "lower" valve pivot joints 30L (shown in FIG. 2A) also disposed with a separation therebetween of 120 degrees, alternating with the upper valve pivot joints. The lower valve pivot joints are near the lower skirt frame 46, in the collapsed state of the valve as shown in FIG. 2A. The upper valve pivot joints are exposed at a proximal portion of the valve in the collapsed state of the valve (i.e., adjacent to an upper skirt region of the prosthetic valve structure, as shown in FIG. 2A), such that a physician is able to push on the upper valve pivot joints with a pushing tool, as described hereinbelow. Typically, when the ring is in its expanded state, all of the pivot joints are disposed in a plane that is perpendicular to longitudinal axis 10 of ring 24.

Figure 2B:
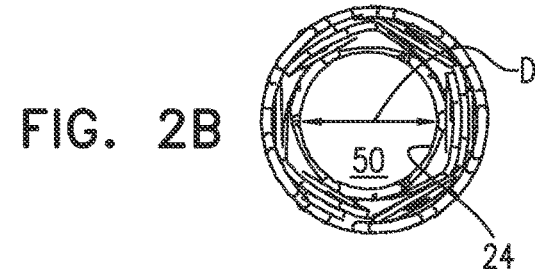

The pivot joints enable the prosthetic valve structure to collapse to form a shape having a generally circular cross-section that defines and surrounds at least in part a central lumen 50, as shown in FIGS. 2A-B. Typically, the pivot joints enable the valve to assume an outer diameter of less than 10 mm, e.g., less than 6 mm (by way of illustration and not limitation), in its collapsed state, as shown in FIG. 2A. Further typically, central lumen 50 (which is defined by ring 24 in its collapsed state) has a cross-sectional length (e.g., diameter D, shown in FIG. 2B) of between 3 mm and 5 mm, the length being measured in a plane that is perpendicular to longitudinal axis 10 of the valve (shown in FIG. 1).

Typically, when used with a trileaflet valve, ring 24 includes six segments 26, such that there are a total of six pivot joints 30 (of which three are upper pivot joints 30U, and three are lower pivot joints 30L), and such that each of the leaflets is disposed between two adjacent upper pivot joints 30U, or two adjacent lower pivot joints 30L. For some applications, the ring includes twelve (or another multiple of six) pivot joints, such that each of the leaflets of a trileaflet valve is disposed between two non-adjacent upper pivot joints 30U, or two non-adjacent lower pivot joints 30L. For some applications, ring 24 is used with a bileaflet valve. For such applications, the ring may include four, eight, or twelve segments 26, such that there are a corresponding number of pivot joints, and such that each of the leaflets is disposed between two of the upper pivot joints or two of the lower pivot joints.

Each of segments 26 of ring 24 is configured to become twisted when the ring is folded, as shown in FIG. 2A. For some applications, due to shape-memory properties of the segments, the segments facilitate the expansion of the ring, since the segments are pre-shaped in non-twisted shapes.

In the collapsed state of the valve, the valve leaflet frame, the valve leaflets, the upper skirt, and the lower skirt are also collapsed. Typically, the valve is configured such that the expansion of the ring causes each of the aforementioned portions to become expanded automatically.

Figure 3:
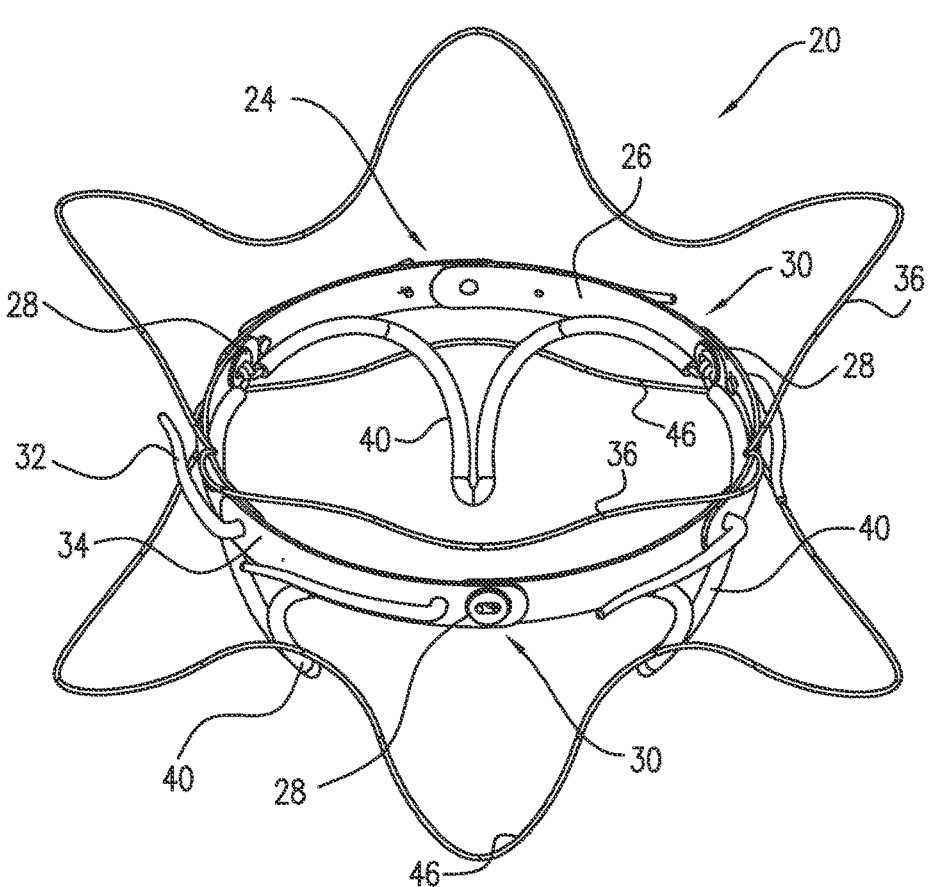
FIG. 3 is a schematic illustration of the prosthetic heart valve of FIG. 1 in an assembled, expanded state, in accordance with some applications of the present invention.

In order to deploy prosthetic valve structure 20 inside the heart, the physician pushes the upper pivot joints 30U distally, using a pushing tool. The pushing of the upper pivot joints enables annular valve ring 24 to expand radially in order for the prosthetic valve structure to assume an expanded state, as shown in FIG. 3. Responsively to the expanding of the prosthetic valve structure, valve leaflet frame 40, valve leaflets 44, upper skirt frame 36, and lower skirt frame 46 also expand from their respective collapsed states.

For some applications, annular valve ring 24 is coupled to a plurality of generally curved, prong-shaped anchors 32, for example, four to eight anchors, e.g., six anchors, as shown by way of illustration and not limitation in FIG. 1. In the expanded state of valve structure 20, as shown in FIG. 3, the anchors are disposed circumferentially and in concentric alignment with the annular valve ring. As shown in FIG. 3, the anchors project from the annular valve ring through the valve ring fabric sleeve 34. As the prosthetic valve structure transitions to a collapsed state, as shown in FIG. 2A, the anchors remain alongside respective segments of the annular valve ring to which each anchor is adjacently disposed in the expanded state of the prosthetic valve structure.

During implantation of prosthetic valve structure 20, a lower portion of the prosthetic valve structure is first advanced toward the ventricular surface of the native valve. Once the distal end of the catheter is positioned in the ventricle of the patient, the physician pushes distally on the upper valve pivot joints 30 in order to (1) expose annular valve ring portion 24 and the lower skirt frame 46 and lower skirt fabric 48 from within the catheter, and (2) in conjunction, expand the annular valve ring. As the annular valve ring expands, lower skirt frame 46, valve leaflet frame 40, and valve leaflets 44 passively (i.e., automatically) expand. As the physician expands the annular valve ring, each of the anchors remain disposed circumferentially with respect to the segment of the annular valve ring to which the anchor is adjacently disposed (as shown in FIG. 3). In such a manner, a space is created between each anchor and the respective segments of the annular valve ring to which each anchor is adjacently disposed.

By pulling proximally on the catheter and the tool coupled to prosthetic valve structure 20 disposed therein, the annular valve ring is positioned adjacent to a ventricular surface of the native valve. Once the valve ring portion is positioned adjacent to the ventricular surface, the physician rotates annular valve ring 24 (e.g., by rotating 30 degrees a tool coupled thereto) about an axis that runs between the native valve from the atrium to the ventricle (which during implantation of the valve, is typically approximately aligned with longitudinal axis 10 of the valve). During this rotation, portions of native chordae tendineae 60 are grasped and placed between each anchor and the respective segment of the annular valve ring to which the anchor is adjacently disposed, as shown in FIG. 4. This grasping of the leaflets provides supplemental support to the prosthetic valve during and following implantation thereof. Alternatively or additionally, support is provided to the prosthetic valve by the upper and lower skirts, and/or by ring 24.

In conjunction with the grasping of the chordae tendineae, the prosthetic valve is secured in place. The physician then pulls the catheter proximally in order to expose upper skirt frame 36 and upper skirt fabric 38 from within the catheter. The skirt then expands over the atrial surface of the native valve in order to create a flush coupling between the prosthetic valve and the native valve.

Figure 5:
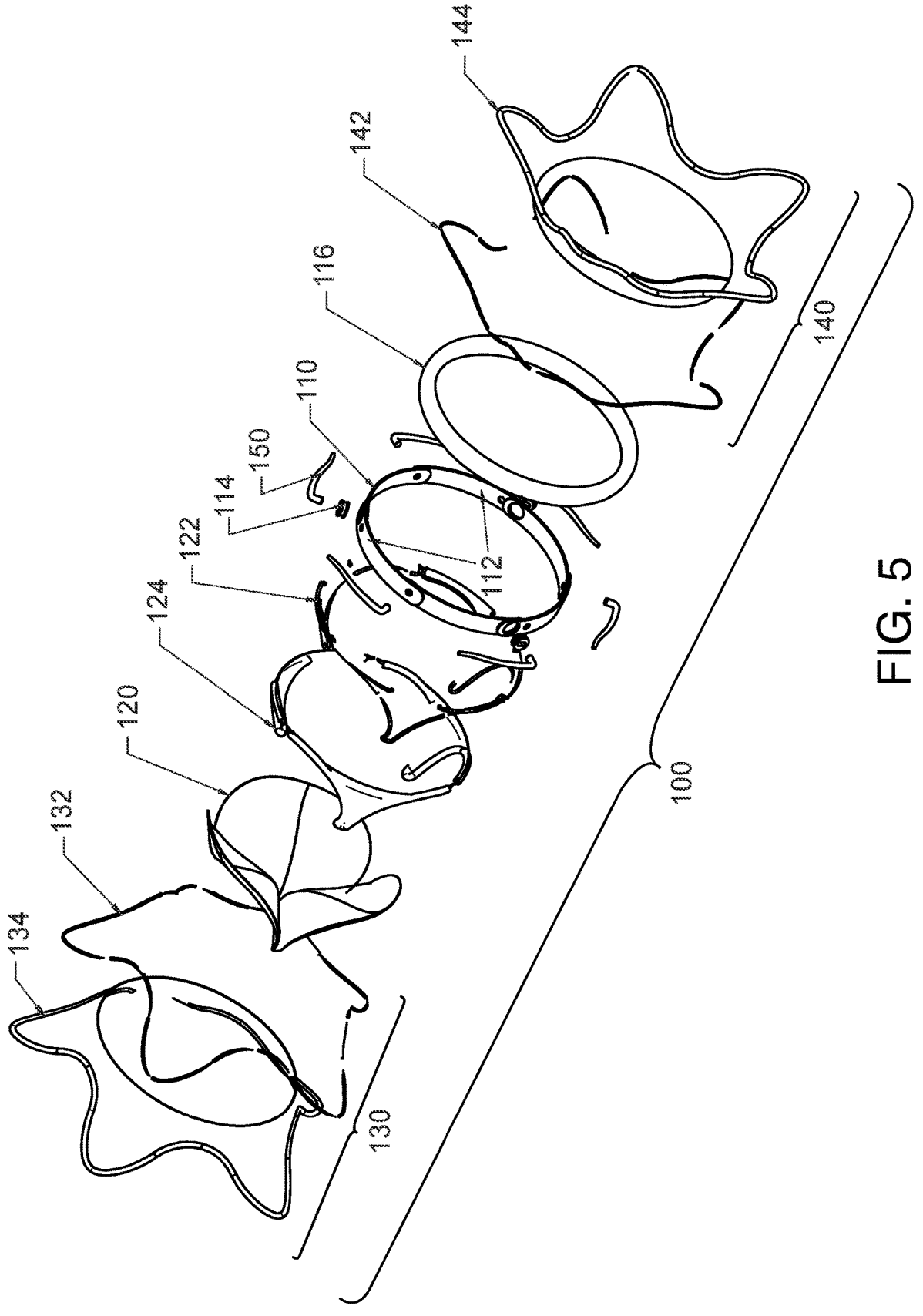
FIG. 5 is a schematic illustration of an exploded view of a prosthetic heart valve, in accordance with some applications of the present invention.
Figure 6:
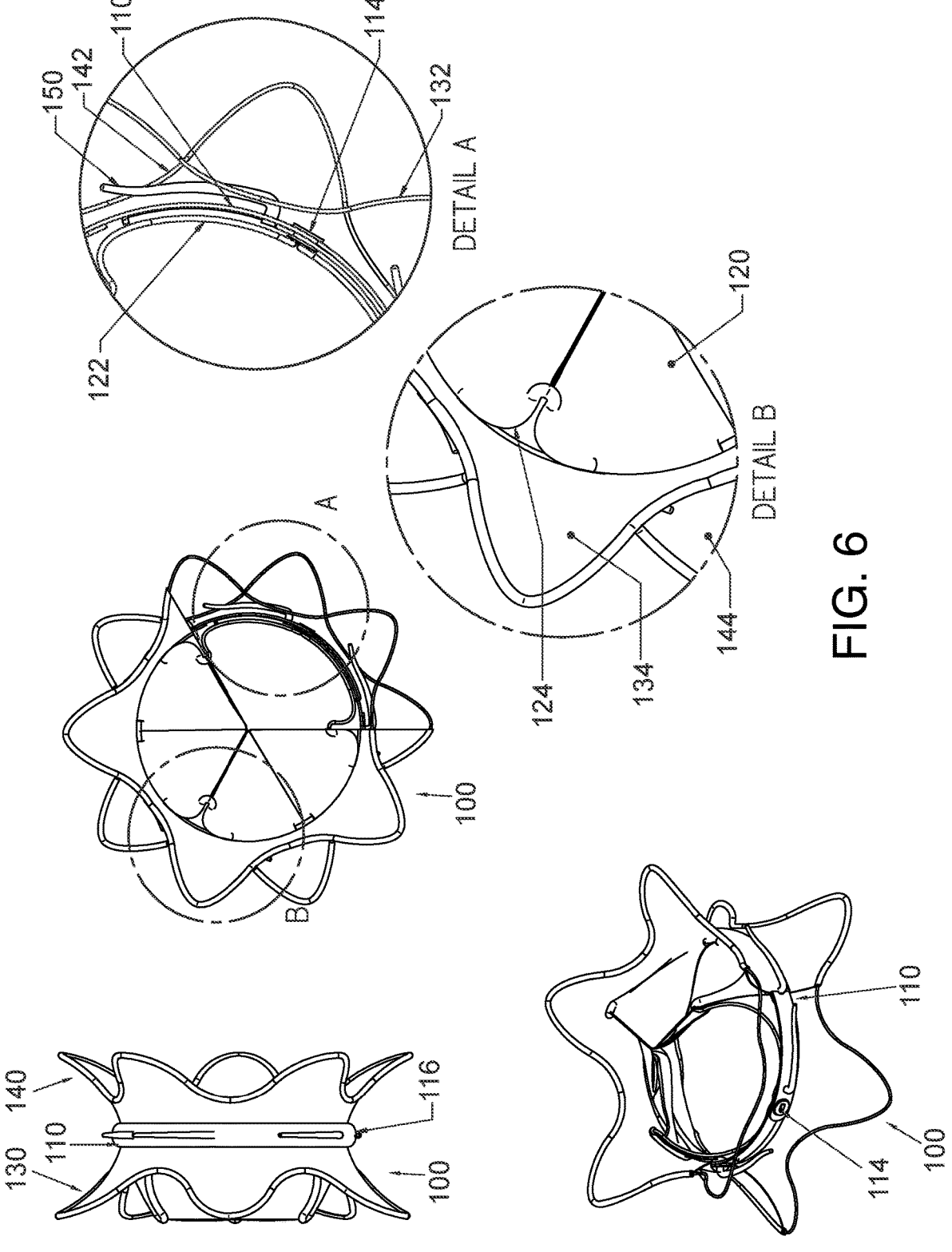
FIG. 6 is a schematic illustration of the prosthetic heart valve of FIG. 5 in an assembled, expanded state, in accordance with some applications of the present invention.
Figure 7:
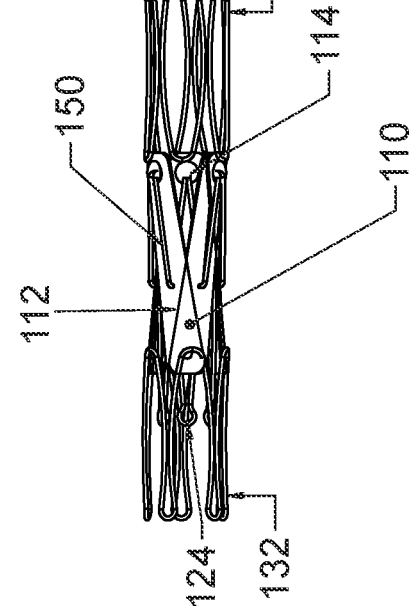
FIG. 7 is a schematic illustration of the prosthetic heart valve of FIG. 5 in an assembled, collapsed state, in accordance with some applications of the present invention.
Figure 7:
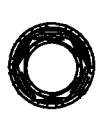
Figure 7:
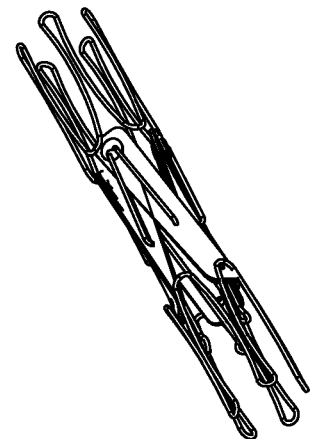

The following description, mutatis mutandis, originates from U.S. Provisional Patent Application 61/283,819 to HaCohen, which was incorporated by reference into the original specification of U.S. Ser. No. 12/961,721 to HaCohen:

Reference is now made to FIGS. 5-7 which are schematic illustrations of an expandable and collapsible prosthetic valve 100, in accordance with some applications of the present invention. The prosthetic valve is configured for implantation in and replacement of a native atrioventricular valve of a patient. Typically, the prosthetic valve is configured for implantation in and replacement of a native mitral valve of the patient. The prosthetic valve comprises an annular valve ring 110 (as shown in the exploded view of FIG. 5), which comprises a plurality of curved metal segments 112 and a plurality of pivot joints 114 which facilitate the collapsing and expanding of the prosthetic valve. The annular valve ring 110 is typically surrounded by a valve ring fabric sleeve 116 comprising a braided mesh of fabric, e.g., Dacron. This sleeve promotes fibrosis following implantation of the prosthetic valve in the native valve of the patient. The annular valve ring 110 is coupled to a plurality of valve leaflets 120. The valve leaflets are coupled to a flexible valve leaflet frame 122 (e.g., comprising nitinol by way of illustration and not limitation), which is, in turn, coupled to a valve leaflet frame fabric 124. Typically, the valve leaflet frame fabric (e.g., a fabric comprising Dacron) is coupled to (for example, sutured to) the valve ring fabric sleeve.

For embodiments in which the prosthetic valve is designated to replace the native mitral valve of the patient, the prosthetic valve comprises three artificial or tissue-based leaflets 120, as shown, which are coupled to the inner perimeter of the annular valve ring. It is to be noted that although these leaflets are shown by way of illustration and not limitation, as being a product of Neovasc Medical Ltd., the leaflets may comprise any other leaflets known in the art.

The annular valve ring portion 110 of the prosthetic valve is coupled: (1) at a first surface thereof to an upper skirt 140, which comprises an upper skirt fabric 144 coupled to a flexible upper skirt frame 142, and (2) at a second surface thereof to a lower skirt 130, which comprises a lower skirt fabric 134 coupled to a flexible lower skirt frame 132. Typically, the upper and lower frames comprise a flexible material, e.g., nitinol by way of illustration and not limitation. Typically, when the prosthetic valve is implanted in the expanded state, as shown in FIG. 6:

(a) the annular valve ring portion is configured to be disposed at a ventricular surface of the native valve, (b) the upper skirt is designated to rest against an atrial portion of the native mitral valve, and (c) the lower skirt is designated to rest against a ventricular surface of the native valve and to push radially the native leaflets of the native valve.

FIG. 5 shows the components of the valve in an exploded view. Each segment 112 of the annular valve ring is coupled at its respective ends to respective ends of adjacent segments via a hinge, or a valve pivot joint 114. The pivot joints of the ring portion enable the entire prosthetic valve to pivot into a collapsed state, as shown in FIG. 7. Typically, the valve comprises: (a) three "upper" valve pivot joints which are disposed at 120 degrees along the annular valve ring and are near the upper skirt frame, as shown in FIG. 7; and (b) three "lower" valve pivot joints also disposed with a separation therebetween of 120 degrees, alternating with the upper valve pivot joints. The lower valve pivot joints are near the lower skirt frame, as shown in FIG. 7). The upper valve pivot joints are exposed at a proximal portion of the valve in a collapsed state (i.e., adjacent to an upper skirt region of the prosthetic valve, as shown in FIG. 7). The pivot joints enable the prosthetic valve to assume a diameter of 6 mm (by way of illustration and not limitation) in its collapsed state, as shown in FIG. 7. In the collapsed state, the valve leaflet frame, the valve leaflets, the upper skirt, and the lower skirt are also collapsed.

In order to deploy the prosthetic valve inside the heart, the physician distally pushes on the upper pivot joints using a pushing tool. The pushing of the upper pivot joints enables the annular valve ring to expand radially in order for the prosthetic valve to assume an expanded state, as shown in FIG. 6. Responsively to the expanding of the prosthetic valve, the valve leaflet frame, the valve leaflets, the upper skirt, and the lower skirt also expand from their respective collapsed states.

The annular valve ring is coupled to a plurality of generally curved, prong-shaped anchors 150, e.g., 6 as shown by way of illustration and not limitation in FIG. 5. In an expanded state, as shown in FIG. 6, the anchors are disposed circumferentially and in concentric alignment with the annular valve ring. As shown in FIG. 6, the anchors project from the annular valve ring through the valve ring fabric sleeve. As the prosthetic valve transitions to a collapsed state, as shown in FIG. 7, the anchors remain alongside respective segments of the annular valve ring to which each anchor is adjacently disposed in the expanded state of the prosthetic valve.

During implantation of the prosthetic valve, a lower portion of the prosthetic valve is first advanced toward the ventricular surface of the native valve. Once the distal end of the catheter is positioned in the ventricle of the patient, the physician pushes distally on the upper valve pivot joints in order to (1) expose the annular valve ring portion and the lower skirt from within the catheter, and (2) in conjunction, expand the annular valve ring. As the annular valve ring expands, the lower skirt, the valve leaflet frame, and the valve leaflets passively expand. As the physician expands the annular valve ring, each of the anchors remain disposed circumferentially with respect to the segment of the annular valve ring to which the anchor is adjacently disposed (as shown in FIG. 6). In such a manner a space is created between each anchor and the respective segments of the annular valve ring to which each anchor is adjacently disposed.

By pulling proximally on the catheter and the tool coupled to the prosthetic valve disposed therein, the annular valve ring is positioned adjacent to a ventricular surface of the native valve. Once the valve ring portion is positioned adjacent to the ventricular surface, the physician rotates the annular valve ring (e.g., by rotating 30 degrees a tool coupled thereto) about an axis that runs between the native valve from the atrium to the ventricle. During this rotation, portions of the native chordeae tendineae are grasped and placed between each anchor and the respective segment of the annular valve ring to which the anchor is adjacently disposed. This grasping of the leaflets provides supplemental support to the prosthetic valve during and following implantation thereof.

In conjunction with the grasping of the chordeae tendineae, the prosthetic valve is secured in place. The physician then pulls the catheter proximally in order to expose the upper skirt from within the catheter. The skirt then expands over the atrial surface of the native valve in order to create a flush coupling between the prosthetic valve and the native valve.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A prosthetic heart valve for implantation at a native heart valve of a heart, the prosthetic heart valve configured to assume a collapsed state for transcatheter delivery and an expanded state, the prosthetic heart valve comprising:

a first frame shaped so as to define metal segments, the first frame defining a lumen therethrough, wherein (i) when the prosthetic heart valve is in the collapsed state, the first frame is in a collapsed state, and (ii) when the prosthetic heart valve is in the expanded state, the first frame is in an expanded state;

a leaflet frame which is coupled to and disposed within the lumen of the first frame in the collapsed state of the prosthetic heart valve;

a second frame configured to be placed against an upstream surface of the native valve;

a plurality of prosthetic leaflets, which are coupled to the leaflet frame, and configured to facilitate upstream-to-downstream bloodflow longitudinally through the prosthetic heart valve; and fabric that:

couples the first and second frames together in the collapsed and expanded states of the prosthetic heart valve, and in the expanded state of the prosthetic heart valve, separates a downstream end of the second frame and an upstream end of the metal segments of the first frame in a manner in which a gap is defined between the first frame and the second frame, with no metallic structure being disposed within the gap.

2. The prosthetic heart valve according to claim 1, wherein, when the prosthetic heart valve is in the expanded state, the second frame is shaped so as to define upstream peaks and downstream troughs, and wherein the downstream troughs define the downstream end of the second frame.

3. The prosthetic heart valve according to claim 1, further comprising a plurality of anchors extending from the metal segments of the first frame.

4. The prosthetic heart valve according to claim 1, wherein the native heart valve is a native mitral valve, and wherein the second frame is configured to rest against the atrial surface within a left atrium of the heart when the prosthetic heart valve is in the expanded state.

5. The prosthetic heart valve according to claim 1, wherein an upstream end of the second frame is upstream of the upstream end of the metal segments of the first frame.

6. The prosthetic heart valve according to claim 5, wherein the downstream end of the second frame is upstream of the upstream end of the metal segments of the first frame.

7. The prosthetic heart valve according to claim 1, wherein an upstream end of the second frame is upstream of an upstream end of the leaflet frame.

8. The prosthetic heart valve according to claim 7, wherein the downstream end of the second frame is upstream of the upstream end of the leaflet frame.

9. A system comprising the prosthetic heart valve according to claim 1, further comprising a catheter for delivering the prosthetic heart valve, the catheter housing the prosthetic heart valve in the compressed state, with the first frame arranged distally relative to the second frame.

10. A prosthetic heart valve for implantation at a native heart valve of a heart, the prosthetic heart valve configured to assume a collapsed state for transcatheter delivery and an expanded state, the prosthetic heart valve comprising:

a first frame shaped so as to define metal segments, the first frame defining a lumen therethrough, wherein (i) when the prosthetic heart valve is in the collapsed state, the first frame is in a collapsed state, and (ii) when the prosthetic heart valve is in the expanded state, the first frame is in an expanded state;

a leaflet frame which is coupled to and disposed within the lumen of the first frame in the collapsed state of the prosthetic heart valve;

a second frame configured to be placed against an upstream surface of the native valve;

a plurality of prosthetic leaflets, which are coupled to the leaflet frame, and configured to facilitate upstream-to-downstream bloodflow longitudinally through the prosthetic heart valve; and fabric that:

couples the first and second frames together in the collapsed and expanded states of the prosthetic heart valve, and in the expanded state of the prosthetic heart valve, separates a downstream end of the second frame and an upstream end of the metal segments of the first frame in a manner in which the first frame is coupled to the second frame only via the fabric.

11. The prosthetic heart valve according to claim 10, wherein, when the prosthetic heart valve is in the expanded state, the second frame is shaped so as to define upstream peaks and downstream troughs, and wherein the downstream troughs define the downstream end of the second frame.

12. The prosthetic heart valve according to claim 10, further comprising a plurality of anchors extending from the metal segments of the first frame.

13. The prosthetic heart valve according to claim 10, wherein the native heart valve is a native mitral valve, and wherein the second frame is configured to rest against the atrial surface within a left atrium of the heart when the prosthetic heart valve is in the expanded state.

14. The prosthetic heart valve according to claim 10, wherein an upstream end of the second frame is upstream of the upstream end of the metal segments of the first frame.

15. The prosthetic heart valve according to claim 14, wherein the downstream end of the second frame is upstream of the upstream end of the metal segments of the first frame.

16. The prosthetic heart valve according to claim 10, wherein an upstream end of the second frame is upstream of an upstream end of the leaflet frame.

17. The prosthetic heart valve according to claim 16, wherein the downstream end of the second frame is upstream of the upstream end of the leaflet frame.

18. A system comprising the prosthetic heart valve according to claim 10, further comprising a catheter for delivering the prosthetic heart valve, the catheter housing the prosthetic heart valve in the compressed state, with the first frame arranged distally relative to the second frame.

* * * * *